US008217645B2

(12) United States Patent
Iida et al.

(10) Patent No.: US 8,217,645 B2
(45) Date of Patent: Jul. 10, 2012

(54) POSITION DETECTING SYSTEM AND POSITION DETECTING METHOD USING AN EVALUATION FUNCTION

(75) Inventors: Takahiro Iida, Hachioji (JP); Atsushi Chiba, Hachioji (JP); Atsushi Kimura, Akiruno (JP); Akio Uchiyama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 51 days.

(21) Appl. No.: 12/882,336

(22) Filed: Sep. 15, 2010

(65) Prior Publication Data

US 2011/0181273 A1 Jul. 28, 2011

Related U.S. Application Data

(63) Continuation of application No. PCT/JP2010/052099, filed on Feb. 12, 2010.

(30) Foreign Application Priority Data

Mar. 16, 2009 (JP) .................................. 2009-062978
Apr. 27, 2009 (JP) .................................. 2009-107875

(51) Int. Cl.
*G01B 7/14* (2006.01)
(52) U.S. Cl. ............................... 324/207.12; 324/207.17
(58) Field of Classification Search ............. 324/207.12, 324/107.16, 207.17, 207.16
See application file for complete search history.

(56) References Cited

U.S. PATENT DOCUMENTS

| 2003/0229268 A1* | 12/2003 | Uchiyama et al. ............ 600/109 |
| 2007/0185398 A1* | 8/2007 | Kimura et al. ................ 600/424 |
| 2009/0018434 A1 | 1/2009 | Kimura et al. |
| 2009/0171190 A1* | 7/2009 | Uchiyama et al. ............ 600/424 |
| 2010/0060472 A1 | 3/2010 | Kimura et al. |
| 2010/0156399 A1* | 6/2010 | Chiba et al. ............... 324/207.13 |
| 2010/0204566 A1* | 8/2010 | Uchiyama et al. ............ 600/424 |

FOREIGN PATENT DOCUMENTS

| JP | 2004-528890 A | 9/2004 |
| JP | 2005-245963 | 9/2005 |

(Continued)

OTHER PUBLICATIONS

Decision on Patent Grant dated Jul. 5, 2011 together with an English language translation.

(Continued)

*Primary Examiner* — Jay Patidar
(74) *Attorney, Agent, or Firm* — Scully, Scott, Murphy & Presser, P.C.

(57) ABSTRACT

A position detecting system including: a detected object disposed in a space; and an external device disposed outside the space, wherein the detected object includes a resonant circuit, and the external device includes at least two drive coils; at least two drive-signal input units; at least one sense coil; a signal adjustment unit that adjusts a phase or amplitude of a drive signal using an evaluation function for evaluating the phase or the amplitude, based on an intensity of the magnetic field; and a position deriving unit that derives a position of the detected object based on a magnetic field detected by the sense coil, wherein the evaluation function derives a solution by adding or multiplying a weight set according to a positional relation between each drive coil and each sense coil to or by an intensity of a magnetic field detected by the sense coils.

23 Claims, 31 Drawing Sheets

FOREIGN PATENT DOCUMENTS

| | | |
|---|---|---|
| JP | 2007-054246 | 3/2007 |
| JP | 2007-190164 | 8/2007 |
| JP | 2008-006056 | 1/2008 |
| JP | 2008-079913 | 4/2008 |
| JP | 2008-155042 A | 7/2008 |
| JP | 2008-272150 | 11/2008 |
| JP | 2009-039356 A | 2/2009 |
| JP | 2008-155042 A | 7/2010 |
| WO | 02/080753 A | 10/2002 |
| WO | WO 2007/023716 A1 | 3/2007 |
| WO | 2007/123217 A1 | 11/2007 |
| WO | WO 2008/038753 A1 | 4/2008 |
| WO | 2008/136281 A1 | 11/2008 |
| WO | 2008/015528 A1 | 12/2008 |
| WO | 2008/155828 A1 | 12/2008 |
| WO | 2009/031456 A1 | 3/2009 |

OTHER PUBLICATIONS

International Search Report dated May 18, 2010.
Japanese Office Action dated Nov. 24, 2010.
Japanese Office Action dated Mar. 15, 2011, together with English Translation.

* cited by examiner

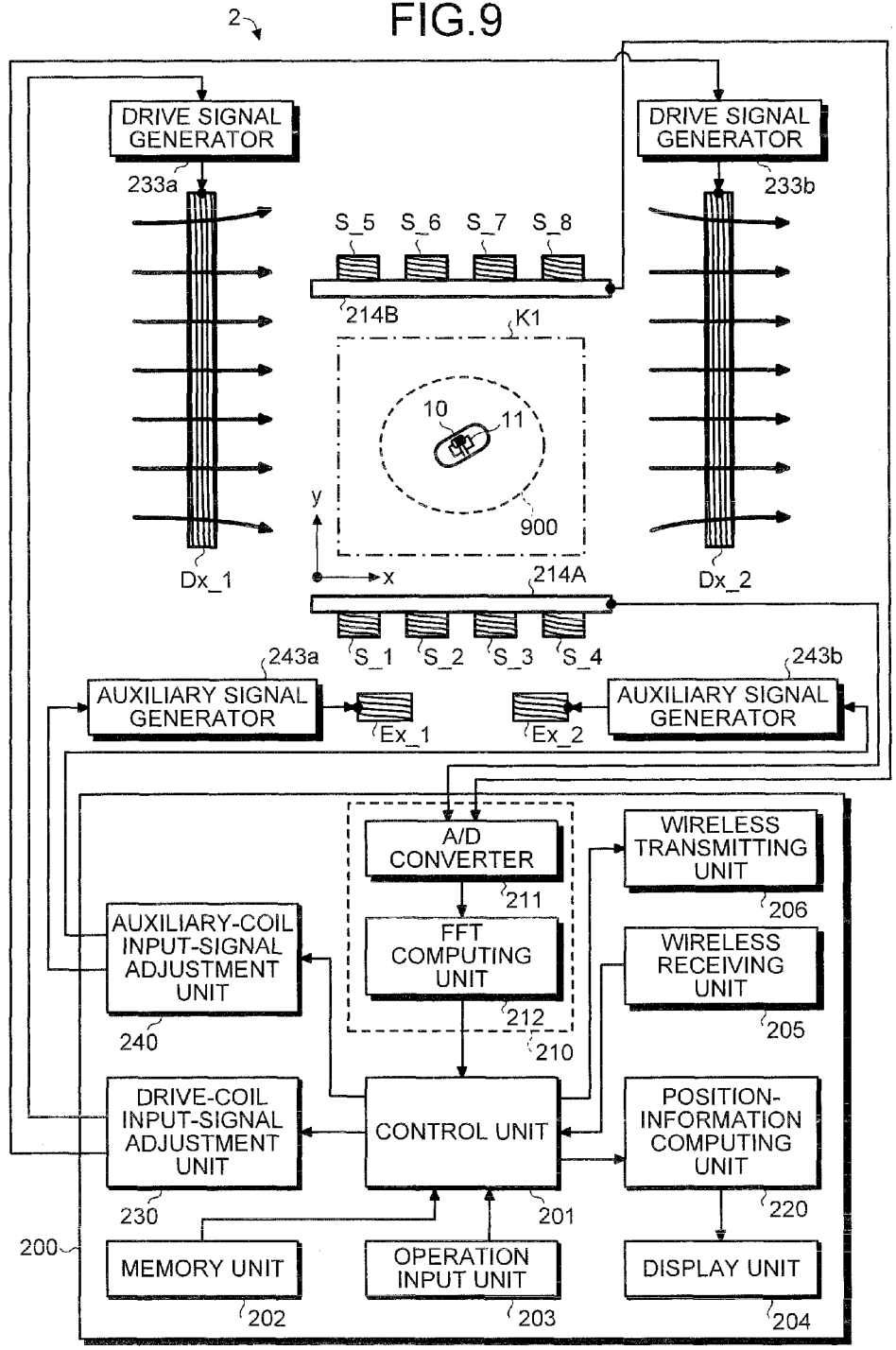

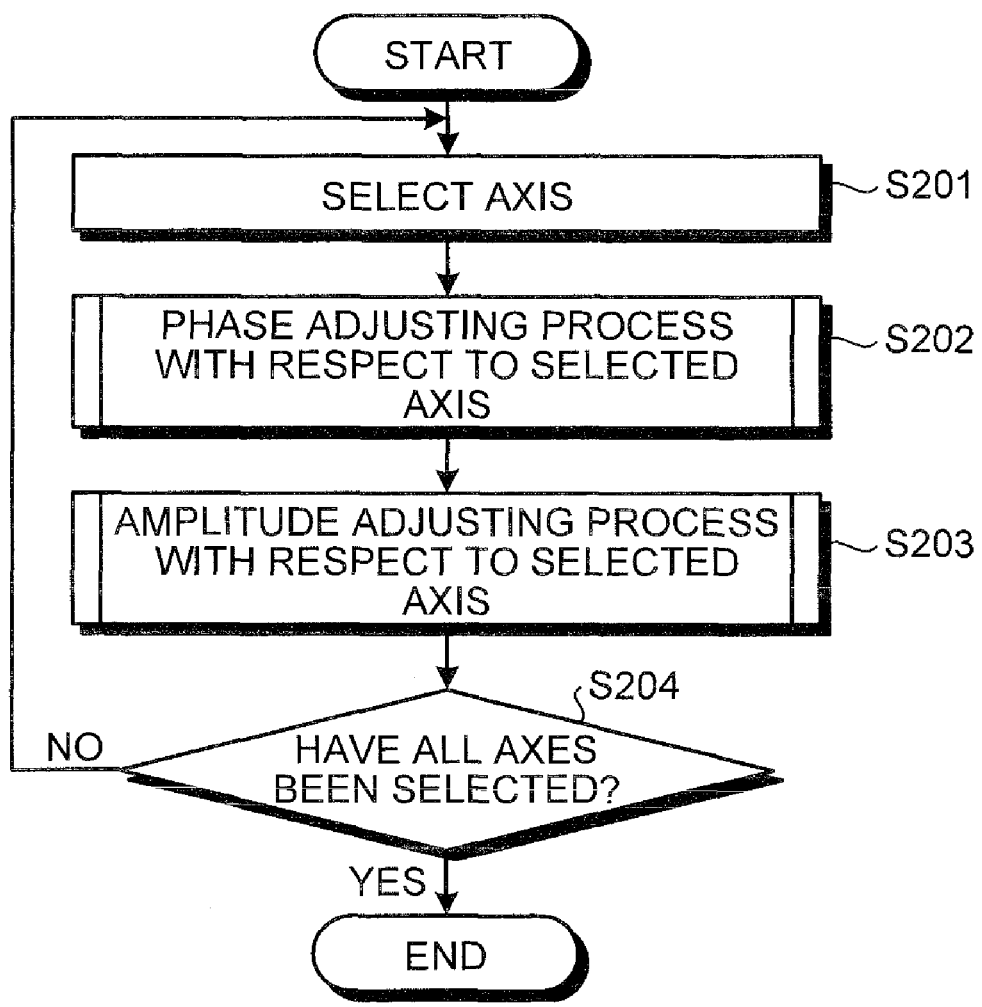

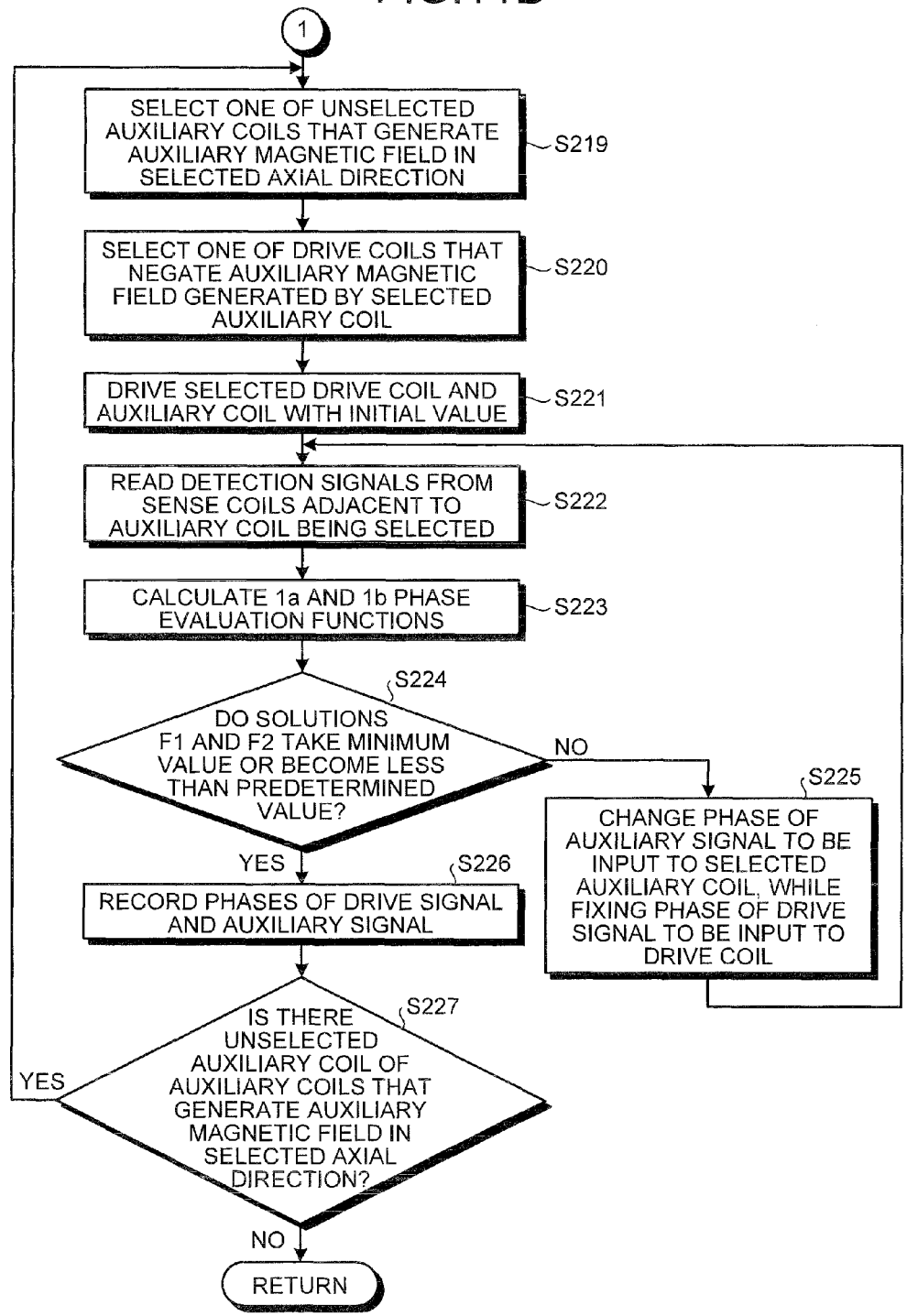

POSITION DETECTING SYSTEM AND POSITION DETECTING METHOD USING AN EVALUATION FUNCTION

CROSS-REFERENCE TO RELATED APPLICATIONS

This application is a continuation of PCT international application Ser. No. PCT/JP2010/052099 filed on Feb. 12, 2010 which designates the United States, incorporated herein by reference, and which claims the benefit of priority from Japanese Patent Application No. 2009-062978, filed on Mar. 16, 2009 and Japanese Patent Application No. 2009-107875, filed on Apr. 27, 2009, incorporated herein by reference.

BACKGROUND OF THE INVENTION

1. Field of the Invention

The present invention relates to a position detecting system and a position detecting method, and, more particularly relates to a position detecting system and a position detecting method for detecting a position of a capsule body-insertable apparatus (a detected object) inserted into a subject by using a magnetic field.

2. Description of the Related Art

In recent years, a capsule body-insertable apparatus (hereinafter, "capsule endoscope") including an imaging device has been developed. The capsule endoscope is orally inserted into a subject to capture images, and wirelessly transmits acquired images (hereinafter, "in-vivo images") to an external device disposed outside the subject. An operator can diagnose symptoms or the like of the subject by visually confirming in-vivo images received by the external device.

Generally, such a capsule endoscope cannot move in a subject by itself, and moves in the subject by peristaltic actions of the digestive system of the subject. Therefore, for example, it is inferior in observation capability as compared with an endoscope such as a fiberscope, with which an operator can select a region to observe freely to some extent.

As a technique of solving such a problem, for example, there is Japanese Laid-open Patent Publication No. 2005-245963. According to this patent document, the posture and movement of a capsule endoscope can be positively controlled from outside of a subject by applying a magnetic field (hereinafter, "guidance magnetic field") to the capsule endoscope including a magnetic field generator such as a permanent magnet from outside of the subject.

However, to control the posture and movement of the capsule endoscope in the subject by a magnetic field applied from outside of the subject, as described in Japanese Laid-open Patent Publication No. 2005-245963, the position and orientation of the capsule endoscope in the subject need to be ascertained accurately. Hereinafter, detection of the position and orientation (posture) of the capsule endoscope is simply referred to as "position detection".

In Japanese Laid-open Patent Publication No. 2005-245963, a resonant circuit including a coil (L) and a capacitor (C) (hereinafter, "LC resonant circuit") is provided in the capsule endoscope, and the LC resonant circuit detects a resonant magnetic field generated due to a magnetic field provided from outside (hereinafter, "driving magnetic field") by a sense coil provided in the external device, thereby detecting the position and orientation of the capsule endoscope. Hereinafter, a method of deriving information such as position and orientation from the resonant magnetic field generated by applying the driving magnetic field from outside to the LC resonant circuit is referred to as "passive method".

With the passive method, there is a merit that power consumption of the capsule endoscope can be suppressed.

However, in the passive method, a sense coil in the external device also detects a driving magnetic field used for inducing the LC resonant circuit, other than the resonant magnetic field emitted from the LC resonant circuit. Therefore, to detect an accurate position of the capsule endoscope, an influence of the driving magnetic field needs to be eliminated to extract only the component of the resonant magnetic field.

Generally, a phase of the resonant magnetic field emitted by the LC resonant circuit is delayed by 90° with respect to a phase of the driving magnetic field. Therefore, conventionally, to extract only the component of the resonant magnetic field, for example, the influence of the driving magnetic field generated in a state without the LC resonant circuit is detected by the sense coil in advance, and at the time of actually detecting the position of the capsule endoscope (the LC resonant circuit), a magnetic-field component of the phase delayed by 90° relative to the driving magnetic field is extracted.

SUMMARY OF THE INVENTION

A position detecting system according to an aspect of the present invention includes a detected object disposed in a detection space; and an external device disposed outside the detection space. The detected object includes a resonant circuit that generates a resonant magnetic field according to a driving magnetic field formed in the detection space. The external device includes at least two drive coils that form the driving magnetic field in the detection space; at least two drive-signal input units that input a drive signal for forming the driving magnetic field to the drive coils, respectively; at least one sense coil that detects a magnetic field formed in the detection space; a signal adjustment unit that adjusts a phase and an amplitude of the drive signal input to each of the drive coils by the drive-signal input units, based on a magnetic field detected by the sense coil; and a position deriving unit that derives a position of the detected object based on a magnetic field detected by the sense coil.

A position detecting method according to another aspect of the present invention is for detecting a position of a detected object that is inserted into a detection space where at least two drive coils that form a driving magnetic field are disposed to generate a resonant magnetic field for detecting a position of the detected object according to the driving magnetic field. The position detecting method includes detecting a magnetic field formed in the detection space by at least one sense coil provided outside the detected object, by inputting a drive signal to the drive coils in a state with the detected object not being inserted into the detection space; adjusting a phase and an amplitude of the drive signal based on the detected magnetic field; forming a driving magnetic field in the detection space by inputting the drive signal, with a phase or an amplitude thereof being adjusted, to the drive coils in a state with the detected object being inserted into the detection space; detecting a magnetic field in the detection space at a time of forming the driving magnetic field in the detection space by the at least one sense coil; and deriving a position of the detected object based on the magnetic field detected at a time of forming the driving magnetic field in the detection space.

A position detecting system according to still another aspect of the present invention includes a body-insertable apparatus disposed in a detection space in a state of being inserted into a subject; and an external device disposed outside the detection space. The body-insertable apparatus includes a resonant circuit that generates a resonant magnetic field according to a driving magnetic field formed in the detection space. The external device includes a sense coil that generates a detection signal according to a magnetic field formed in the detection space; a drive coil that generates the driving magnetic field; a driving-magnetic-field generating unit that inputs a drive signal for generating the driving magnetic field to the drive coil; an auxiliary coil that generates a auxiliary magnetic field for reducing the driving magnetic field input to the sense coil; an auxiliary-magnetic-field generating unit that inputs an auxiliary signal for generating the auxiliary magnetic field to the auxiliary coil; a phase storage unit that stores a phase of the driving magnetic field formed in the detection space in a state with the body-insertable apparatus not being inserted into the detection space; a combined-magnetic-field information storage unit that stores information of a combined magnetic field formed in the detection space, at a time of generating the driving magnetic field and the auxiliary magnetic field in a state with the body-insertable apparatus not being inserted into the detection space; a signal processor that derives information of the magnetic field from the detection signal; a position deriving unit that derives a position of the body-insertable apparatus by using information of the magnetic field derived by the signal processor, the phase stored in the phase storage unit, and information of the combined magnetic field stored in the combined-magnetic-field information storage unit; and a control unit that causes the signal processor to derive information of the magnetic field based on the detection signal read from the sense coil, in a state that the auxiliary-magnetic-field generating unit inputs the auxiliary signal to the auxiliary coil, while the driving-magnetic-field generating unit inputs the drive signal to the drive coil, and causes the position deriving unit to derive a position of the body-insertable apparatus by using the acquired information of the magnetic field, the phase stored in the phase storage unit, and information of the combined magnetic field stored in the combined-magnetic-field information storage unit.

A position detecting method according to still another aspect of the present invention is for detecting a position of a body-insertable apparatus that is disposed in a detection space where a sense coil that detects a magnetic field, a drive coil that generates a driving magnetic field, and an auxiliary coil that generates a auxiliary magnetic field for reducing the driving magnetic field input to the sense coil are disposed, to generate a resonant magnetic field for detecting a position of the body-insertable apparatus according to the driving magnetic field. The position detecting method includes detecting a phase of the driving magnetic field formed in the detection space in a state with the body-insertable apparatus not being disposed in the detection space; acquiring information of a combined magnetic field formed in the detection space at a time of generating the driving magnetic field and the auxiliary magnetic field in a state with the body-insertable apparatus not being disposed in the detection space; acquiring information of a magnetic field detected by the sense coil at a time of generating the driving magnetic field and the auxiliary magnetic field in a state with the body-insertable apparatus being disposed in the detection space; and deriving a position of the body-insertable apparatus by using the acquired information of the magnetic field detected by the sense coil, the phase, and the acquired information of the combined magnetic field.

A position detecting system according to still another aspect of the present invention includes a detected object disposed in a detection space; and an external device disposed outside the detection space. The detected object includes a resonating means for generating a resonant magnetic field according to a driving magnetic field formed in the detection space. The external device includes at least two driving means for forming the driving magnetic field in the detection space; at least two drive-signal inputting means for inputting a drive signal for forming the driving magnetic field, respectively, to the driving means; at least one detecting means for detecting a magnetic field formed in the detection space; a signal adjusting means for adjusting a phase and an amplitude of the drive signal input to each of the driving means by the drive-signal inputting means, based on a magnetic field detected by the detecting means; and a position deriving means for deriving a position of the detected object based on a magnetic field detected by the detecting means.

A position detecting system according to still another aspect of the present invention includes a body-insertable apparatus disposed in a detection space in a state of being inserted into a subject; and an external device disposed outside the detection space. The body-insertable apparatus includes a resonating means for generating a resonant magnetic field according to a driving magnetic field formed in the detection space. The external device includes a detecting means for generating a detection signal according to a magnetic field formed in the detection space; a driving means for generating the driving magnetic field; a driving-magnetic-field generating means for inputting a drive signal for generating the driving magnetic field to the driving means; an auxiliary means for generating an auxiliary magnetic field for reducing the driving magnetic field input to the detecting means; an auxiliary-magnetic-field generating means for inputting an auxiliary signal for generating the auxiliary magnetic field to the auxiliary means; a phase storing means for storing a phase of the driving magnetic field formed in the detection space in a state with the body-insertable apparatus not being inserted into the detection space; a combined-magnetic-field information storing means for storing information of a combined magnetic field formed in the detection space, at a time of generating the driving magnetic field and the auxiliary magnetic field in a state with the body-insertable apparatus not being inserted into the detection space; a signal processing means for deriving information of the magnetic field from the detection signal; a position deriving means for deriving a position of the body-insertable apparatus by using information of the magnetic field derived by the signal processing means, the phase stored in the phase storing means, and information of the combined magnetic field stored in the combined-magnetic-field information storing means; and a controlling means for causing the signal processor to derive information of the magnetic field based on the detection signal read by the detecting means, in a state that the auxiliary-magnetic-field generating means inputs the auxiliary signal to the auxiliary means, while the driving-magnetic-field generating means inputs the drive signal to the driving means, and causes the position deriving means to derive a position of the body-insertable apparatus by using the acquired information of the magnetic field, the phase stored in the phase storing means, and information of the combined magnetic field stored in the combined-magnetic-field information storing means.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a schematic diagram of a schematic configuration of a position detecting system according to the second embodiment of the present invention;

FIG. 10 is a flowchart of a schematic flow of a drive-signal and auxiliary-signal adjustment operation according to the second embodiment of the present invention;

FIGS. 11A and 11B are flowcharts of a flow of a phase adjusting process according to the second embodiment of the present invention;

DETAILED DESCRIPTION OF THE PREFERRED EMBODIMENTS

Exemplary embodiments of a position detecting system and a position detecting method according to the present invention will be explained below in detail with reference to the accompanying drawings. The present invention is not limited to the embodiments.

First Embodiment

Configurations and operations of a position detecting system 1 according to a first embodiment of the present invention are explained in detail with reference to the drawings. The present embodiment realizes a position detecting system and a position detecting method capable of accurately detecting a position of a detected object by generating an optimum driving magnetic field without relying on apparatus characteristics.

Configuration of Position Detection

Figure 1:
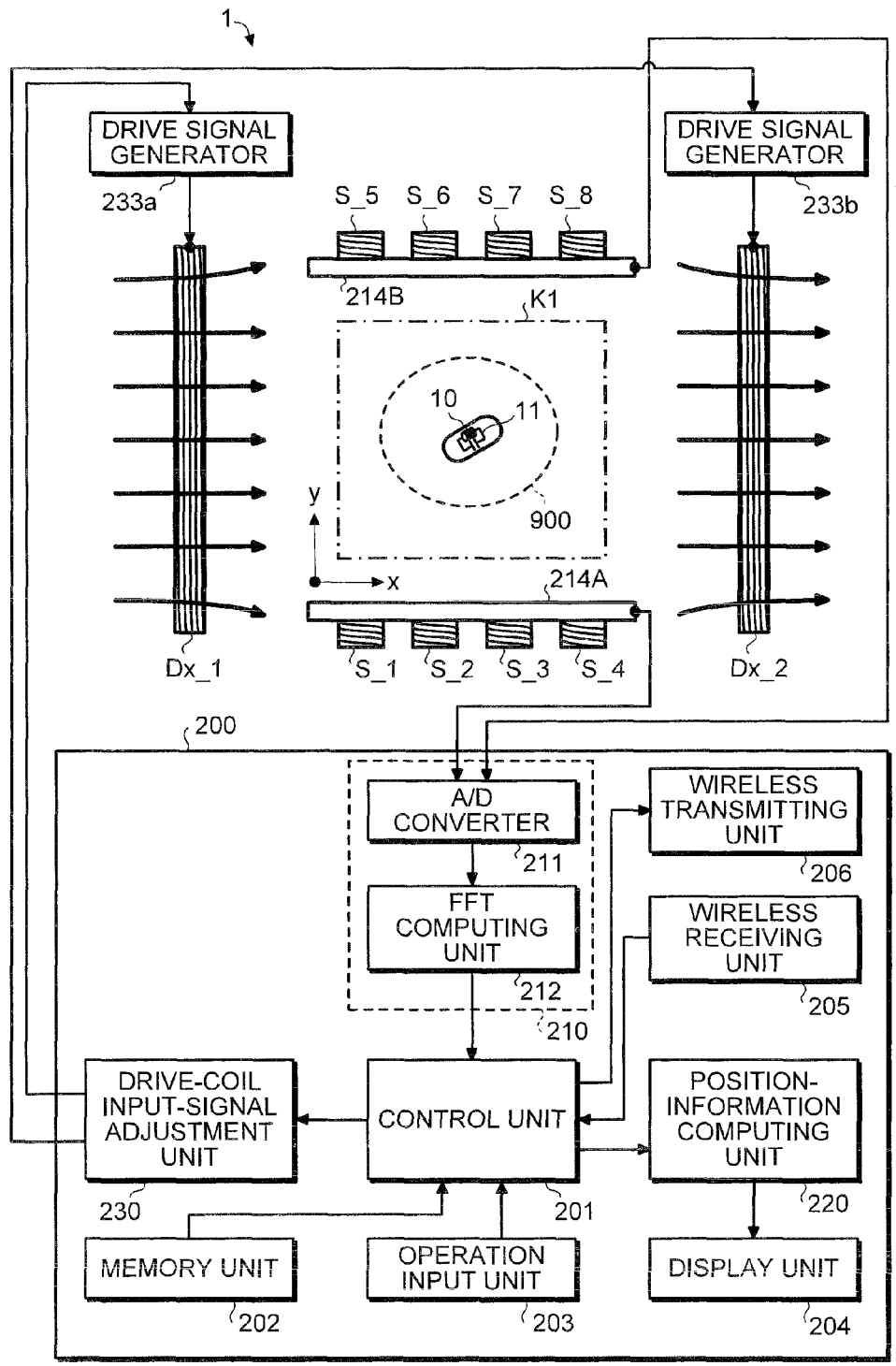
FIG. 1 is a schematic diagram of a schematic configuration of a position detecting system according to a first embodiment of the present invention.

FIG. 1 is a schematic diagram of a schematic configuration of the position detecting system 1 according to the present embodiment. As shown in FIG. 1, the position detecting system 1 includes a detection space K1 for accommodating a subject 900 into which an LC marker 10 is inserted as a detected object, and an external device 200 that detects the position and orientation (posture) of the LC marker 10 in the detection space K1.

LC Marker

Figure 2:
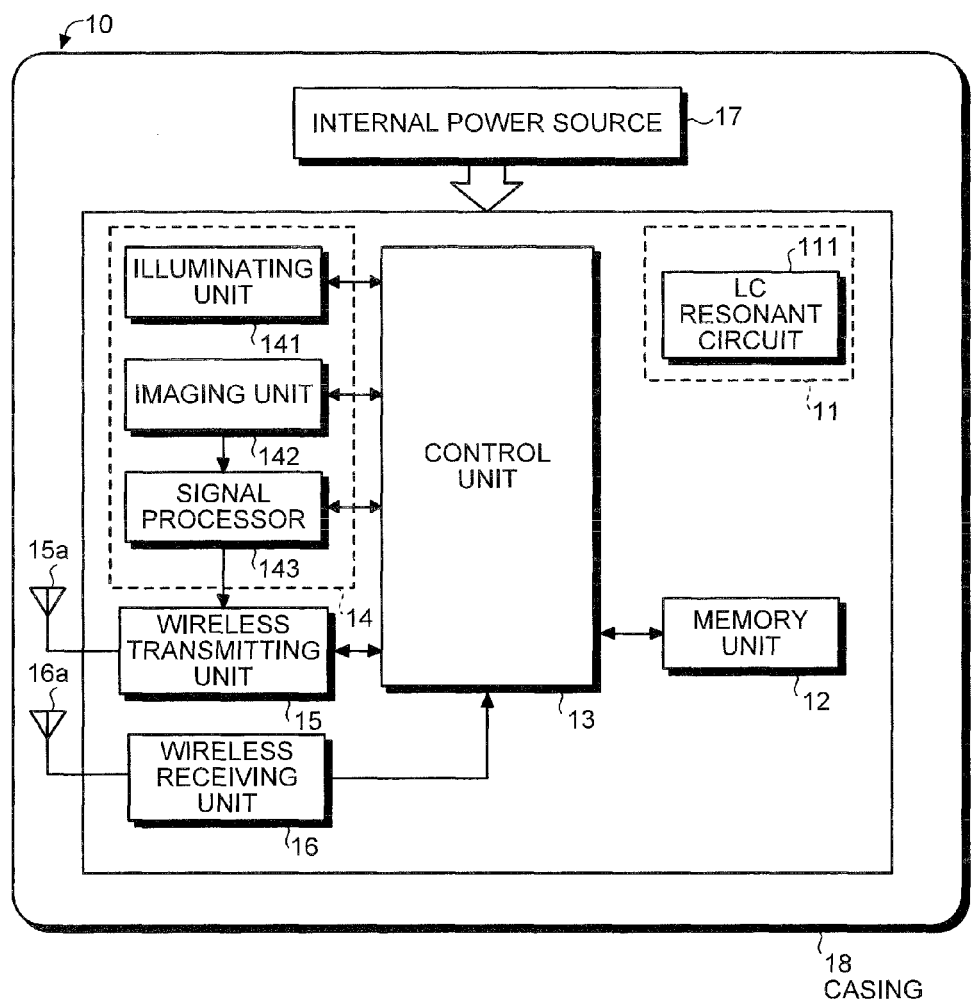
FIG. 2 is a block diagram of a schematic configuration example of an LC marker according to the first embodiment or a second embodiment of the present invention.

As shown in FIG. 2, the LC marker 10 includes a resonant-magnetic-field generating unit 11 that generates a resonant magnetic field for position detection. The resonant-magnetic-field generating unit 11 includes an LC resonant circuit 111 including a capacitor (C) and an inductor (L) connected in parallel, and is excited by a magnetic field for position detection (hereinafter, "driving magnetic field") of a frequency substantially equal to resonant frequency F0 input from outside, to generate a resonant magnetic field. The resonant frequency F0 is a resonant frequency of the LC resonant circuit 111 determined by the capacitor (C) and the inductor (L) connected in parallel.

The LC marker 10 can include a function as, for example, a capsule medical apparatus. In this case, as shown in FIG. 2, the LC marker 10 includes, for example, a control unit 13 that controls respective units in the LC marker 10, an in-vivo information acquiring unit 14 that acquires various pieces of information in the subject 900, a wireless transmitting unit 15 and a transmitting antenna 15a for transmitting in-vivo information acquired by the in-vivo information acquiring unit 14 to outside of the LC marker 10 as a wireless signal, a wireless receiving unit 16 and a receiving antenna 16a for receiving various operation instructions and the like transmitted from the external device 200 as a wireless signal, and an internal power source 17 that supplies power to the respective units in the LC marker 10. FIG. 2 is a block diagram of a schematic configuration example of the LC marker 10 according to the present embodiment.

The in-vivo information acquiring unit 14 includes an imaging unit 142 that acquires, for example, in-vivo images as in-vivo information, an illuminating unit 141 that illuminates inside of the subject 900 at the time of capturing an image of the subject 900 by the imaging unit 142, and a signal processor 143 that performs predetermined signal processing with respect to the in-vivo image acquired by the imaging unit 142.

Figure 3:
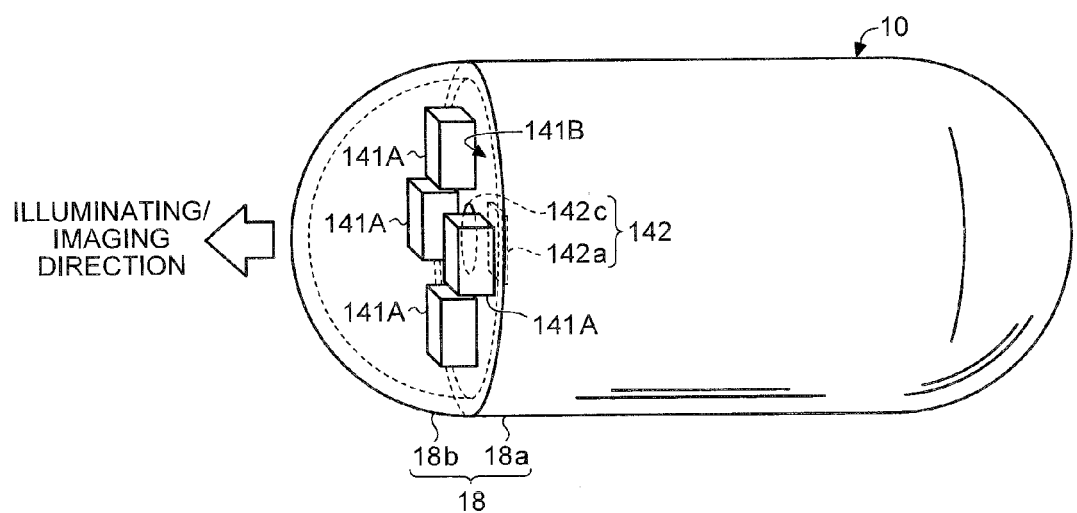
FIG. 3 is an external view of a schematic configuration example of the LC marker according to the first embodiment, the second embodiment, or a fourth embodiment of the present invention.

For example, as shown in FIG. 3, the imaging unit 142 includes an image pickup device 142a that converts incident light to an electric signal to form an image, an objective lens 142c disposed on a receiving surface side of the image pickup device 142a, and an image-pickup-device drive circuit (not shown) that drives the image pickup device 142a. FIG. 3 is an external view of a schematic configuration example of the LC marker 10 according to the present embodiment.

As shown in FIG. 3, for example, a CCD (Charge Coupled Device) camera or a CMOS (Complementary Metal Oxide Semiconductor) camera can be used for the image pickup device 142a. The image-pickup-device drive circuit drives the image pickup device 142a to acquire in-vivo images as an analog signal under control of the control unit 13. The image-pickup-device drive circuit outputs the in-vivo images in the analog signal read from the image pickup device 142a to the signal processor 143.

As shown in FIG. 3, the illuminating unit 141 includes a plurality of light sources 141A, and a light-source drive circuit (not shown) that drives the respective light sources 141A. For example, an LED (Light Emitting Diode) can be used as the respective light sources 141A. The light-source drive circuit illuminates inside of the subject 900 by driving the light sources 141A, matched with driving of the imaging unit 142 under control of the control unit 13.

Explanations are continued while referring back to FIG. 2. The signal processor 143 performs predetermined signal processing such as sampling, amplification, and A/D (Analog to Digital) conversion with respect to the analog in-vivo image input from the imaging unit 142 to generate a digital in-vivo image. The in-vivo image having undergone various types of processing is input to the wireless transmitting unit 15.

The in-vivo information acquiring unit 14 can include a sensor element (not shown) and a sensor-element drive circuit that controls drive of the sensor element. The sensor element includes, for example, a thermometer, a pressure gauge, and a pH meter, to appropriately acquire temperature, pressure, and pH level in the subject 900 as the in-vivo information. The sensor-element drive circuit drives the sensor element to acquire the in-vivo information under control of the control unit 13, and inputs the in-vivo information to the wireless transmitting unit 15.

The wireless transmitting unit 15 is connected to the transmitting antenna 15a constituted by a coil antenna or the like, to perform various types of processing such as superposition on a reference frequency signal for transmission, modulation, and up-conversion with respect to the in-vivo information such as the in-vivo image input from the signal processor 143, and then transmits the in-vivo image as a wireless signal from the transmitting antenna 15a to the external device 200.

The wireless receiving unit 16 is connected to the receiving antenna 16a constituted by a coil antenna or the like, and receives various operation instructions and the like transmitted as the wireless signal from the external device 200 via the receiving antenna 16a, performs various types of processing such as filtering, down-conversion, demodulation, and decoding with respect to the received signal, and then outputs the signal to the control unit 13.

The control unit 13 is constituted by, for example, a CPU (Central Processing Unit) or an MPU (Micro Processing Unit), and performs programs and parameters read from a storage unit (not shown) based on the various operation instructions and the like input from the external device 200 via the wireless receiving unit 16, to control the respective units in the LC marker 10.

A memory unit 12 is constituted by, for example, a RAM (Random Access Memory) and a ROM (Read Only Memory), and holds programs and parameters to be performed at the time of controlling the respective units by the control unit 13. The in-vivo information such as the in-vivo images acquired by the in-vivo information acquiring unit 14 is appropriately stored in the memory unit 12.

The internal power source 17 includes a button battery, which is, for example, a primary battery or a secondary battery, and a power source circuit that raises pressure of power output from the button battery and supplies the power to the respective units in the LC marker 10, to supply driving electric power to the respective units in the LC marker 10. However, the power source is not limited to the button battery.

The respective units (11, 13, 14, 15, 15a, 16, 16a, and 17) are accommodated in, for example, a capsule casing 18. For example, as shown in FIG. 3, the casing 18 includes a container 18a having a substantially cylindrical or semi-elliptical spherical shape with one end having a hemispherical dome shape and the other end being opened, and a cap 18b having a hemispherical shape that is fitted to an opening of the container 18a to seal the casing 18. The casing 18 has a size, for example, that can be swallowed by the subject 900. In the present embodiment, at least the cap 18b is made of a transparent material. The light source 141A is mounted on a circuit board 141B having a light-source drive circuit (not shown) on board. Likewise, the image pickup device 142a and the objective lens 142c are mounted on a circuit board (not shown) having an image-pickup-device drive circuit (not shown) on board. The circuit board 141B mounted with the light source 141A and the circuit board mounted with the image pickup device 142a are disposed on the transparent cap 18b side in the casing 18. At this time, a device mounting surface of each circuit board is directed toward the cap 18b side. Therefore, an imaging direction of the image pickup device 142a and an illuminating direction of the light source 141A are, as shown in FIG. 3, directed outward of the LC marker 10 via the transparent cap 18b.

Detection Space

Explanations are continued while referring back to FIG. 1. Drive coils Dx_1 and Dx_2 (hereinafter, D is denoted as the reference character of an arbitrary drive coil) that form a substantially uniform driving magnetic field in the detection space K1, a plurality of sense coils S_1 to S_8 (hereinafter, S is denoted as the reference character of an arbitrary sense coil) that detect the resonant magnetic field generated by the LC resonant circuit 111 in the LC marker 10, and circuit boards 214A and 214B respectively mounted with the plurality of sense coils S_1 to S_4 and S_5 to S_4 are disposed in the detection space K1. The circuit board 214A is installed, for example, below a table (not shown) on which the subject 900 having the LC marker 10 inserted therein is lying, and the circuit board 214B is disposed, for example, above the detection space K1.

The drive coils Dx_1 and Dx_2 opposite to each other, putting the detection space K1 therebetween, form a pair, and generate, for example, a substantially uniform driving magnetic field constituted by magnetic field lines extending in a direction of an x-axis in the detection space K1. A pair of drive coils D (not shown) that generates the substantially uniform driving magnetic field constituted by magnetic field lines extending in a direction different from the x-axis (for example, in a direction of a y-axis or a direction (of a z-axis) orthogonal to the x-axis and the y-axis in the detection space K1 is separately provided near the detection space K1. By changing over the drive coils D to be driven in the plurality of pairs of the drive coils D according to the position and orientation of the LC marker 10, a resonant magnetic field can be generated with a stable intensity in the LC resonant circuit 111, even if the LC resonant circuit 111 in the LC marker 10 (particularly, inductor (L)) turns to any direction in the detection space K1. As a result, position detection accuracy of the LC marker 10 can be improved.

The respective sense coils S are, respectively, magnetic sensors including a coil capable of detecting, for example, a field intensity in the y-axis direction and the direction. However, the sense coils S are not limited thereto, and can be formed by using a magnetic sensor including, for example, a magnetoresistive element and a magnetic impedance element (MI element). Further, the respective sense coils S can be constituted by a 3-axis magnetic sensor including three coils for detecting the x-axis, y-axis, and z-axis, respectively.

The sense coils S are disposed at positions insusceptible to the driving magnetic field and capable of easily detecting the resonant magnetic field generated by the LC resonant circuit 111. In the present embodiment, an example in which the sense coils S_1 to S_4 are two-dimensionally disposed on a bottom face of the circuit board 214A disposed below the detection space K1 (on an x-y plane below the detection space K1), and the sense coils S_5 to S_8 are two-dimensionally disposed on an upper face of the circuit board 214B disposed above the detection space K1 (on an x-y plane above the detection space K1) is shown.

External Device

The external device 200 includes a drive-coil input-signal adjustment unit 230 that adjusts the amplitude and phase of a signal used for driving the drive coil D (hereinafter, "drive signal"), drive signal generators (hereinafter, also "drive-signal input units") 233a and 233b that generate a drive signal to be input to drive coils Dx_1 and Dx_2, respectively, according to the control from the drive-coil input-signal adjustment unit 230 (hereinafter, 233 is denoted as the reference character of an arbitrary drive signal generator), a magnetic-field-information acquiring unit 210 that acquires information of the magnetic field (hereinafter, "magnetic field information") included in a detection signal from a voltage change read from the sense coil S (hereinafter, "detection signal"), a position-information computing unit 220 that derives the position and orientation of the LC marker 10 based on the magnetic field information acquired by the magnetic-field-information acquiring unit 210, a control unit 201 that controls respective units in the external device 200, a memory unit 202 that stores various programs to be executed at the time of controlling the respective units by the control unit 201, parameters and the like, an operation input unit 203 for an operator to input various operation instructions to the LC marker 10, a display unit 204 that displays the position and orientation of the LC marker 10 and in-vivo information acquired from the LC marker 10 by images (including video pictures) and sounds, a wireless receiving unit 205 that receives the in-vivo information and the like transmitted from the LC marker 10 as a wireless signal, and a wireless transmitting unit 206 that transmits various operation instructions such as an imaging instruction to the LC marker 10 as a wireless signal. In FIG. 1, a configuration in which the drive signal generators 233a and 233b are separately provided from the external device 200 is explained as an example; however, the present invention is not limited thereto, and the drive signal generators 233a and 233b can be provided in the external device 200.

The control unit 201 is constituted by, for example, a CPU or an MPU, and controls the respective units in the external device 200 according to the program and parameter read from the memory unit 202. The memory unit 202 is constituted by, for example, a RAM or a ROM, and holds the programs to be executed at the time of controlling the respective units by the control unit 201 and parameters. The in-vivo image received from the LC marker 10 and information such as the position and orientation of the LC marker 10 derived by the position-information computing unit 220 are appropriately stored in the memory unit 202.

The operation input unit 203 includes, for example, a keyboard, a mouse, a numerical keypad, and a joystick, so that an operator inputs various operation instructions with respect to the LC marker 10 such as an imaging instruction (including an in-vivo information acquiring instruction or the like), and various operation instructions with respect to the external device 200 such as a screen switching instruction for switching a screen for display on the display unit 204. When the LC marker 10 includes a plurality of the imaging units 142 and images acquired by the LC marker 10 are displayed on the display unit 204 on a real-time basis, a screen switching function for display on the display unit 204 can be provided.

The display unit 204 is a display device such as a liquid crystal display, a plasma display, or LED array, and displays information such as the position and orientation of the LC marker 10 or in-vivo information such as in-vivo images transmitted from the LC marker 10. The display unit 204 can have a sound reproduction function using a speaker or the like. The display unit 204 notifies the operator by sounds of various pieces of operation guidance and information such as a remaining amount of battery of the LC marker 10 (including an alarm or the like) by using the sound reproduction function.

The wireless receiving unit 205 is connected to a receiving antenna (not shown) such as a dipole antenna disposed adjacent to the detection space K1. For example, the receiving antenna is disposed near the detection space K1. The wireless receiving unit 205 receives the in-vivo image and the like transmitted from the LC marker 10 as a wireless signal via the receiving antenna, performs various types of processing such as filtering, down-conversion, demodulation, and decoding with respect to the received signal, and then outputs the signal to the control unit 201.

The wireless transmitting unit 206 is connected to a transmitting antenna (not shown) constituted by a dipole antenna disposed adjacent to the detection space K1. For example, the transmitting antenna is disposed near the detection space K1. The wireless transmitting unit 206 performs various types of processing such as superposition on the reference frequency signal for transmission, modulation, and up-conversion with respect to signals such as various operation instructions with respect to the LC marker 10 input from the control unit 201, and transmits the signals from the transmitting antenna to the LC marker 10 as radio signals.

The drive-coil input-signal adjustment unit 230, the drive signal generator 233, and the drive coils D in FIG. 1 function as a mechanism for generating the driving magnetic field in the detection space K1 (hereinafter, "driving system").

The drive-coil input-signal adjustment unit 230 calculates a signal waveform of a frequency substantially equal to the resonant frequency F0 of the LC resonant circuit 111 in the LC marker 10 according to a control signal input from the control unit 201, and outputs the signal waveform to the drive signal generators 233a and 233b. The signal waveform input to the drive signal generator 233a and the signal waveform input to the drive signal generator 233b can be different from each other.

The drive signal generator 233 generates a drive signal according to the signal waveform input from the drive-coil input-signal adjustment unit 230 and amplifies the current thereof, and then inputs the amplified drive signal to the drive coil D. The drive coil D, to which the amplified drive signal is input, forms a driving magnetic field that excites the LC resonant circuit 111 in the detection space K1 by generating a magnetic field of a frequency substantially equal to the resonant frequency F0 of the LC resonant circuit 111 in the LC marker 10.

The magnetic-field-information acquiring unit 210 and the control unit 201 in FIG. 1 function as a mechanism for detecting a magnetic field in which the driving magnetic field formed by the driving system and the resonant magnetic field generated by the LC marker 10 are combined (hereinafter, "detecting system").

The magnetic-field-information acquiring unit 210 derives information of the magnetic field included in the detection signal (hereinafter, "magnetic field information") substantially on a real-time basis by performing predetermined processing with respect to the detection signal read from the sense coil S. The magnetic-field-information acquiring unit 210 includes, for example, an A/D converter 211 and an FFT computing unit 212. The A/D converter 211 reads the detection signal respectively from plural sense coils S, and appropriately performs amplification, band limiting, and A/D conversion with respect to the read analog detection signal. The FFT computing unit 212 generates data indicating the magnetic field information (hereinafter, "FFT data") by performing fast Fourier transform on the digital detection signal output from the A/D converter 211, and inputs the data to the control unit 201. The control unit 201 inputs the input FFT data to the position-information computing unit 220.

The position-information computing unit 220 derives the current position and orientation of the LC marker 10 based on the magnetic field information included in the detection signal by performing predetermined arithmetic processing with respect to the FFT data input via the control unit 201. The detection signals read from the respective sense coil S are signals in which magnetic field information such as an intensity and a phase of the magnetic field at the positions where the respective sense coils S are disposed is expressed by voltage levels. The FFT data is data in which magnetic field information included in the detection signal read from the sense coils S is converted to information including an intensity component and a phase component.

However, the detection signals read from the respective sense coils S include information of the driving magnetic field of a frequency substantially equal to the resonant frequency F0 and a magnetic field induced and generated in the drive coil D by the resonant magnetic field (hereinafter, "driving magnetic field"), other than the resonant magnetic field generated by the LC resonant circuit 111. Therefore, the position-information computing unit 220 cannot derive the accurate position and orientation of the LC marker 10 (particularly, the LC resonant circuit 111) directly from the FFT data generated by the detection signals read from the respective sense coils S.

Figure 4:
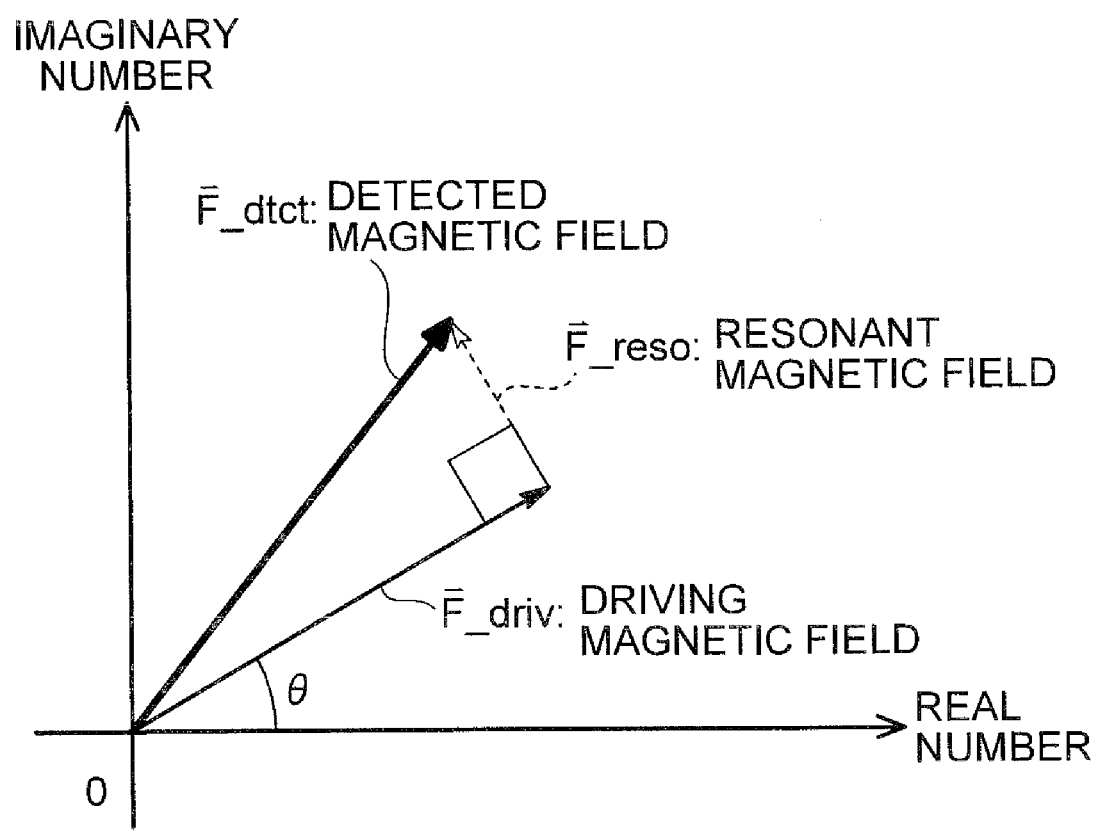
FIG. 4 depicts a relation among a driving magnetic field, a detection magnetic field, and a resonant magnetic field in the first embodiment of the present invention.

As shown in FIG. 4, the resonant magnetic field generated by the LC marker 10 (hereinafter, a vector of the resonant magnetic field expanded in a planar space indicating an intensity and a phase is referred to as "F_reso") has 90-degree phase difference with respect to the driving magnetic field (hereinafter, a vector of the driving magnetic field expanded in the planar space indicating an intensity and a phase is referred to as "F_drive"). Therefore, to extract the resonant magnetic field F_reso by removing the driving magnetic field F_drive from full magnetic field included in the FFT data (hereinafter, "detection magnetic field", and a vector of the detection magnetic field expanded in the planar space indicating an intensity and a phase is referred to as "F_dtct"), a vector component having 90-degree phase difference with respect to the driving magnetic field F_drive needs to be extracted from the detection magnetic field F_dtct. FIG. 4 depicts a relation among the driving magnetic field, the detection magnetic field, and the resonant magnetic field in the present embodiment.

Therefore, in the present embodiment, before performing actual position detection, the drive coils D are driven in a state with the LC marker 10 (that is, the LC resonant circuit 111) not being inserted into the detection space K1 to form the driving magnetic field in the detection space K1, and a phase component of the driving magnetic field F_drive (hereinafter, "calibration information") detected by the sense coils S and a magnetic field sensor (not shown) disposed in the detection space K1 is actually derived by using, for example, the magnetic-field-information acquiring unit 210 and the control unit 201. Further, the derived calibration information is held in an LUT (Look Up Table) or the like in association with information of an amplitude value and phase of the drive signal at the time of generating the driving magnetic field. In a position detecting process described later, the position-information computing unit 220 refers to the LUT to acquire the phase of the driving magnetic field F_drive to be removed from the detection magnetic field F_dtct, and the FFT data is corrected based on the phase thereby extracting the resonant magnetic field F_reso. Hereinafter, the process of removing the driving magnetic field F_drive from the detection magnetic field F_dtct is referred to as "calibration process".

Further, the detection magnetic field F_dtct includes, as an unnecessary magnetic field, a magnetic field (hereinafter, "interference magnetic field") generated because the coils (the drive coils D and the like) disposed near the detection space K1 are interfered by the resonant magnetic field generated by the LC resonant circuit 111. Therefore, in the present embodiment, a process of removing the interference magnetic field is performed according to the position and orientation derived by using the resonant magnetic field F_reso (FFT data). This process is referred to as "correcting process".

The correcting process includes, for example, a method in which correction amounts according to the position and orientation are registered in the LUT in advance, and a method in which correction parameters according to the position and orientation are registered in the LUT in advance.

In the method in which the correction amount is registered in the LUT in advance, for example, the information of the interference magnetic field generated by the respective drive coils D (FFT data) is acquired in advance by a simulation or an actual measurement. Further, to perform a simulation, a current detector that detects current flowing in the respective drive coils D is provided, and a simulation can be performed by using the current value detected by the current detector. The acquired information is managed by the LUT or the like as the correction amount, in association with the position and orientation. In the correcting process at the time of position detection, the LUT is referred to by using the position and orientation derived in advance to acquire the correction amount corresponding to the position and orientation, and the FFT data is corrected by using the correction amount, thereby deriving new position and orientation of the LC marker 10 by using the corrected FFT data.

For example, convergence calculation using a least-square method can be used for the position detecting process of the LC marker 10 including the correcting process. In the convergence calculation, it is assumed that the FFT data to be processed (corresponding to the first FFT data calculated from the detection signal or corrected FFT data described later) is a true value, and the FFT data in an ideal magnetic field distribution formed by the LC marker 10 at the position and orientation derived in advance and an equivalent magnetic moment is an estimate value. In the convergence calculation, further, the position and orientation of the LC marker 10 (for example, corresponding to the position and orientation derived in advance) is derived from the FFT data directly calculated from the detection signal though the calibration process, and the FFT data is corrected based on the correction amount associated with the position and orientation. Thereafter, the FFT data is corrected again based on the correction amount associated with the position and orientation derived from the corrected FFT data to repeat the calculation for deriving the new position and orientation from the corrected FFT data (iterative calculation). The iterative calculation is continued until a difference between the true value and the estimate value obtained by the least-square method is stabilized at a certain level. Accordingly, the position and orientation are finally derived with the accuracy being improved further. The finally derived position and orientation are displayed on the display unit 204 together with the information such as the in-vivo images received from the LC marker 10.

An operator can input an operation instruction for operating the position and orientation of the LC marker 10 by using the operation input unit 203. The operator can also input an acquisition instruction of the in-vivo information to the LC marker 10 by using the operation input unit 203.

Position Detection Operation

A position detection operation of the position detecting system 1 according to the present embodiment is explained next in detail. As described above, in the present embodiment, the drive signal generator 233 outputs the drive signal to generate the driving magnetic field by the drive coils D, so that the LC marker 10 generates the resonant magnetic field. The resonant magnetic field is detected as well as other magnetic fields of the resonant frequency F0 by the sense coils S as a detection signal. The detection signals read from the respective sense coils S are converted to the FFT data indicating the information of the detected magnetic field. The position detecting process including the calibration process and the correcting process is performed by using the FFT data, thereby deriving the position and orientation of the LC marker 10.

At this time, because a resolution with respect to the detection signal can be increased with an increase in the intensity of the resonant magnetic field generated by the LC marker 10, the position detection accuracy can be improved. However, if the intensity of the driving magnetic field is set too high for increasing the intensity of the resonant magnetic field, the detection signal read from the sense coil S is saturated with respect to a dynamic range with respect to the sense coil S and a dynamic range in the detecting system, and position detection itself becomes impossible. Therefore, in the present embodiment, the intensity of the driving magnetic field is adjusted to a level sufficient to acquire a high resolution without saturating the detection signal read from the sense coil S.

When there is a deviation in phase of the magnetic field generated by the drive coils D driven simultaneously (for example, drive coils Dx_1 and Dx_2), the intensity and phase of the driving magnetic field formed in the detection space K1 departs from the targeted intensity and phase of the driving magnetic field. Therefore, in the present embodiment, the phases of the magnetic field generated by the drive coils D driven simultaneously are aligned. Accordingly, the appropriate driving magnetic field can be formed in the detection space K1, and as a result, the position detection accuracy can be improved.

Adjustment of the intensity and phase of the driving magnetic field is performed, for example, in the drive-coil input-signal adjustment unit 230 (see FIG. 1). That is, the driving magnetic field is adjusted by controlling an amplitude value of the signal waveform of the drive signal generated by the drive-coil input-signal adjustment unit 230. Further, the phase of the magnetic field generated by the drive coils D driven simultaneously is adjusted by controlling the phase of the signal waveform simultaneously input to the drive signal generators 233 by the drive-coil input-signal adjustment unit 230.

Adjustment of the intensity and phase of the driving magnetic field can be performed by using, for example, an evaluation function described later. An adjusting method of the evaluation function and the intensity and phase of the driving magnetic field according to the present embodiment is explained in detail with reference to the drawings. A case that the number of the sense coils S is eight (S_1 to S_8), number of sets of the drive coils D is one (Dx_1 and Dx_2), and the sense coils S and the drive coils D are respectively disposed as shown in FIG. 1 is explained. However, the present invention is not limited thereto, and these numbers can be appropriately changed.

At the time of setting the evaluation function according to the present embodiment, it is assumed that voltage values of the detection signals read from the respective sense coils S_1 to S_8 are VS_1 to VS_8. The voltage values VS_1 to VS_8 are parameters used for the evaluation function. In the voltage values VS_1 to VS_8, it is assumed that an in-phase voltage value is positive, and a reversed-phase voltage value is negative with respect to the phase of the voltage value VS_1.

Phase Adjustment

A flow for adjusting the phase of the drive signal respectively input to the drive coils D x_1 and Dx_2 driven simultaneously is explained. A total value (a solution F) of absolute values of the intensity of the driving magnetic fields detected by the respective sense coils S can be expressed by the following Equation (1) by using the parameters described above.

$$F = |VS\_1| + |VS\_2| + |VS\_3| + |VS\_4| + |VS\_5| + |VS\_6| + |VS\_7| + |VS\_8| \quad (1)$$

Because the magnetic fields respectively generated by the drive coils Dx_1 and Dx_2 negate each other on the respective surfaces of the sense coils S, the solution F decreases as the phases of the magnetic fields respectively generated by the drive coils Dx_1 and Dx_2 are aligned, and when the phases of the two magnetic fields are aligned completely, the solution F becomes minimum. Therefore, in the present embodiment, Equation (1) is used as an evaluation function for phase adjustment (hereinafter, "phase evaluation function").

In the phase adjustment, the phase of the drive signal to be input to the respective drive coils Dx_1 and Dx_2 is adjusted so that an evaluation function for phase evaluation expressed by Equation (1) takes a minimum value or becomes lower than a predetermined value set in advance. For example, the phase of the drive signal to be input to the drive coil Dx_1 is fixed, and the phase of the drive signal to be input to the drive coil Dx_2 is adjusted, thereby aligning the phases of the driving magnetic fields generated by the respective drive coils Dx_1 and Dx_2. Adjustment of the phase of the drive signals is preferably performed with a value at which the voltage values VS_1 to VS_8 are not saturated. The drive signal with the phase being fixed can be the drive signal to be input to the drive coil Dx_2.

Amplitude Adjustment

A flow for adjusting the amplitude of the drive signals to be input respectively to the drive coils Dx_1 and Dx_2 driven simultaneously is explained next. A voltage value at which the sense coil S is saturated is referred to as "saturation voltage value", and a case that the amplitude of the drive signal is adjusted so that the voltage values VS_1 to VS_8 acquired by the respective sense coils S_1 to S_8 are not saturated, by adjusting the amplitude of the drive signal while using a predetermined rate (for example, 90%) of the saturation voltage value as a reference voltage value VSmax is explained.

In the amplitude adjustment according to the present embodiment, for example, the following Equation (2) is used as an evaluation function for amplitude adjustment (hereinafter, "amplitude evaluation function"). In Equation (2), A denotes a solution acquired by the amplitude evaluation function, and VSmax denotes the reference voltage value.

$$A = |VSmax - |VS\_1|| + |VSmax - |VS\_5|| + |VSmax - |VS\_4|| + |VSmax - |VS\_8|| + \frac{1}{|VS\_1|} + \frac{1}{|VS\_2|} + \ldots + \frac{1}{|VS\_8|} \quad (2)$$

The above equation (2) represents a function for adding the sum of reciprocal numbers of the voltage values VS_1 to VS_8 of detection signals read from the respective sense coils S to the sum of absolute values of differences between absolute values of the voltage values VS_1, VS_5, VS_4, and VS_8 of the detection signals read from the sense coils likely to be saturated, that is, the sense coils S_1 and S_5 disposed near the drive coil Dx_1 and the sense coils S_5 and S_8 disposed near the drive coil Dx_2 and the reference voltage value VSmax.

Therefore, in the present embodiment, the amplitude of the drive signal to be input to the respective drive coils Dx_1 and Dx_2 is adjusted so that a solution A takes a minimum value or becomes less than a preset predetermined value. Accordingly, the intensity of the driving magnetic field can be adjusted to a level sufficient to acquire a high resolution without saturating the detection signals read from the sense coils S. In Equation (2), the solution A takes the minimum value when the voltage values VS_1 and VS_5 of detection signals read from the sense coils S_1 and S_5 disposed near the drive coil Dx_1 and the voltage values VS_4 and VS_8 of detection signals read from the sense coils S_4 and S_8 disposed near the drive coil Dx_2 take a value as large as possible without being saturated, and the voltage values VS_1 to VS_8 of detection signals read from the respective sense coils S_1 to S_8 are not substantially zero.

Figure 5:
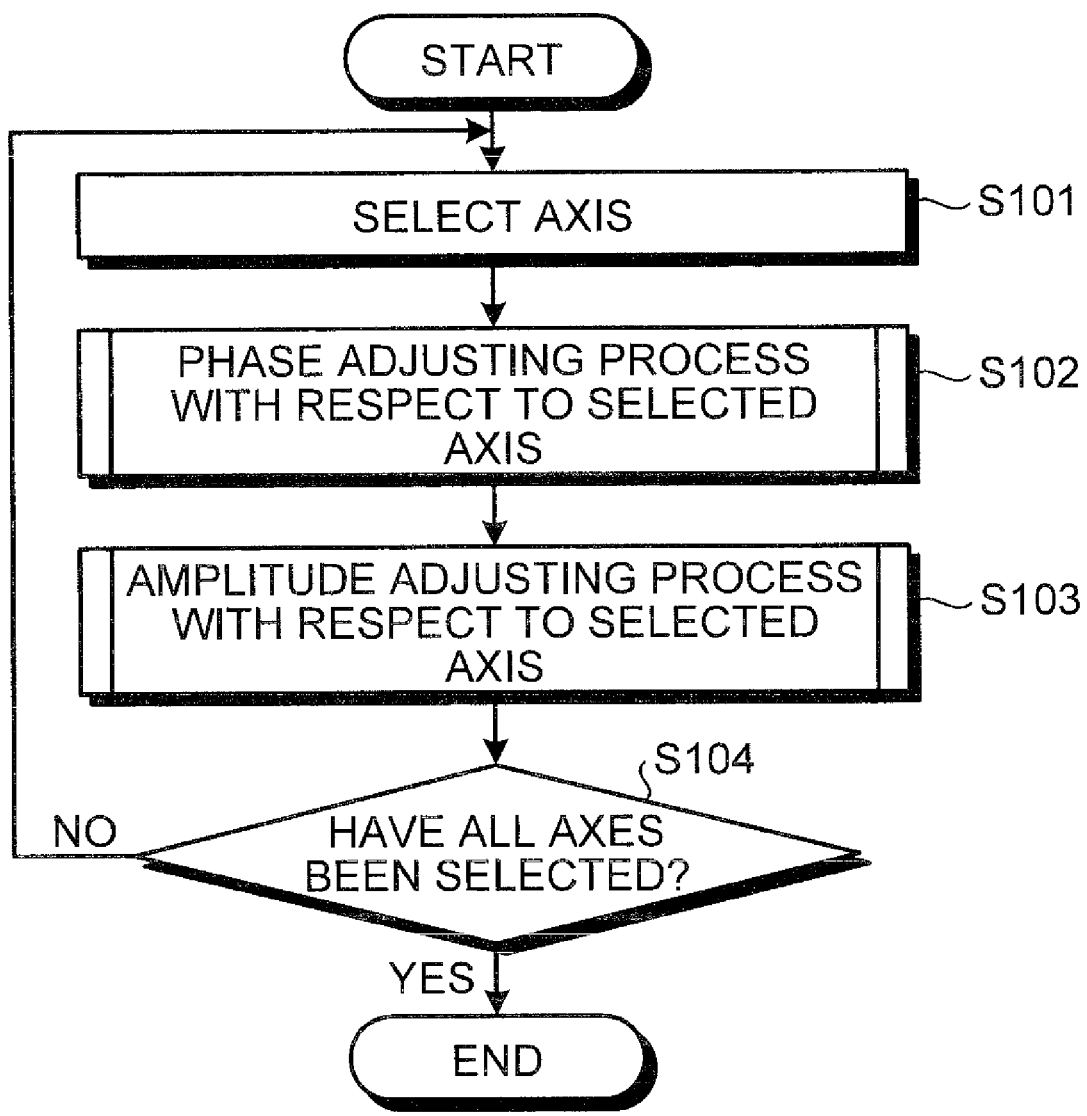
FIG. 5 is a flowchart of a schematic flow of a drive-signal adjustment operation according to the first embodiment of the present invention.
Figure 6:
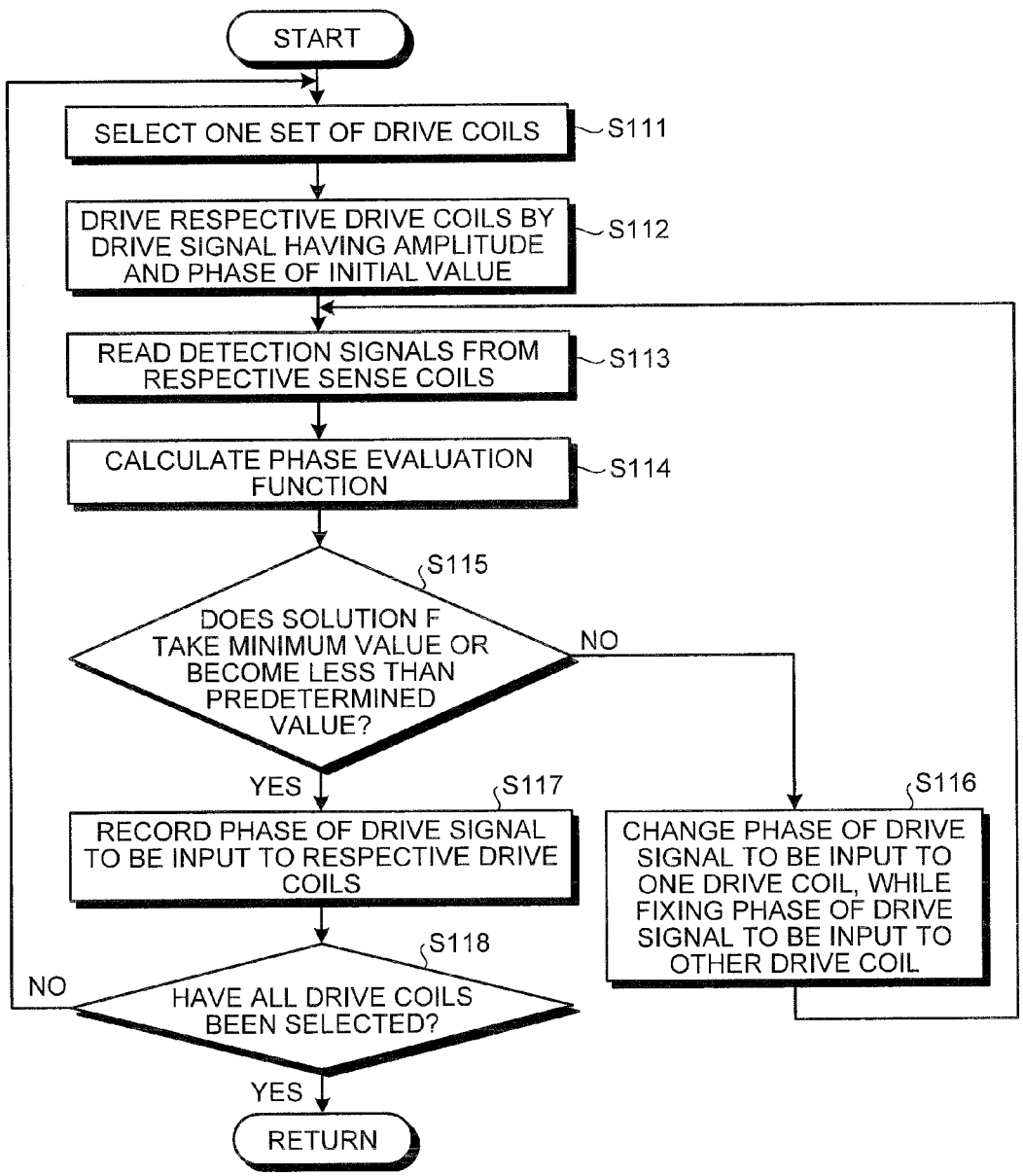
FIG. 6 is a flowchart of a flow of a phase adjusting process according to the first embodiment of the present invention.
Figure 7:
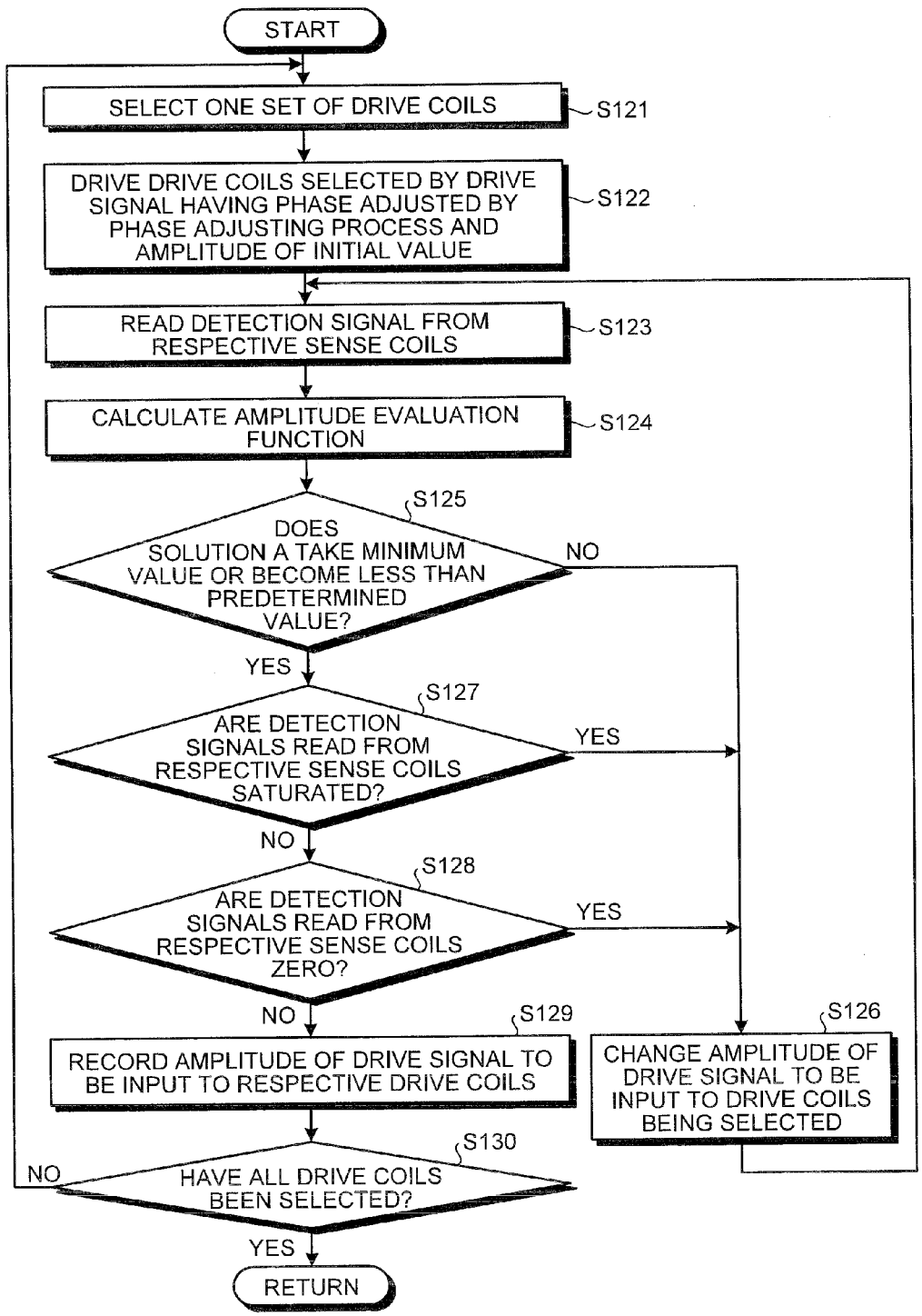
FIG. 7 is a flowchart of a flow of an amplitude adjusting process according to the first embodiment of the present invention.

The adjustment operation of the amplitude and phase of the drive signal (hereinafter, "drive-signal adjustment operation") according to the present embodiment is explained in detail with reference to the drawings. FIG. 5 is a flowchart of a schematic flow of the drive-signal adjustment operation according to the present embodiment. FIG. 6 is a flowchart of a flow of a phase adjusting process at Step S102 in FIG. 5, and FIG. 7 is a flowchart of a flow of an amplitude adjusting process at Step S103 in FIG. 5. A case that three sets of the drive coils D are provided, which generate the driving magnetic field, respectively, in a direction of the x-axis, y-axis, and z-axis in FIG. 1, is explained as an example. Further, this case is explained while focusing on an operation of the control unit 201 in the external device 200.

As shown in FIG. 5, in the drive-signal adjustment operation according to the present embodiment, the control unit 201 selects any one of an x-axis, a y-axis, and a z-axis (Step S101), and then performs the phase adjusting process with respect to the selected axis by using the phase evaluation function shown in Equation (1) (Step S102). Subsequently, the control unit 201 performs the amplitude adjusting process with respect to the selected axis by using the amplitude evaluation function shown in Equation (2) (Step S103). The control unit 201 then determines whether all axes have been selected, that is, whether the phase adjusting process and the amplitude adjusting process have been performed with respect to all axes (Step S104). When all axes have been selected (YES at Step S104), drive-signal adjusting process finishes. When all axes have not been selected (NO at Step S104), the control unit 201 returns to Step S101 to select an unselected axis, and then performs the same process.

In the phase adjusting process shown at Step S102 in FIG. 5, as shown in FIG. 6, the control unit 201 selects one set of drive coils that generate the driving magnetic field in the axial direction selected at Step S101 (see FIG. 5) (Step S111), and drives the drive-coil input-signal adjustment unit 230 so that the selected drive coils D are driven by the drive signal having the amplitude and phase registered as an initial value (Step S112). Accordingly, a signal waveform for generating the drive signal having the amplitude and phase of the initial value is input to the drive signal generator 233 connected to the drive coils D being selected from the drive-coil input-signal adjustment unit 230, and the drive signal is generated in the drive signal generator 233 and output. As a result, a magnetic field corresponding to the drive signal is generated from the drive coil being selected, and the driving magnetic field having a field intensity and a phase corresponding to the amplitude and phase of the initial value is formed in the detection space K1. For clarifying explanations, a case that the x-axis is selected at Step S101 in FIG. 5 and the drive coils Dx_1 and Dx_2 are selected at Step S111 in FIG. 6 is explained as an example.

The control unit 201 then drives the magnetic-field-information acquiring unit 210 to read the detection signals from the respective sense coils S_1 to S_8 (Step S113), and calculates the solution F from the voltage values VS_1 to VS_8 of the detection signals by using the phase evaluation function in Equation (1) (Step S114).

The control unit 201 then determines whether the solution F calculated at Step S114 takes a minimum value or becomes less than a predetermined value (Step S115). When the solution F does not take the minimum value or become less than the predetermined value (NO at Step S115), the control unit 201 changes the phase of the drive signal to be input to one drive coil Dx_2, while fixing the phase of the drive signal to be input to the other drive coil Dx_1 of the drive coils D being selected (Step S116). Subsequently, the control unit 201 returns to Step S113 to change the phase of the drive signal to be input to the drive coil Dx_2, until the solution F of the phase evaluation function takes the minimum value or becomes less than the predetermined value. In other words, the control unit 201 scans the phase of the drive signal to be input to the drive coil Dx_2 with respect to the phase of the drive signal to be input to the other drive coil Dx_1, to specify a point at which the phase evaluation function (Equation (1)) takes the minimum value or becomes less than the predetermined value. As a result, the phase of the driving magnetic field generated in the respective drive coils D can be matched with each other.

As a result of determination at Step S115, when it is determined that the solution F calculated at Step S114 takes the minimum value or becomes less than the predetermined value (YES at Step S115), the control unit 201 acquires information of the current phase of the drive signals and records the information in the memory unit 202 or the like (Step S117).

Thereafter, the control unit 201 determines whether all sets of the drive coils D that generate the driving magnetic field in the x-axis direction have been selected, that is, whether the phase of the drive signals input to all of the drive coils D relating to the x-axis direction has been adjusted (Step S118). When all sets of the drive coils D have been selected (YES at Step S118), the control unit 201 returns to the drive-signal adjustment operation in FIG. 5. As a result of determination at Step S118, when there is an unselected set of the drive coils D (NO at Step S118), the control unit 201 returns to Step S111, to perform the same process with respect to the newly selected set of the drive coils D. Accordingly, adjustment is performed so that the phases of the driving magnetic fields of all the drive coils D driven simultaneously match with each other.

In the amplitude adjusting process shown at Step S103 in FIG. 5, as shown in FIG. 7, the control unit 201 selects one set of the drive coils D that generate the driving magnetic field in the axial direction selected at Step S101 (see FIG. 5) (Step S121), and drives the drive-coil input-signal adjustment unit 230 so that the selected drive coils D are driven in the phase adjusted in the phase adjusting process and by a drive signal with the amplitude of the initial value (Step S122). Accordingly, a signal waveform for generating the drive signal having the adjusted phase and amplitude of the initial value is input to the drive signal generator 233 connected to the drive coils D being selected from the drive-coil input-signal adjustment unit 230, and a drive signal is generated in the drive signal generator 233 and input to the drive coils D. As a result, a magnetic field corresponding to the drive signal is generated from the drive coils D being selected, and the driving magnetic field having the adjusted phase and initial intensity is formed in the detection space K1. The initial value of amplitude can be a predetermined value, for example, maximum amplitude. For simplifying explanations, a case that the drive coils Dx_1 and Dx_2 are selected is explained as an example.

The control unit 201 then drives the magnetic-field-information acquiring unit 210 to read the detection signals from the respective sense coils S_1 to S_8 (Step S123), and calculates the solution A from the voltage values VS_1 to VS_8 of the detection signals by using the amplitude evaluation function in Equation (2) (Step S124).

The control unit 201 then determines whether the solution A calculated at Step S124 takes the minimum value or becomes less than the predetermined value (Step S125). When the solution A does not take the minimum value or become less than the predetermined value (NO at Step S125), the control unit 201 changes the amplitude of the drive signal to be input to the drive coils Dx_1 and Dx_2 being selected (Step S126). This can be performed by using various methods, such as adjusting the amplitude of the drive signal to be input to the drive coil Dx_1 first, and then adjusting the amplitude of the drive signal to be input to the drive coil Dx_2. Subsequently, the control unit 201 returns to Step S123 to change the amplitude of the drive signal, until the solution A of the amplitude evaluation function takes the minimum value or becomes less than the predetermined value.

As a result of determination at Step S125, when it is determined that the solution A calculated at Step S124 takes the minimum value or becomes less than the predetermined value (YES at Step S125), the control unit 201 determines whether the detection signals read from the respective sense coils S_1 to S_8 are saturated (Step S127). When the detection signals are saturated (YES at Step S127), the control unit 201 proceeds to Step S126 to adjust the amplitude of the drive signal again. As a result of determination at Step S127, when the detection signals are not saturated (NO at Step S127), the control unit 201 determines whether the detection signals read from the respective sense coils S_1 to S_8 are zero (Step S128). When the detection signals are zero (YES at Step S128), the control unit 201 proceeds to Step S126 to adjust the amplitude of the drive signal again. As a result of determination at Step S128, when the detection signals are not zero (NO at Step S128), the control unit 201 acquires the current information of amplitude of the drive signals and records the information in the memory unit 202 or the like (Step S129).

The control unit 201 then determines whether all sets of the drive coils D that generate the driving magnetic field in the x-axis direction have been selected, that is, whether the amplitude of the drive signals input to all the drive coils D has been adjusted relating to the x-axis direction (Step S130). When all sets have been selected (YES at Step S130), the control unit 201 returns to the drive-signal adjustment operation in FIG. 5. As a result of determination at Step S130, when there is an unselected set of the drive coils D (NO at Step S130), the control unit 201 returns to Step S121, to perform the same process with respect to a newly selected set of the drive coils D. Accordingly, the amplitude of the drive signals of all the drive coils D driven simultaneously is adjusted.

Figure 8:
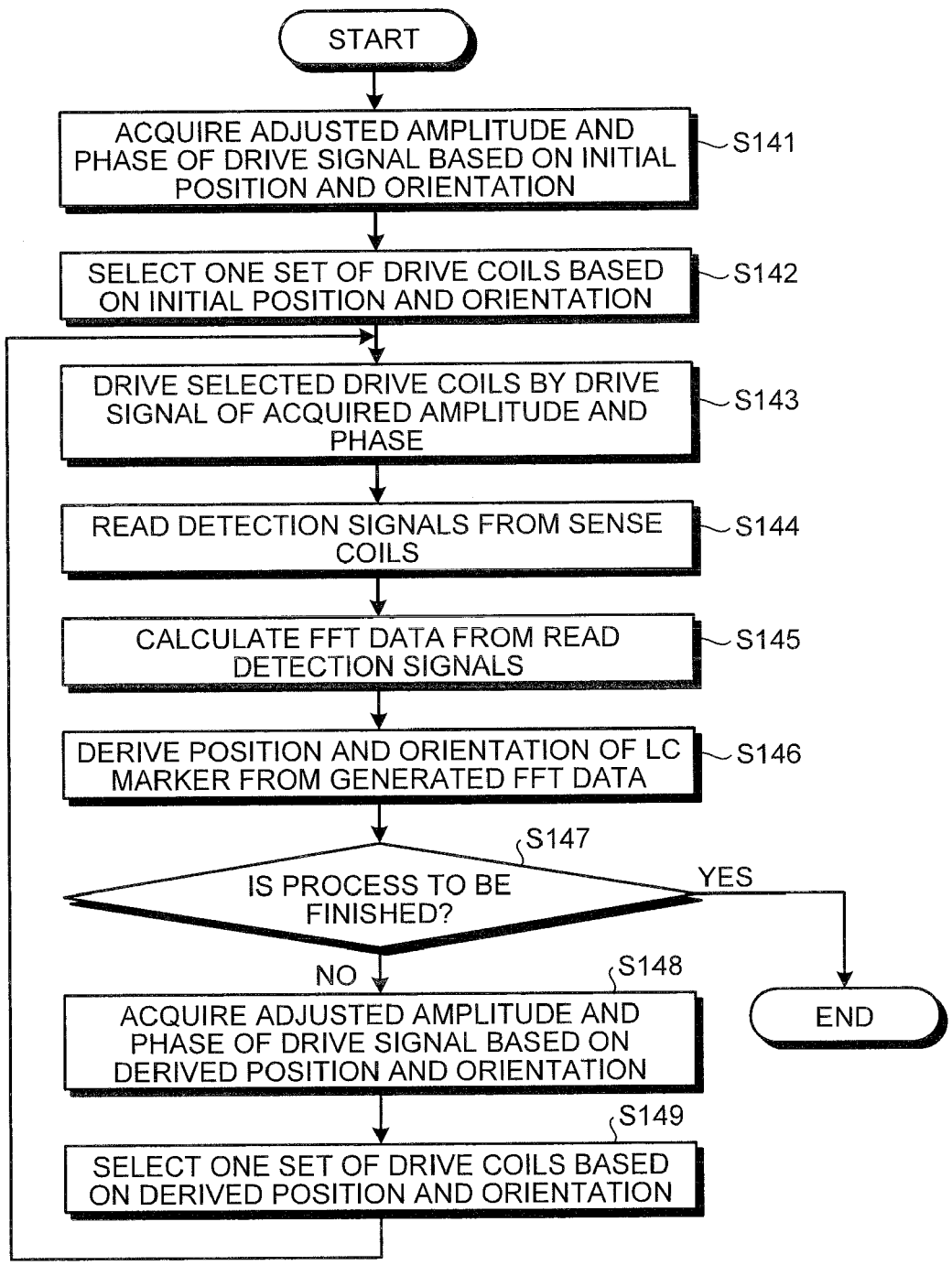
FIG. 8 is a flowchart of a schematic flow of a position detection operation according to the first or second embodiment of the present invention.

The position detection operation according to the present embodiment is explained in detail with reference to FIG. 8. FIG. 8 is a flowchart of a schematic flow of the position detection operation according to the present embodiment.

As shown in FIG. 8, in the position detection operation according to the present embodiment, the control unit 201 first assumes that the LC marker 10 is in initial position and orientation in the detection space K1, to acquire the adjusted amplitude and phase of the drive signal to be generated when the LC marker 10 is in the initial position and orientation (Step S141), and selects one set of the drive coils D that generate an optimum driving magnetic field with respect to the LC marker 10 in the initial position and orientation (Step S142). The adjusted amplitude and phase are the ones adjusted in the drive-signal adjusting process.

The control unit 201 then drives the drive-coil input-signal adjustment unit 230 so that the selected drive coils D are driven with the acquired amplitude and phase after adjustment (Step S143). Accordingly, a signal waveform for generating the drive signal having the adjusted phase and amplitude is input to the drive signal generator 233 connected to the drive coils D being selected from the drive-coil input-signal adjustment unit 230, and the drive signal is generated in the drive signal generator 233 and output. As a result, a driving magnetic field with the adjusted intensity and phase is formed in the detection space K1.

The control unit 201 drives the magnetic-field-information acquiring unit 210 to read the detection signals from the respective sense coils S (Step S144), and causes the FFT computing unit 212 in the magnetic-field-information acquiring unit 210 to calculate the FFT data of the read detection signals (Step S145). Subsequently, the control unit 201 inputs the calculated FFT data to the position-information computing unit 220 so that the position-information computing unit 220 performs a predetermined calculating process to derive the position and orientation of the LC marker 10 (Step S146). This step also includes the calibration process and correcting process. The derived position and orientation are displayed on the display unit 204 together with the in-vivo images and the like received from the LC marker 10.

The control unit 201 then determines whether a termination command has been input, for example, from the operation input unit 203 (see FIG. 1) (Step S147), and if the termination command has been input (YES at Step S147), the control unit 201 finishes the process. If the termination command has not been input (NO at Step S147), the control unit 201 acquires the adjusted amplitude and phase of the drive signal to be generated when the LC marker 10 is in the position and orientation (Step S148) based on the position and orientation derived at Step S146, and selects one set of the drive coils D that generate an optimum driving magnetic field with respect to the LC marker 10 in the position and orientation (Step S149). Thereafter, the control unit 201 proceeds to Step S143, to repeat the operation to generate the optimum driving magnetic field according to the position and orientation of the LC marker 10 until the termination command is input, and derive new position and orientation of the LC marker 10 from the detection signals detected according thereto.

The position detecting system 1 according to the present embodiment includes the LC marker 10 disposed in the detection space K1 in a state of being inserted into the subject 900, and the external device 200 disposed outside the subject 900. The LC marker 10 has the LC resonant circuit 111 that generates the resonant magnetic field corresponding to the driving magnetic field formed in the detection space K1. The external device 200 includes at least two drive coils D driven simultaneously to form a driving magnetic field in the detection space K1, at least two drive signal generators 233 that respectively input a drive signal to the drive coils D to form the driving magnetic field, at least one sense coil that detects a magnetic field formed in the detection space K1, a signal adjustment unit including the control unit 201 and the drive-coil input-signal adjustment unit 230, and a position deriving unit including the magnetic-field-information acquiring unit 210, the control unit 201, and the position-information computing unit 220. In this configuration, the control unit 201 and the drive-coil input-signal adjustment unit 230 function as the signal adjustment unit that adjusts at least one of the phase and amplitude of the drive signal to be input, respectively, to the drive coils D from the drive signal generator 233 based on the magnetic field detected by the sense coil S. Further, the magnetic-field-information acquiring unit 210 and the control unit 201 function as the position deriving unit that derives the position of the LC marker 10 based on the magnetic field detected by the sense coil S. Therefore, in the present embodiment, the magnetic field formed in the detection space K1 is actually detected, and at least one of the phase and amplitude of the drive signal to be input to the drive coils D driven simultaneously is adjusted according to the detection result. Accordingly, an optimum driving magnetic field can be formed in the detection space K1, and as a result, the position detecting system 1 and a position detecting method thereof that can detect the position of the LC marker 10 highly accurately by generating an optimum driving magnetic field without relying on the apparatus characteristics can be realized.

The signal adjustment unit including the control unit 201 and the drive-coil input-signal adjustment unit 230 adjusts at least one of the phase and amplitude of the drive signal by using the evaluation function for evaluating at least one of the phase and amplitude of the drive signal based on an intensity (for example, the voltage value VS) of the magnetic field detected by the sense coil S. The evaluation function includes, for example, a phase evaluation function (see Equation (1)) for calculating the sum of absolute values of the intensity of a magnetic field (the voltage value VS) detected by the sense coil S. The signal adjustment unit adjusts the phase of the drive signal so that the solution F of the phase evaluation function takes the minimum value or becomes less than the predetermined value, when the drive signal to be input, respectively, to the at least two drive coils D is input. Accordingly, the phase of the driving magnetic field respectively input to the drive coils D driven simultaneously can be aligned.

The evaluation function also includes an amplitude evaluation function (see Equation (2)) for adding the sum of reciprocal numbers of the intensity of a magnetic field detected by the sense coil S to the sum of absolute values of a difference between the intensity of a magnetic field (the voltage value VS) detected by the sense coil S and a preset predetermined value. The signal adjustment unit adjusts the amplitude of the drive signal so that the solution A of the amplitude evaluation function takes a minimum value or becomes less than a predetermined value, when the drive signal to be input, respectively, to the at least two drive coils D is input. Accordingly, the amplitude of the drive signal respectively input to the drive coils D driven simultaneously can be adjusted.

First Modification

A modification of the amplitude evaluation function according to the present embodiment is explained. The following Equation (3) represents an amplitude evaluation function according to a first modification. In Equation (3), $VS\_1r$ to $VS\_8r$ are ideal values of the voltage values $VS\_1$ to $VS\_8$ read from the sense coils $S\_1$ to $S\_8$, acquired by a simulation or the like.

$$A = |VS\_1r - |VS\_1|| + |VS\_2r - |VS\_2|| + \ldots + |VS\_8r - |VS\_8|| \quad (3)$$

The amplitude evaluation function shown in Equation (3) is a function for calculating the sum of absolute values of differences between the voltage values $VS\_1$ to $VS\_8$ read from the sense coils $S\_1$ to $S\_8$ and the ideal values $VS\_1r$ to $VS\_8r$ thereof. In the first modification, at Step S126 in FIG. 7, the amplitude of the drive signal to be input to the respective drive coils $Dx\_1$ and $Dx\_2$ is adjusted so that the solution A acquired by the amplitude evaluation function in Equation (3) takes the minimum value or becomes less than the predetermined value. Accordingly, the intensity of the driving magnetic field can be adjusted to a level sufficient to acquire a high resolution without saturating the detection signals read from the sense coil S. In Equation (3), the solution A becomes a minimum when the difference between the ideal values VS_1r to VS_8r acquired by a simulation or the like and the voltage values VS_1 to VS_8 read from the sense coils S_1 to S_8, that is, the difference between an ideal magnetic field distribution and a magnetic field distribution of the driving magnetic field actually formed is minimized. Because other configurations are identical to those of the first embodiment described above, detailed explanations thereof will be omitted.

Second Modification

In the above embodiment, in Equation (2), it is assumed that weights of the sense coils S_1, S_5, S_4, and S_8 near the drive coils D are set to "1" and weights of other sense coils S_2, S_3, S_6, and S_7 are set to "0", respectively. In the first modification, in Equation (3), it is assumed that the weights of all the sense coils S are "1". However, the present invention is not limited thereto, and as in the amplitude evaluation function shown in the following Equation (4) or equation (5), the weights of the respective sense coils S_1 to S_8 can be set in advance, and this weighting can be taken into consideration in Equation (2). Further, "a" to "h" in Equation (4) or equation (5) are weights set to the respective sense coils S_1 to S_8, and are for example, positive integers. The weights can be set according to a positional relation between the respective drive coils D and the respective sense coils S. At this time, it is desired to set the weights such that, for example, weights of the sense coils close to the drive coils, that is, values of a, d, e, and h take larger values than values of b, c, f, and g.

$$A = a|VS\text{max} - |VS\_1|| + b|VS\text{max} - |VS\_2|| + \\ c|VS\text{max} - |VS\_3|| + d|VS\text{max} - |VS\_4|| + e|VS\text{max} - |VS\_5|| + \\ f|VS\text{max} - |VS\_6|| + g|VS\text{max} - |VS\_7|| + \\ h|VS\text{max} - |VS\_8|| + \frac{a}{|VS\_1|} + \frac{b}{|VS\_2|} + \dots + \frac{h}{|VS\_8|} \quad (4)$$

$$A = a|VS\_1r - |VS\_1|| + b|VS\_2r - |VS\_2|| + \\ c|VS\_3r - |VS\_3|| + d|VS\_4r - |VS\_4|| + e|VS\_5r - |VS\_5|| + \\ f|VS\_6r - |VS\_6|| + g|VS\_7r - |VS\_7|| + h|VS\_8r - |VS\_8|| \quad (5)$$

Regarding not only the amplitude evaluation function shown in Equation (2) or equation (3) but also the phase evaluation function shown in Equation (1), the evaluation functions can be weighted according to the arrangement of the sense coils S and the drive coils D by using predetermined weights a to h, as shown in the following Equation (6). The weights used in Equations (4) to (6) do not need to be a common value, and can be variously changed.

$$F = a|VS\_1| + b|VS\_2| + c|VS\_3| + d|VS\_4| + e|VS\_5| + \\ f|VS\_6| + g|VS\_7| + h|VS\_8| \quad (6)$$

As described above, the weight is set according to the positional relation between the respective drive coils D and the respective sense coils S and the solution A is derived by adding or multiplying the weight to or by the intensity (a value determined by the voltage value VS) of the magnetic field detected by the sense coils S. Accordingly, the evaluation function can be determined, strongly taking into consideration the sense coils S likely to be saturated, according to the positional relation or the like, and at least one of the amplitude and phase of the drive signal can be adjusted more accurately.

The evaluation function described above does not include a term regarding the amplitude (the voltage value VS) of the drive signal to be input to the respective drive coils D. However, for example, when an evaluation function taking the amplitude of the respective drive signals into consideration is used, the weight can be set according to at least one of the positional relation between the respective drive coils and sense coils and a shape of the respective drive coils, and the weight can be added or multiplied to or by the amplitude of the drive signal (a value determined by the amplitude of the drive signal), thereby deriving a solution.

Further, the weight can be changed by the control unit 201 (the signal adjustment unit) based on at least one of the amplitude or phase of the drive signal and the intensity of a magnetic field detected by the sense coil. In this case, for example, when the control unit 201 largely changes the phase or amplitude of the drive signal, the control unit 201 increases the weight with respect to the sense coil S affected by the change, and decreases the weight with respect to the sense coil S hardly affected by the change. Accordingly, the respective evaluation functions can be made sensitive to the change in phase or amplitude, thereby enabling to adjust the drive signal with higher accuracy.

Other configurations of the second modification are identical to those of the first embodiment described above or the first modification thereof, and thus detailed explanations of the second modification will be omitted.

Second Embodiment

Configurations and operations of a position detecting system 2 according to a second embodiment of the present invention are explained below in detail with reference to the drawings. In the following explanations, constituent elements identical to those of the first embodiment of the present invention are denoted by like reference characters and explanations thereof will be omitted.

Configuration of Position Detection

FIG. 9 is a schematic diagram of a schematic configuration of the position detecting system 2 according to the present embodiment. As is clear from the comparison between FIGS. 9 and 1, in the same configuration as that of the position detecting system 1 shown in FIG. 1, in the position detecting system 2, auxiliary coils Ex_1 and Ex_2 (hereinafter, E is denoted as the reference character of an arbitrary auxiliary coil) are disposed near the sense coil S, and the external device 200 includes an auxiliary-coil input-signal adjustment unit 240 that adjusts amplitude and phase of a signal used for driving the auxiliary coil E (hereinafter, "auxiliary signal"), and auxiliary signal generators (also referred to as "auxiliary-signal input units") 243a and 243b that respectively generate auxiliary signals to be input to the auxiliary coils Ex_1 and Ex_2 under control of the auxiliary-coil input-signal adjustment unit 240. In FIG. 9, a configuration in which the auxiliary signal generators 243a and 243b are formed separately from the external device 200 is explained as an example; however, the present invention is not limited thereto, and these can be provided in the external device 200. In an example shown in FIG. 9, the sense coils S_5 to S_8 are disposed in a space put between the drive coils Dx_1 and Dx_2, and the sense coils S_1 to S_4 are disposed outside the space. Other configurations of the position detecting system 2 are identical to those of the position detecting system 1 shown in FIG. 1.

Generally, the driving magnetic fields are substantially parallel in the space put between the drive coils Dx_1 and Dx_2 disposed opposite to each other, but not parallel outside the space (near the drive coils D), and expands outward. Therefore, a driving magnetic field substantially parallel to the x-axis direction is input to the sense coils S_5 to S_8, whereas a driving magnetic field not parallel to the x-axis direction is input to the sense coils S_1 to S_4.

Further, generally, the intensity of the driving magnetic field to be input to the sense coils S increases as approaching the drive coils D. Therefore, in the example shown in FIG. 9, the detection signals read from the sense coils S_1 and S_4 close to the drive coils Dx_1 and Dx_3 are likely to be saturated.

Therefore, in the present embodiment, as shown in FIG. 9, auxiliary coils Ex_1 and Ex_2 are respectively provided near the sense coils S susceptible to the driving magnetic field generated by the drive coils D, for example, the sense coils S_1 and S_4 disposed adjacent to the drive coils D. The respective drive coils E are driven to generate a magnetic field negating the driving magnetic field input to the respective sense coils S (hereinafter, "auxiliary magnetic field") at the time of reading the detection signal from the respective sense coils S. Accordingly, components of the driving magnetic field included in the detection signal read from the sense coils S can be reduced, and thus the driving magnetic field with a larger intensity can be generated, thereby enabling to perform position detection with higher accuracy.

The auxiliary-coil input-signal adjustment unit 240, the auxiliary signal generator 243, and the auxiliary coils E in FIG. 9 function as a mechanism for generating the auxiliary magnetic field for negating the driving magnetic field input to the respective sense coils S (hereinafter, "auxiliary system").

The auxiliary-coil input-signal adjustment unit 240 calculates a signal waveform of a frequency substantially equal to the resonant frequency F0 according to the control signal input from the control unit 201, and outputs the signal waveform to the auxiliary signal generator 243 that drives the auxiliary coil E that generates an optimum auxiliary magnetic field with respect to the sense coil S. Plural auxiliary coils E can be driven simultaneously.

The respective auxiliary signal generators 243 generate the auxiliary signal according to the signal waveform input from the auxiliary-coil input-signal adjustment unit 240, amplifies the current of the auxiliary signal, and inputs the amplified auxiliary signal to the auxiliary coils E. The auxiliary coils E, to which the amplified auxiliary signal is input, generate a auxiliary magnetic field of a frequency substantially equal to the resonant frequency F0 held by the LC resonant circuit 111 in the LC marker 10 to negate the driving magnetic field to be input to the sense coil S to be read.

Position Detection Operation

The position detection operation of the position detecting system 2 according to the present embodiment is explained next in detail. As described above, in the present embodiment, the drive signal generator 233 outputs the drive signal so that the drive coils D generate the driving magnetic field, and the LC marker 10 generates the resonant magnetic field. The resonant magnetic field is detected together with other magnetic fields of resonant frequency F0 by the sense coil S as a detection signal. At this time, the auxiliary signal generator 243 outputs the auxiliary signal so that the auxiliary coil E generates the auxiliary signal to generate the auxiliary magnetic field for negating the driving magnetic field to be input to the sense coil S to be read. The detection signals read from the respective sense coils S are converted to the FFT data indicating the information of the detected magnetic field. The position detecting process including the calibration process and the correcting process is performed by using the FFT data, thereby deriving the position and orientation of the LC marker 10.

Therefore, in the present embodiment, the driving magnetic field and the auxiliary magnetic field having a intensity and a phase sufficient to acquire a high resolution are formed in the detection space K1 without saturating the detection signals read from the sense coils S, by adjusting the intensity and phase of the driving magnetic field and the auxiliary magnetic field. Accordingly, the optimum driving magnetic field and the auxiliary magnetic field can be formed in the detection space K1, and as a result, the position detection accuracy can be improved.

In the present embodiment, adjustment of the intensity and phase of the driving magnetic field and the auxiliary magnetic field is performed by using the evaluation function as in the first embodiment described above. The respective evaluation functions are as described below. A case that the number of the sense coils S is eight (S_1 to S_8), the number of sets of the drive coils D is one (Dx_1 and Dx_2), the number of the auxiliary coils E is two (Ex_1 and Ex_2), and these are respectively disposed as shown in FIG. 9 is explained. However, the present invention is not limited thereto, and the configuration can be appropriately changed.

At the time of setting the evaluation function according to the present embodiment, it is assumed that the amplitude of the drive signal to be input to the drive coils Dx_1 and Dx_2 is VDx_1 and VDx_2, respectively, and the amplitude of the drive signal to be input to the auxiliary coils Ex_1 and Ex_2 is VEx_1 and VEx_2, respectively. Amplitudes VDx_1, VDx_2, VEx_1, and VEx_2 are parameters used for the evaluation function like the voltage values VS_1 to VS_8. In the voltage values VS_1 to VS_8, it is assumed that an in-phase voltage value is positive, and a reversed-phase voltage value is negative with respect to the phase of the voltage value VS_1.

Phase Adjustment

A flow for adjusting the phases of drive signals input respectively to the drive coils D x_1 and Dx_2 driven simultaneously and auxiliary signals input respectively to the auxiliary coils Ex_1 and Ex_2 is explained. For example, when it is assumed that the auxiliary coil Ex_1 is an optimum auxiliary coil E for negating the driving magnetic field to be input to the sense coils S_1 and S_2, a phase evaluation function for adjusting the phase of the magnetic field respectively generated by the drive coil Dx_1 and the auxiliary coil Ex_1 (hereinafter, "1a phase evaluation function") can be expressed by the following Equation (7) by using the parameters described above.

$$F1=|VS\_1|+|VS\_2| \tag{7}$$

A solution of the 1a phase evaluation function, that is, a total value F1 of an intensity of the driving magnetic field to be input to the sense coils S_1 and S_2 and an intensity of the auxiliary magnetic field decreases as the phases of the magnetic fields respectively generated by the drive coil Dx_1 and the auxiliary coil Ex_1 are aligned, and when the phases of the two magnetic fields are aligned completely, the total value F1 becomes a minimum.

For example, when it is assumed that the auxiliary coil Ex_2 is an optimum auxiliary coil E for negating the driving magnetic field to be input to the sense coils S_4 and S_3, a phase evaluation function for adjusting the phases of the magnetic fields respectively generated by the drive coil Dx_2 and the auxiliary coil Ex_2 (hereinafter, "1b phase evaluation function") can be expressed by the following Equation (8) by using the parameters described above.

$$F2=|VS\_3|+|VS\_4| \tag{8}$$

A solution of the 1b phase evaluation function, that is, a total value F2 of an intensity of the driving magnetic field to be input to the sense coils S_4 and S_3 and an intensity of the auxiliary magnetic field decreases as the phases of the magnetic fields respectively generated by the drive coil Dx_2 and the auxiliary coil Ex_2 are aligned, and when the phases of the two magnetic fields are aligned completely, the total value F2 becomes a minimum.

Further, when the magnetic fields respectively generated by the drive coils Dx_1 and Dx_2 negate each other on the surface of the sense coil, a phase evaluation function for adjusting the phases of the magnetic fields respectively generated by the drive coils Dx_1 and Dx_2 (hereinafter, "second phase evaluation function") can be expressed by the following Equation (9) by using the parameters described above.

$$F3 = |VS\_1| + |VS\_2| + \ldots + |VS\_8| \quad (9)$$

A total value F3 decreases as the phases of the magnetic fields respectively generated by the drive coil Dx_1 and Dx_2 are aligned, and when the phases of the two magnetic fields are aligned completely, the total value F3 becomes a minimum.

Therefore, in the present embodiment, the phases of the drive signal to be input to the drive coils D and the auxiliary signal to be input to the auxiliary coils E are adjusted by using the 1a, 1b, and second phase evaluation functions.

In the phase adjustment, the phases of the drive signal and the auxiliary signal to be input to the drive coils D and the auxiliary coils E, respectively, are adjusted so that solutions of the respective phase evaluation functions represented by Equations (7) to (9) take a minimum value or become lower than a predetermined value set in advance.

Amplitude Adjustment

A flow for adjusting the amplitude of the drive signal to be input respectively to the drive coils Dx_1 and Dx_2 driven simultaneously and the amplitude of the auxiliary signal to be input respectively to the auxiliary coils Ex_1 and Ex_2 is explained next. In the amplitude adjustment of the drive signal and the auxiliary signal, for example, a priority order is set in the drive coil D and the auxiliary coil E, and the drive signal to be input to the drive coil D is preferentially adjusted to become optimum amplitude.

In the amplitude adjustment according to the present embodiment, for example, the following Equations (10) to (12) are used as evaluation functions for amplitude adjustment (hereinafter, respectively "first, 2a, and 2b amplitude evaluation functions"). The first amplitude evaluation function in Equation (10) is an evaluation function for the drive coils Dx_1 and Dx_2, the 2a amplitude evaluation function in Equation (11) is an evaluation function for the auxiliary coils Ex_1, and the 2b amplitude evaluation function in Equation (12) is an evaluation function for the auxiliary coils Ex_2. In Equation (10), VDmax denotes a maximum value of the amplitude that can be set for the drive signal.

$$A1 = |VS\text{max} - |VS\_1|| + |VS\text{max} - |VS\_5|| + \\ |VS\text{max} - |VS\_4|| + |VS\text{max} - |VS\_8|| + \frac{1}{|VS\_1|} + \frac{1}{|VS\_2|} + \\ \ldots + \frac{1}{|VS\_8|} + ||VD\text{max} - VDx\_1| + |VD\text{max} - VDx\_2|| \quad (10)$$

$$A2 = |VS\text{max} - |VS\_1|| \quad (11)$$

$$A3 = |VS\text{max} - |VS\_4|| \quad (12)$$

The above equation (10) represents a function for adding the sum of reciprocal numbers of the voltage values VS_1 to VS_8 of detection signals read from the respective sense coils S and the sum of difference between the maximum value VDmax of the amplitude that can be taken by the drive signal and the actual amplitude of the drive signal to the sum of absolute values of differences between absolute values of the voltage values VS_1, VS_5, VS_4, and VS_8 of the detection signals read from the sense coils likely to be saturated, that is, the sense coils S_1 and S_5 disposed near the drive coil Dx_1 and the sense coils S_4 and S_8 disposed near the drive coil Dx_2 and the reference voltage value VSmax.

Therefore, in the present embodiment, the amplitude of the drive signal to be input to the respective drive coils Dx_1 and Dx_2 is adjusted so that a solution A1 takes a minimum value or becomes less than a preset predetermined value. Accordingly, the intensity of the driving magnetic field can be adjusted to a level sufficient to acquire a high resolution without saturating the detection signals read from the sense coils S. In Equation (10), the solution A1 takes the minimum value when the voltage values VS_1 and VS_5 of detection signals read from the sense coils S_1 and S_5 disposed near the drive coil Dx_1 and the voltage values VS_4 and VS_8 of detection signals read from the sense coils S_4 and S_8 disposed near the drive coil Dx_2 take a value as large as possible without being saturated, and the voltage values VS_1 to VS_8 of detection signals read from the respective sense coils S_1 to S_8 are not zero.

The equation (11) is a function designating an absolute value of a difference between the detection signal read from the sense coil S_1 affected most by the auxiliary magnetic field generated by the auxiliary coil Ex_1 and VSmax of the voltage value VS_1 as a solution A2. The equation (12) is a function designating an absolute value of a difference between the detection signal read from the sense coil S_4 affected most by the auxiliary magnetic field generated by the auxiliary coil Ex_2 and VSmax of the voltage value VS_4 as a solution A3.

Therefore, in the present embodiment, amplitude of the auxiliary signal to be input to the respective auxiliary coils Ex_1 and Ex_2 is adjusted so that the solution A2 and the solution A3 take values less than a preset predetermined value. Accordingly, the driving magnetic field to be input to the sense coil likely to be affected by the driving magnetic field can be negated accurately. As a result, the intensity can be adjusted to a level sufficient to acquire a high resolution without saturating the detection signals read from the sense coils S.

Figure 11A:
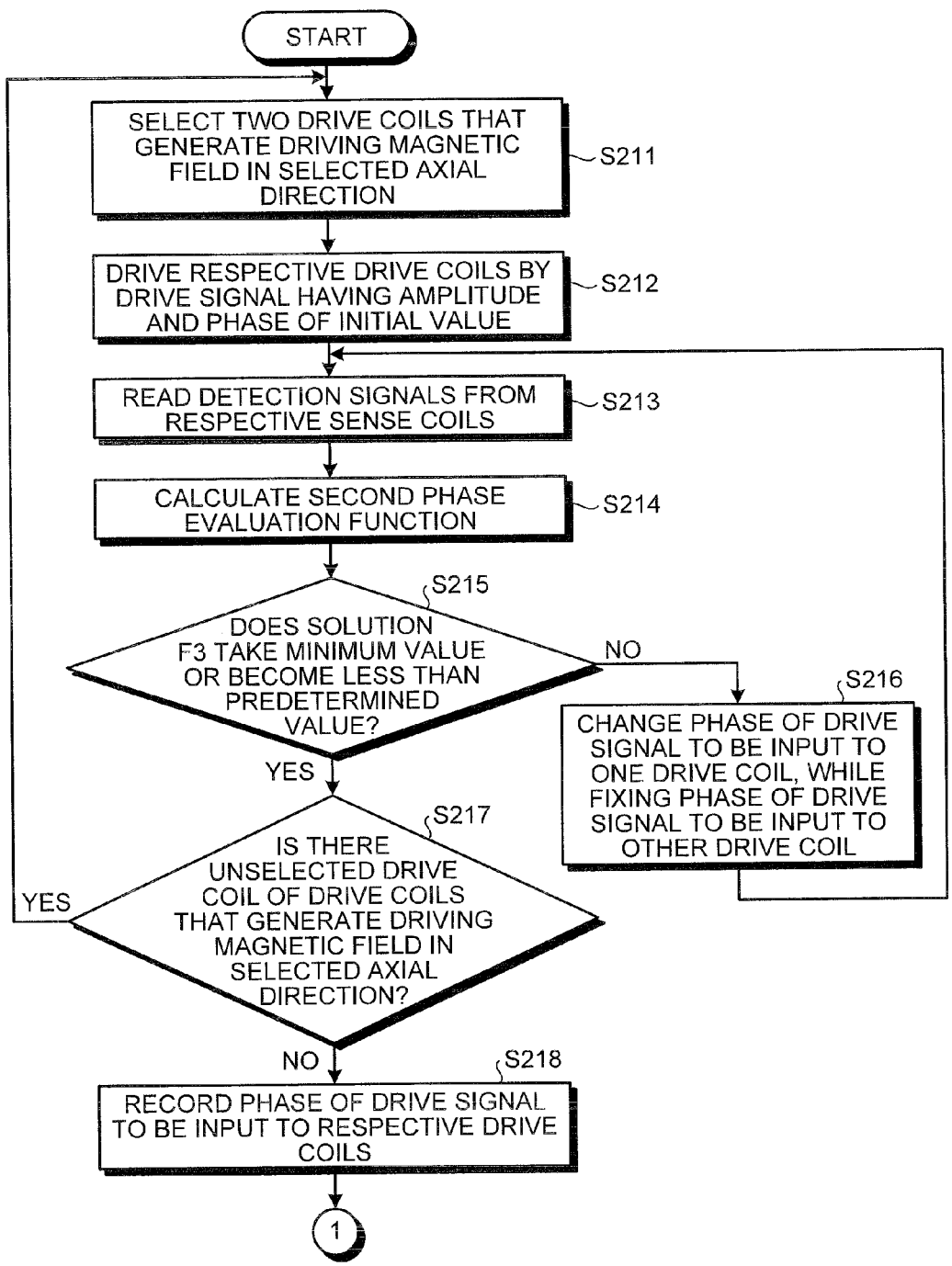
Figure 12:
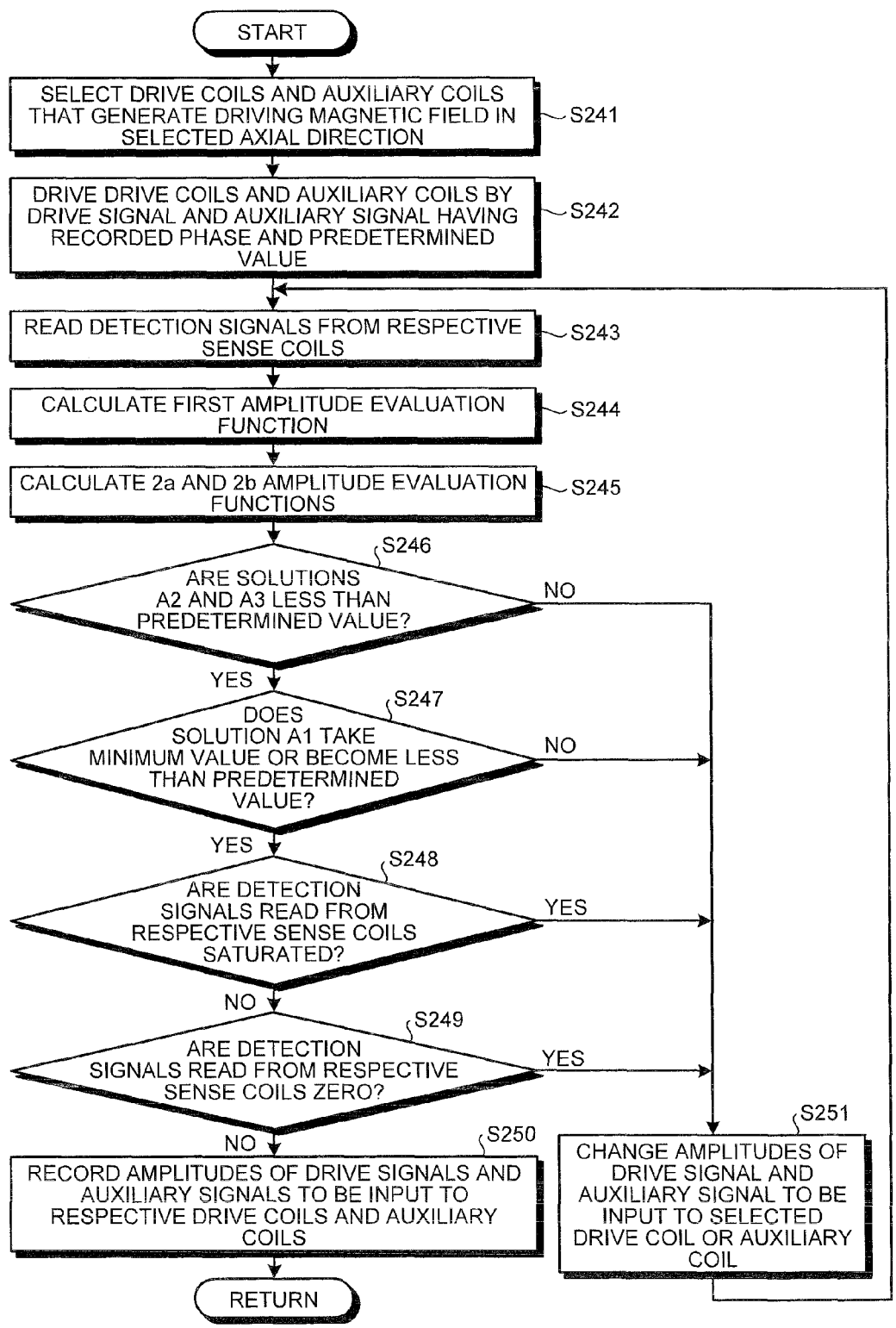
FIG. 12 is a flowchart of a flow of an amplitude adjusting process according to the second embodiment of the present invention.

The adjustment operation of the drive signal and the auxiliary signal according to the present embodiment is explained in detail with reference to the drawings. FIG. 10 is a flowchart of a schematic flow of a drive-signal and auxiliary-signal adjustment operation according to the present embodiment. FIGS. 11A and 11B are flowcharts of a flow of a phase adjusting process at Step S202 in FIG. 10, and FIG. 12 is a flowchart of a flow of an amplitude adjusting process at Step S203 in FIG. 10. There is explained a case that three sets of the drive coils D that generate a driving magnetic field, respectively, in a direction of an x-axis, a y-axis, and a z-axis in FIG. 9, and the auxiliary coils E corresponding to the respective drive coils D are provided as an example.

As shown in FIG. 10, in the drive-signal and auxiliary-signal adjustment operation according to the present embodiment, the control unit 201 selects any one of the x-axis, y-axis, and z-axis (Step S201), and then performs the phase adjusting process with respect to the selected axis by using the 1a, 1b, and second phase evaluation functions shown in Equations (7) to (9) (Step S202). Subsequently, the control unit 201 performs the amplitude adjusting process with respect to the selected axis by using the first to third amplitude evaluation functions shown in Equations (10) to (12) (Step S203). The control unit 201 then determines whether all axes have been selected, that is, whether the phase adjusting process and the amplitude adjusting process have been performed with respect to all axes (Step S204). When all axes have been selected (YES at Step S204), drive-signal and auxiliary-signal adjusting process finishes. On the other hand, when all axes have not been selected (NO at Step S204), the control unit 201 returns to Step S201 to select an unselected axis, and then performs the same process.

In the phase adjusting process shown at Step S202 in FIG. 10, as shown in FIG. 11A, the control unit 201 selects one set of drive coils that generate the driving magnetic field in the axial direction selected at Step S201 (see FIG. 10) (Step S211), and drives the selected drive coils having the amplitude and phase of the initial value (Step S212). For clarifying explanations, a case that the drive coils Dx_1 and Dx_2 are selected at Step S211 in FIG. 11A is explained as an example.

The control unit 201 then reads the detection signals from the respective sense coils S_1 to S_8 (Step S213), and calculates an solution F3 from the voltage values VS_1 to VS_8 of the detection signals by using the second phase evaluation function in Equation (9) (Step S214).

The control unit 201 then determines whether the solution F3 calculated at Step S214 takes a minimum value or becomes less than a predetermined value (Step S215). When the solution F3 does not take the minimum value or become less than the predetermined value (NO at Step S215), the control unit 201 changes the phase of the drive signal to be input to one drive coil Dx_2, while fixing the phase of the drive signal to be input to the other drive coil Dx_1 of the drive coils D being selected (Step S216). Subsequently, the control unit 201 returns to Step S213 to change the phase of the drive signal until the solution F3 of the second phase evaluation function takes the minimum value.

As a result of determination at Step S215, when it is determined that the solution F3 calculated at Step S214 takes the minimum value or becomes less than the predetermined value (YES at Step S215), the control unit 201 determines whether there is an unselected set of the drive coils D of the sets of the drive coils D that generate the driving magnetic field in the axial direction selected at Step S201 (see FIG. 10) (Step S217). When there is an unselected set of the drive coils D (YES at Step S217), the control unit 201 returns to Step S211, to select the unselected set of the drive coils D. When there is no unselected set of the drive coils D (NO at Step S217), the control unit 201 acquires information of the current phase of the respective drive signals being input to the respective drive coils D and records the information in the memory unit 202 or the like (Step S218).

The control unit 201 then selects one of the auxiliary coils E that generate the auxiliary magnetic field in the axial direction selected at Step S201 (see FIG. 10) (Step S219), and also selects one of the drive coils D that generate the driving magnetic field for negating the auxiliary magnetic field generated by the selected auxiliary coil E (Step S220). For clarifying the following explanations, a case that the x-axis is selected at Step S201 in FIG. 10, and the auxiliary coil Ex_1 and the drive coil Dx_1 are respectively selected at Steps S219 and S220 in FIG. 11B is explained as an example.

The control unit 201 drives the selected drive coil Dx_1 and auxiliary coil Ex_1 with the amplitude and phase of the initial value (Step S221). The control unit 201 then drives the magnetic-field-information acquiring unit 210 to read the detection signals from the sense coils adjacent to the selected auxiliary coil Ex_1 of the plural sense coils S, that is, the sense coils S_1 and S_2 likely to be affected by the selected drive coil Dx_1 (Step S222), and calculates a solution F1 from the voltage values VS_1 and VS_2 of the read detection signals by using the 1a phase evaluation function in Equation (7) (Step S223).

The control unit 201 determines whether the solution F1 calculated at Step S223 takes a minimum value or becomes less than a predetermined value (Step S224). When the solution F1 does not take the minimum value or become less than the predetermined value (NO at Step S224), the control unit 201 changes the phase of the auxiliary signal to be input to the auxiliary coil Ex_1 being selected, while fixing the phase of the drive signal to be input to the drive coil Dx_1 being selected (Step S225). Subsequently, the control unit 201 returns to Step S222, to change the phase of the auxiliary signal to be input to the auxiliary coil Ex_1 until the solution F1 of the 1a phase evaluation function takes the minimum value or becomes less than the predetermined value. In other words, the control unit 201 scans the phase of the auxiliary signal to be input to the auxiliary coil Ex_1 with respect to the phase of the drive signal to be input to the drive coil Dx_1, to specify a point at which the 1a phase evaluation function (Equation (7)) takes a minimum value or becomes less than the predetermined value. As a result, the phase of the driving magnetic field generated by the drive coil Dx_1 and the phase of the auxiliary magnetic field generated by the auxiliary coil Ex_1 can be matched with each other.

As a result of determination at Step S224, when it is determined that the solution F1 calculated at Step S223 takes the minimum value or becomes less than the predetermined value (YES at Step S224), the control unit 201 acquires information of the current phase of the respective drive signals and records the information in the memory unit 202 or the like (Step S226).

Thereafter, the control unit 201 determines whether there is an unselected auxiliary coil E of the auxiliary coils E that generate the auxiliary magnetic field in the x-axis direction being selected (Step S227). When there is an unselected auxiliary coil E (YES at Step S227), the control unit 201 returns to Step S219 to select an unselected auxiliary coil E and then performs the same process. For example, in the example described above, because the auxiliary coil Ex_2 of the auxiliary coils Ex_1 and Ex_2 is unselected, the control unit 201 returns to Step S219 to select the auxiliary coil Ex_2, and also selects the drive coil Dx_2 for negating the influence of the auxiliary magnetic field generated by the auxiliary coil Ex_2, to perform the same process by using the detection signals read from the sense coils S_3 and S_4 likely to be affected by the auxiliary magnetic field from the auxiliary coil Ex_2 and an solution F2 calculated by the 1b phase evaluation function. Accordingly, adjustment is performed so that the phase of the drive signal input to the drive coil Dx_1 matches with the phase of the auxiliary signal input to the auxiliary coil Ex_1, and the phase of the drive signal input to the drive coil Dx_2, and the phase of the drive signal input to the drive coil Dx_2 matches with the phase of the auxiliary signal input to the auxiliary coil Ex_2.

When there is no unselected auxiliary coil E (NO at Step S227), the control unit 201 returns to the drive-signal and auxiliary-signal adjustment operation in FIG. 10. Accordingly, the phases of the drive signal and auxiliary signal of all the drives coils D driven simultaneously and the auxiliary coils E are adjusted to match with each other.

In the amplitude adjusting process shown in Step S203 in FIG. 10, as shown in FIG. 12, the control unit 201 respectively selects a pair of the drive coils D that generate the driving magnetic field in the axial direction selected at Step S201 (see FIG. 10) and the auxiliary coils E that respectively negate the influence of the driving magnetic field generated by the drive coils D on the sense coils S (Step S241), and drives the drive-coil input-signal adjustment unit 230 and the auxiliary-coil input-signal adjustment unit 240 so that the selected drive coils D and the auxiliary coils E are driven, respectively, by a drive signal having the phase adjusted by the phase adjusting process and the amplitude of the initial value (Step S242). Accordingly, a signal waveform for generating the drive signal having the adjusted phase and amplitude of the initial value is input from the drive-coil input-signal adjustment unit 230 to the drive signal generator 233 connected to the drive coils D being selected, and the drive signal generator 233 generates a drive signal and inputs the drive signal to the drive coils D. Further, a signal waveform for generating the auxiliary signal having the adjusted phase and amplitude of the initial value is input from the auxiliary-coil input-signal adjustment unit 240 to the auxiliary signal generator 243 connected to the auxiliary coils E being selected, and the auxiliary signal generator 243 generates an auxiliary signal and inputs the auxiliary signal to the drive coils E. As a result, a magnetic field corresponding to the drive signal is generated by the drive coils D being selected to form the driving magnetic field having the adjusted phase and initial intensity in the detection space K1. Further, a magnetic field corresponding to the auxiliary signal is generated from the auxiliary coils E being selected to negate the driving magnetic field to be input to the sense coils S. For simplifying the following explanations, a case that drive coils Dx_1 and Dx_2 and auxiliary coils Ex_1 and Ex_2 are selected is explained as an example.

The control unit 201 drives the magnetic-field-information acquiring unit 210 to read detection signals from the respective sense coils S_1 to S_8 (Step S243), and calculates the solution A1 from the voltage values VS_1 to VS_8 of respective detection signals by using the first amplitude evaluation function in Equation (10) (Step S244). Subsequently, the control unit 201 calculates the solution A2 and the solution A3 from the voltage values VS_1 to VS_8 of the read detection signals by using the 2a amplitude evaluation function in Equation (11) and the 2b amplitude evaluation function in Equation (12) (Step S245).

The control unit 201 then determines whether solutions A2 and A3 calculated at Step S245 take a minimum value or become less than a predetermined value (Step S246). When solutions A2 and A3 do not take the minimum value or become less than the predetermined value (NO at Step S246), the control unit 201 proceeds to Step S251 to change the amplitudes of the drive signals and the auxiliary signals to be input, respectively, to the drive coils Dx_1 and Dx_2 and the auxiliary coils Ex_1 and Ex_2 being selected (Step S251). Subsequently, the control unit 201 returns to Step S243 to change the amplitudes of the drive signals and the auxiliary signals until the solution A2 of the 2a amplitude evaluation function and the solution A3 of the 2b amplitude evaluation function take the minimum value or become less than the predetermined value.

As a result of determination at Step S246, when it is determined that solutions A2 and A3 calculated at Step S245 take the minimum value or become less than the predetermined value (YES at Step S246), the control unit 201 determines whether the solution A1 calculated at Step S244 is less than the predetermined value (Step S247). When the solution A1 is not less than the predetermined value (NO at Step S247), the control unit 201 proceeds to Step S251, to change the amplitudes of the drive signals and the auxiliary signals until the solution A1 of the first amplitude evaluation function becomes less than the predetermined value.

As a result of determination at Step S247, when it is determined that the solution A1 calculated at Step S244 is less than the predetermined value (YES at Step S247), the control unit 201 determines whether the detection signals read from the respective sense coils S_1 to S_8 are saturated (Step S248). When the detection signals are saturated (YES at Step S248), the control unit 201 proceeds to Step S251, to adjust the amplitudes of the drive signals and the auxiliary signals again. As a result of determination at Step S248, when the respective detection signals are not saturated (NO at Step S248), the control unit 201 determines whether the detection signals read from the respective sense coils S_1 to S_8 are zero (Step S249). When the detection signals are zero (YES at Step S249), the control unit 201 proceeds to Step S251, to adjust the amplitudes of the drive signals and the auxiliary signals again.

On the other hand, as a result of determination at Step S249, when the detection signals are not zero (NO at Step S249), the control unit 201 records the amplitudes of the drive signals and the auxiliary signals in the memory unit 202 or the like (Step S250), and thereafter, returns to the drive-signal and auxiliary-signal adjustment operation in FIG. 10.

The position detection operation according to the present embodiment includes a driving-magnetic-field negating operation by the auxiliary coils E in addition to the operation in the first embodiment of the present invention explained with reference to FIG. 8, and thus detailed explanations thereof will be omitted.

As described above, the position detecting system 2 according to the present embodiment includes the LC marker 10 disposed in the detection space K1 in a state of being inserted into the subject 900, and the external device 200 disposed outside the subject 900. The LC marker 10 has the LC resonant circuit 111 that generates the resonant magnetic field corresponding to the driving magnetic field formed in the detection space K1. The external device 200 includes at least two drive coils D driven simultaneously to form the driving magnetic field in the detection space K1, at least two drive signal generators 233 that respectively input a drive signal for forming the driving magnetic field to the drive coils D, at least one sense coil that detects a magnetic field formed in the detection space K1, a signal adjustment unit including the control unit 201 and the drive-coil input-signal adjustment unit 230, and a position deriving unit including the magnetic-field-information acquiring unit 210 and the control unit 201, the auxiliary coil E that generates the auxiliary magnetic field for negating the driving magnetic field to be input to at least one of the sense coils S, and the auxiliary signal generator 243 that inputs the auxiliary signal to the auxiliary coil E for generating the auxiliary magnetic field. In this configuration, the control unit 201 and the drive-coil input-signal adjustment unit 230 function as the signal adjustment unit that adjusts at least one of the phase and amplitude of the drive signal to be input, respectively, to the drive coils D by the drive signal generator 233 based on the magnetic field detected by the sense coil S. Further, the magnetic-field-information acquiring unit 210 and the control unit 201 function as the position deriving unit that derives the position of the LC marker 10 based on the magnetic field detected by the sense coil S. Further, the signal adjustment unit adjusts at least one of the phase and amplitude of the drive signal to be input to at least one of the drive coils D by the drive signal generator 233 and/or at least one of the phase and amplitude of the auxiliary signal to be input to at least one of the auxiliary coils E by the auxiliary signal generator 243. Therefore, in the present embodiment, the magnetic field formed in the detection space K1 is actually detected, and at least one of the phase and amplitude of the drive signal and auxiliary signal to be input to the drive coils D and the auxiliary coils E driven simultaneously is adjusted according to the detection result. Accordingly, an optimum driving magnetic field and a auxiliary magnetic field can be formed in the detection space K1, and as a result, the position detecting system 2 and a position detecting method thereof that can detect the position of the LC marker 10 highly accurately by generating the optimum driving magnetic field and auxiliary magnetic field without relying on the apparatus characteristics can be realized.

The signal adjustment unit including the control unit 201 and the drive-coil input-signal adjustment unit 230 adjusts at least one of the phase and amplitude of the drive signal and/or the auxiliary signal by using the evaluation function for evaluating at least one of the phase and amplitude of the drive signal and/or at least one of the phase and amplitude of the auxiliary signal based on the intensity of a magnetic field (for example, the voltage value VS) detected by the sense coil S. The evaluation function includes, for example, the 1a and 1b phase evaluation functions (see Equations (7) and (8)) for calculating the sum of absolute values of the intensity of a magnetic field (the voltage value VS) detected by the sense coil S adjacent to the drive coil D and the auxiliary coil E of the sense coils S, and the second phase evaluation function (see Equation (9)) for calculating the sum of absolute values of the intensity of a magnetic field (the voltage value VS) detected by the sense coils S. When the drive signal is input to the drive coil D and the auxiliary signal is input to the auxiliary coil E, the signal adjustment unit adjusts the phase of the auxiliary signal so that solutions F1 and F2 of the 1a and 1b phase evaluation functions take the minimum value or become less than the predetermined value, and adjusts the phase of the drive signal so that the solution F3 of the second phase evaluation function takes the minimum value or becomes less than the predetermined value. Accordingly, phases of the drive signals and auxiliary signals to be input to the plural drive coils D driven simultaneously and the auxiliary coils E can be aligned.

The evaluation function also includes the first amplitude evaluation function (see Equation (10)) for adding the sum of reciprocal numbers of the intensity of a magnetic field (the voltage value VS) detected by the sense coils S to the sum of absolute values of differences between the intensity of a magnetic field (voltage values) detected by the sense coils S and the preset predetermined value, and the 2a and 2b amplitude evaluation functions (see Equations (11) and (12)) for calculating the absolute value of differences between the intensity of a magnetic field (voltage values) detected by the sense coils S adjacent to the drive coil D and the auxiliary coil E of the sense coils S and a preset predetermined value. When the drive signal and auxiliary signal are respectively input to the drive coil D and the auxiliary signal being selected, the signal adjustment unit adjusts the amplitude of the drive signal and auxiliary signal so that the solution A1 of the first amplitude evaluation function and solutions A2 and A3 of the 2a and 2b amplitude evaluation functions take the minimum value or become less than the predetermined value. Accordingly, amplitudes of the drive signals and auxiliary signals to be input to the plural drive coils D driven simultaneously and the auxiliary coils E can be adjusted.

First Modification

The first, 2a, and 2b amplitude evaluation functions according to the present embodiment can be modified as shown in the following Equations (13) to (15). This is explained below as a first modification of the present embodiment.

$$A1 = |VS\_1r - |VS\_1|| + |VS\_2r - |VS\_2|| + \ldots + |VS\_8r - |VS\_8|| \quad (13)$$

$$A2 = |VS\_1r - |VS\_1|| \quad (14)$$

$$A3 = |VS\_4r - |VS\_4|| \quad (15)$$

The first amplitude evaluation function shown in Equation (13) is a modification of the first amplitude evaluation function shown in Equation (10), and is a function for calculating the sum of absolute values of differences between the voltage values VS_1 to VS_8 read from the respective sense coils S and the ideal values VS_1r to VS_8r thereof. This is the same as the amplitude evaluation function (Equation (3)) according to the first modification of the first embodiment, and thus detailed explanations thereof will be omitted.

Further, the 2a and 2b amplitude evaluation functions shown in Equations (14) and (15) are functions for calculating a difference between the voltage value VS_1 or VS_4 of the detection signals read from the sense coil S_1 or S_4 closest to the auxiliary coil E and the ideal value VS_1r or VS_4r thereof. Therefore, by adjusting the amplitude of the auxiliary signal to be input to the auxiliary coils Ex_1 and Ex_2 so that solutions A2 and A3 of the 2a and 2b amplitude evaluation functions take a minimum value or become less than a predetermined value, the driving magnetic field to be input to the sense coils S_1 to S_4 can be negated accurately, thereby enabling to perform position detection with higher accuracy. Other configurations of the first modification are identical to those of the first embodiment, and thus detailed explanations thereof will be omitted.

Second Modification

The respective evaluation functions exemplified in the present embodiment and the first modification thereof (see Equations (7) to (15)) can be configured such that weights of the sense coils S_1 to S_8 and the drive coils Dx_1 and Dx_2 are preset, and the weighting is taken into consideration, as in the second modification of the first embodiment (see the following Equations (16) to (24)). In Equation (16), α denotes a weight with respect to the drive coil Dx_1 and β denotes a weight with respect to the drive coil Dx_2.

$$A1 = a|VSmax - |VS\_1|| + b|VSmax - |VS\_2|| + c|VSmax - |VS\_3|| + \\ d|VSmax - |VS\_4|| + e|VSmax - |VS\_5|| + f|VSmax - |VS\_6|| + \\ g|VSmax - |VS\_7|| + h|VSmax - |VS\_8|| + \frac{a}{|VS\_1|} + \frac{b}{|VS\_2|} + \\ \ldots + \frac{h}{|VS\_8|} + |\alpha|VDmax - VDx\_1| + \beta|VDmax - VDx\_2|| \quad (16)$$

$$A2 = a|VSmax - |VS\_1|| + b|VSmax - |VS\_2|| + \\ c|VSmax - |VS\_3|| + d|VSmax - |VS\_4|| + e|VSmax - |VS\_5|| + \\ f|VSmax - |VS\_6|| + g|VSmax - |VS\_7|| + h|VSmax - |VS\_8|| \quad (17)$$

$$A3 = a|VSmax - |VS\_1|| + b|VSmax - |VS\_2|| + \\ c|VSmax - |VS\_3|| + d|VSmax - |VS\_4|| + e|VSmax - |VS\_5|| + \\ f|VSmax - |VS\_6|| + g|VSmax - |VS\_7|| + h|VSmax - |VS\_8|| \quad (18)$$

$$A1 = a|VS\_1r - |VS\_1|| + b|VS\_2r - |VS\_2|| + \ldots + h|VS\_8r - |VS\_8|| \quad (19)$$

$$A2 = a|VS\_1r - |VS\_1|| + b|VS\_2r - |VS\_2|| + \ldots + h|VS\_8r - |VS\_8|| \quad (20)$$

$$A3 = a|VS\_1r - |VS\_1|| + b|VS\_2r - |VS\_2|| + \ldots + h|VS\_8r - |VS\_8|| \quad (21)$$

$$F1 = a|VS\_1| + b|VS\_2| \quad (22)$$

$$F2 = c|VS\_3| + d|VS\_4| \quad (23)$$

$$F3 = a|VS\_1| + b|VS\_2| + c|VS\_3| + \\ d|VS\_4| + e|VS\_5| + f|VS\_6| + g|VS\_7| + h|VS\_8| \quad (24)$$

Further, the weight can be changed by the control unit 201 (the signal adjustment unit) based on at least one of the amplitude or phase of the drive signal and/or the auxiliary signal and the intensity of a magnetic field detected by the sense coil S. In this case, for example, when the phase or amplitude of the drive signal or the auxiliary signal is largely changed, the control unit 201 increases the weight with respect to the sense coil S susceptible to the change, and decreases the weight with respect to the sense coil S insusceptible to the change. Accordingly, an evaluation function sensitive to the change of the phase or amplitude can be acquired, thereby enabling to adjust the drive signal and the auxiliary signal with higher accuracy.

Other configurations of the second modification are identical to the first or second embodiment (including modifications thereof) described above, and thus detailed explanations of the second modification will be omitted.

Third Embodiment

Configurations and operations of a position-detection magnetic guiding system 3 according to a third embodiment of the present invention are explained below in detail with reference to the drawings. In the following explanations, constituent elements identical to those of the first or second embodiment of the present invention are denoted by like reference characters and explanations thereof will be omitted.

Figure 13:
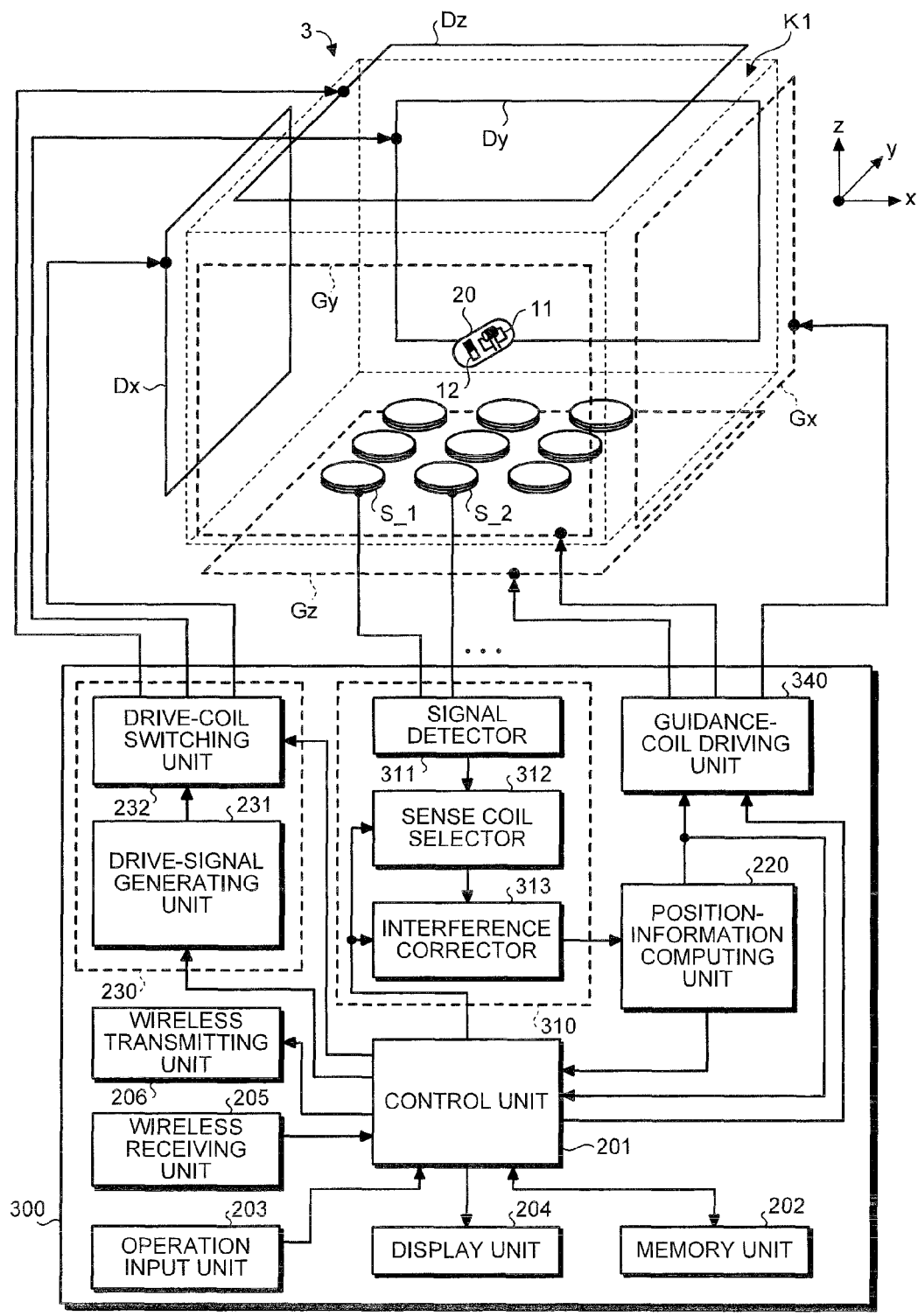
FIG. 13 is a schematic diagram of a schematic configuration of a position-detection magnetic guiding system according to a third embodiment of the present invention.

FIG. 13 is a schematic diagram of a schematic configuration of the position-detection magnetic guiding system 3 according to the present embodiment. As shown in FIG. 13, the position-detection magnetic guiding system 3 includes the detection space K1 for accommodating a subject into which an LC marker 20 as a detected object is inserted, and the external device 200 that detects the position and orientation (posture or direction) of the LC marker 20 in the detection space K1.

LC Marker

Figure 14:
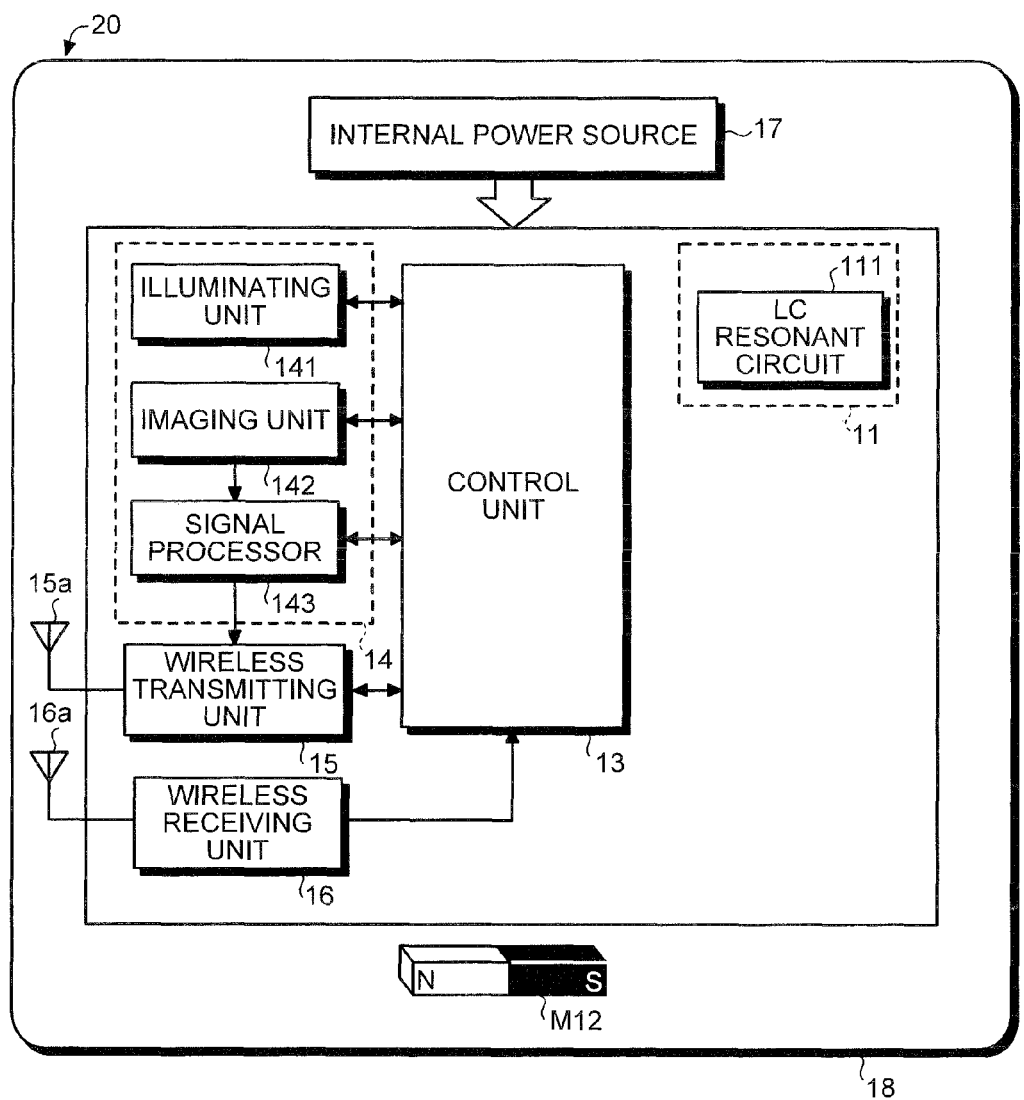
FIG. 14 is a block diagram of a schematic configuration example of an LC marker according to the third embodiment or a fifth embodiment of the present invention.

As shown in FIG. 14, the LC marker 20 according to the present embodiment further includes a permanent magnet M12 in a configuration similar to that of the LC marker 10 (see FIG. 2) of the first embodiment. The permanent magnet M12 is fixed to the casing 18 of the LC marker 20, and generates a propulsive force and a rotative force in the LC marker 20 for changing the position and orientation thereof due to an action of a guidance magnetic field described later. In the present invention, the one that generates the propulsive force and rotative force is not limited to the permanent magnet M12, and it can be changed variously so long as it can generate a magnetic field in which the guidance magnetic field described later operates. Other configurations of the LC marker 20 are identical to those of the LC marker 10 according to the above embodiments.

As in each of the respective embodiments described above, drive coils Dx, Dy, and Dz (hereinafter, D is denoted as the reference character of an arbitrary drive coil) that form a substantially uniform driving magnetic field in a direction different from each other in the detection space K1, and a plurality of sense coils S_1, S_2, . . . , (hereinafter, S is denoted as the reference character of an arbitrary sense coil) that detect the resonant magnetic field generated by the LC resonant circuit 111 in the LC marker 20 are disposed in the detection space K1. Guidance coils G_x, G_y, and G_z (hereinafter, G is denoted as the reference character of an arbitrary guidance coil) that form a guidance magnetic field in a direction different from each other are disposed in the detection space K1. However, in FIG. 13, for clarifying explanations, one of the drive coils D forming a pair is omitted, respectively. In FIG. 13, the sense coils S provided on the ceiling side in the detection space K1 are omitted. Further, configurations of the detection space K1 not particularly shown in FIG. 13 are also identical to those of the detection space K1 explained in the above embodiments.

The guidance coil G respectively form a pair with a guidance coil (not shown) facing each other, putting the detection space K1 therebetween, to form a guidance magnetic field for guiding the LC marker 20 to the target position and orientation in the detection space K1 corresponding to the position and orientation of the LC marker 20 (particularly, the permanent magnet M12). For simplifying the following explanations, attention is paid to the guidance coil G shown in the drawing.

An external device 300 includes the drive-coil input-signal adjustment unit 230, the position-information computing unit 220, and a guidance-coil driving unit 340 in addition to the control unit 201, the memory unit 202, the operation input unit 203, the display unit 204, the wireless receiving unit 205, and the wireless transmitting unit 206.

The drive-coil input-signal adjustment unit 230 is identical to that of the respective embodiments described above. The drive-coil input-signal adjustment unit 230 includes, for example, a drive-signal generating unit 231 that generates a drive signal based on a signal input from the control unit 201, and a drive-coil switching unit 232 that switches the drive coil D to which the drive signal is input according to the control from the control unit 201. The drive-signal generating unit 231 is such that the drive signal generator 233 in the above embodiments is commonly used for the respective drive coils D. Therefore, the drive-signal generating unit 231 can be replaced by the drive signal generators 233a, 233b, . . . provided for each pair of the drive coils D.

A magnetic-field-information acquiring unit 310 includes, for example, a signal detector 311, a sense coil selector 312, and an interference corrector 313.

For example, the sense coil selector 312 selects the sense coil S, from which a detection signal is read by the signal detector 311, is selected from the sense coils S under control of the control unit 201.

The signal detector 311 reads a voltage change generated in the sense coil S regularly or irregularly as a detection signal, and appropriately performs processing such as amplification, band limiting, A/D conversion, and fast Fourier transform with respect to the read detection signal, thereby generating FFT data (or a detection value) indicating information of the magnetic field input to the sense coil S being selected. The detection signal read from each sense coil S is a signal representing magnetic field information such as the intensity and phase of the magnetic field at positions where the respective sense coils S are disposed by a change in voltage. The FFT data is data in which the magnetic field information included in the detection signal read from the sense coil S is converted to information including intensity and phase components. The generated FFT data is input, for example, to the interference corrector 313 via the sense coil selector 312.

The interference corrector 213 removes unnecessary magnetic field components such as an interference magnetic field included in the FFT data from the FFT data input via the sense coil selector 312. The unnecessary magnetic field includes an unnecessary magnetic field generated due to excitation of the guidance coil G by the resonant magnetic field from the LC resonant circuit 111, other than an unnecessary magnetic field generated due to excitation of the drive coil D by the resonant magnetic field from the LC resonant circuit 111. Because the unnecessary magnetic field from the guidance coil G can be removed according to the same method as for the unnecessary magnetic field from the drive coil D explained in the respective embodiments described above, detailed explanations thereof will be omitted.

In the present embodiment, the magnetic-field-information acquiring unit 310 is exemplified; however, the present invention is not limited thereto, and the magnetic-field-information acquiring unit 210 explained in the respective embodiments described above can be used.

The magnetic-field-information acquiring unit 310 inputs the acquired magnetic field information (FFT data) after the unnecessary magnetic field components have been removed to the position-information computing unit 220. The position-information computing unit 220 derives the position and orientation of the LC marker 20 by using the input FFT data and inputs the position and orientation to the control unit 201 as in the respective embodiments described above. The FFT data from the magnetic-field-information acquiring unit 310 can be input to the position-information computing unit 220 via the control unit 201.

The guidance-coil driving unit 340 and the guidance coil G form the guidance magnetic field acting on the permanent magnet M12 fixed to the LC marker 20 to guide the LC marker 20 to the target position and orientation. For example, an operator operates the operation input unit 203 to input the target position and orientation to the control unit 201.

For example, the guidance-coil driving unit 340 acquires information for guiding the LC marker 20 to the target position and orientation (hereinafter, "guidance information") based on the position and orientation of the LC marker 20 derived by the position-information computing unit 220 and the target position and orientation input from the control unit 201, generates one or more signal waveforms of a frequency different from the resonant frequency F0 based on the guidance information, and appropriately generates a guidance signal to be input to one or more guidance coils G by using the signal waveform. The guidance-coil driving unit 340 amplifies the current of the generated guidance signal, and then outputs the amplified guidance signal to the corresponding guidance coil G. Accordingly, the guidance magnetic field for guiding the LC marker 20 to the target position and orientation is formed in the detection space K1.

As the guidance information, various pieces of information such as the target position and orientation, target speed and angular speed of the LC marker, and target acceleration and angular acceleration of the LC marker can be used.

Further, for example, the guidance information can be registered in advance in a lookup table or the like in association with input current position and orientation, and the target position and orientation of the LC marker 20. However, the present invention is not limited thereto, and the guidance information obtained in advance can be managed in the LUT or the like in association with a shift amount and a change amount, expressed by a vector, of posture required for the LC marker 20 obtained based on, for example, the input current position and orientation, and the target position and orientation of the LC marker 20.

Further, other configurations including the evaluation functions such as the phase evaluation function and the amplitude evaluation function (see Equations (1) to (24)) are identical to those of the respective embodiments described above. Therefore, identical effects as those of the above embodiments can be also achieved by the present embodiment. Further, in the present embodiment, further, the interference magnetic field from the guidance coil G can be removed. Therefore, in a system capable of guiding the LC marker 20 by magnetism (guidance magnetic field), because the magnetic field formed in the detection space K1 is actually detected, and at least one of the phase and amplitude of the drive signal to be input to the drive coils D driven simultaneously is adjusted according to the detection result, an optimum driving magnetic field can be formed in the detection space K1. As a result, the position-detection magnetic guiding system 3 and a position-detection magnetic guiding method thereof that can detect the position of the LC marker 20 highly accurately by generating the optimum driving magnetic field, without relying on the apparatus characteristics can be realized.

Needless to mention, modifications can be also made in the present embodiment as in the above embodiments.

The above embodiments are only examples for carrying out the present invention. The present invention is not limited to these embodiments and various changes according to specifications or the like are within the scope of the invention. In addition, it is obvious from the above description that various other embodiments can be made within the scope of the present invention.

For example, the position detecting method according to the present invention is a position detecting method for detecting a position of a detected object, which is inserted into a detection space where at least two drive coils that form a driving magnetic field and an auxiliary coil that generates a auxiliary magnetic field for negating the driving magnetic field generated by the drive coils in a part of the space are disposed, to generate a resonant magnetic field corresponding to the driving magnetic field. The position detecting method can include: a first detection step of detecting the magnetic field formed in the detection space by inputting a drive signal respectively to the at least two drive coils, and the magnetic field formed in the detection space by inputting a drive signal and an auxiliary signal respectively to at least one of the two drive coils and the auxiliary coil, by at least one sense coil in a state with the detected object not being inserted into the detection space; an adjustment step of adjusting at least one of phase and amplitude of the drive signal and the auxiliary signal based on the magnetic field detected at the first detection step; a drive step of forming the driving magnetic field and the auxiliary magnetic field in the detection space by inputting the drive signal and auxiliary signal with at least one of the phase and amplitude thereof being adjusted at the adjustment step, respectively, to the drive coil and auxiliary coil in a state with the detected object being inserted into the detection space; a second detection step of detecting the magnetic field in the detection space at the time of forming the driving magnetic field and auxiliary magnetic field in the detection space at the drive step, by at least one sense coil; and a position deriving step of deriving a position of the detected object based on the magnetic field detected at the second detection step.

In the position detecting method described above, at the adjustment step, at least one of the phase and amplitude of the drive signal and/or auxiliary signal can be adjusted by using an evaluation function for evaluating at least one of the phase and amplitude of the drive signal and/or auxiliary signal based on the intensity of a magnetic field detected by the sense coil.

In the position detecting method described above, at the adjustment step, a first phase evaluation function for calculating the sum of absolute values of an intensity of a magnetic field detected by the sense coil S adjacent to the drive coil and the auxiliary coil of the sense coils, and a second phase evaluation function for calculating the sum of absolute values of an intensity of a magnetic field detected by the sense coils S can be used, to adjust the phase of the auxiliary signal so that a solution of the first phase evaluation function takes a minimum value or becomes less than a predetermined value and the phase of the drive signal can be adjusted so that a solution of the second phase evaluation function takes a minimum value or becomes less than a predetermined value, when the drive signal is input to the drive coil and the auxiliary signal is input to the auxiliary coil.

In the position detecting method described above, at the adjustment step, a first amplitude evaluation function for adding the sum of reciprocal numbers of the intensity of a magnetic field detected by the sense coils S to the sum of absolute values of differences between the intensity of a magnetic field detected by the sense coils S and a preset predetermined value, and a second amplitude evaluation function for calculating an absolute value of differences between the intensity of a magnetic field detected by the sense coils S adjacent to the drive coil and the auxiliary coil of the sense coils S and a preset predetermined value can be used, to adjust the amplitudes of the drive signal and the auxiliary signal so that the first amplitude evaluation function takes a minimum value or becomes less than a predetermined value and the second amplitude evaluation function becomes less than a predetermined value, when the drive signal is input to the drive coil and the auxiliary signal is input to the auxiliary coil.

Fourth Embodiment

Configurations and operations of a position detecting system 4 according to a fourth embodiment of the present invention are explained in detail with reference to the drawings. In the present embodiment, in the position detecting system 4 that decreases components of a driving magnetic field DMF to be input to respective sense coils 1214 by using auxiliary coils 1244a and 1244b described later, an optimum intensity of a auxiliary magnetic field SMF is obtained for each sense coil 1214, and components other than a resonant magnetic field RMF included in a detection signal Sdet read from the respective sense coils 1214 is canceled based on an actual measurement value, thereby detecting the position and orientation of a resonant-magnetic-field generation source (particularly, the LC resonant circuit 111 in the LC marker 10) with higher accuracy. In the following explanations, constituent elements identical to those of the above embodiments of the present invention are denoted by like reference characters and explanations thereof will be omitted.

Configuration of Position Detection

Figure 15:
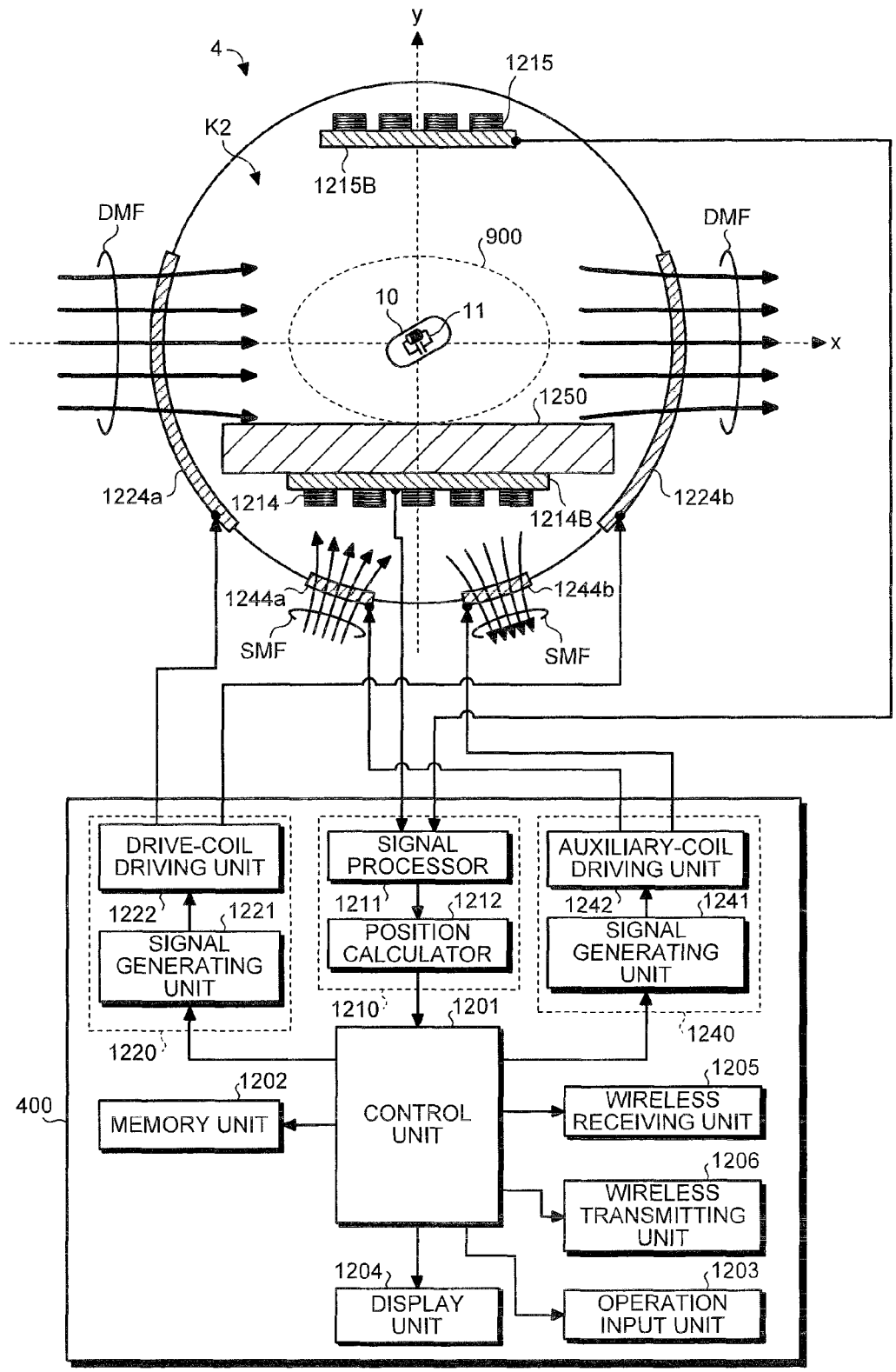
FIG. 15 is a schematic diagram of a schematic configuration of a position detecting system according to the fourth embodiment of the present invention.

FIG. 15 is a schematic diagram of a schematic configuration of the position detecting system 4 according to the present embodiment. As shown in FIG. 15, the position detecting system 4 includes a cylindrical detection space K2 for accommodating the subject 900 into which the LC marker 10 as a body-insertable apparatus is inserted, and an external device 400 that detects the position and orientation (posture) of the LC marker 10 in the detection space K2.

LC Marker

As shown in FIG. 2, the LC marker 10 according to the present embodiment includes the resonant-magnetic-field generating unit 11 (see FIG. 15) that generates a resonant magnetic field for position detection. The resonant-magnetic-field generating unit 11 includes the LC resonant circuit 111 including a capacitor (C) and an inductor (L) connected in parallel, and is excited by a magnetic field for position detection (hereinafter, "driving magnetic field") DMF of a frequency substantially equal to the resonant frequency F0 input from outside to emit a resonant magnetic field (RMF) of the resonant frequency F0. The resonant frequency F0 is the resonant frequency of the LC resonant circuit 111 determined by the capacitor (C) and the inductor (L) connected in parallel. Other configurations of the LC marker 10 are identical to those of the LC marker 10 according to the first and second embodiments described above.

Detection Space

Explanations are continued while referring back to FIG. 15. Drive coils 1224a and 1224b that form a substantially uniform driving magnetic field DMF in the detection space K2, a plurality of sense coils 1214 and 1215 that detect the resonant magnetic field generated by the LC resonant circuit 111 in the LC marker 10, circuit boards 1214B and 1215B respectively mounted with a plurality of sense coils 1214 and 1215, and auxiliary coils 1244a and 1244b disposed near the sense coils 1214 particularly susceptible to the driving magnetic field DMF are disposed in the detection space K2. The circuit board 1214B is installed, for example, below a table 1250 on which the subject 900 having the LC marker 10 inserted therein is lying.

The drive coils 1224a and 1224b opposite to each other, putting the detection space K2 therebetween, form a pair, and generate, for example, the substantially uniform driving magnetic field DMF including magnetic field lines extending in a direction of an x-axis in the detection space K2. Drive coils that generate the substantially uniform driving magnetic field DMF including magnetic field lines extending in a direction different from the x-axis in the detection space K2 can be provided separately in the detection space K2. Accordingly, a resonant magnetic field can be generated with a stable intensity in the LC resonant circuit 111, even if the LC resonant circuit 111 in the LC marker 10 (particularly, the inductor (L)) turns to any direction in the detection space K2. As a result, position detection accuracy of the LC marker 10 can be improved. In the following explanations, 1224 is denoted as the reference numeral of an arbitrary drive coil.

The respective sense coils 1214 and 1215 are magnetic sensors including a coil capable of detecting, for example, a field intensity in the y-axis direction and the direction. However, the sense coils 1214 and 1215 are not limited thereto, and can be formed by using a magnetic sensor including, for example, a magnetoresistive element or a magnetic impedance element (MI element). Further, the respective sense coils 1214 and 1215 can be constituted by a 3-axis magnetic sensor including three coils for detecting the x-axis, y-axis, and z-axis, respectively.

The sense coils 1214 or 1215 are disposed at positions insusceptible to the driving magnetic field DMF and capable of easily detecting the resonant magnetic field generated by the LC resonant circuit 111. In the present embodiment, an example in which the sense coils 1214 are two-dimensionally disposed on a bottom face of the circuit board 1214B disposed below the detection space K2 (on an x-y plane below the detection space K2) is shown, and an example in which the sense coils 1215 are two-dimensionally disposed on an upper face of the circuit board 1215B disposed above the detection space K2 (on an x-y plane above the detection space K2) is shown.

Figure 16A:
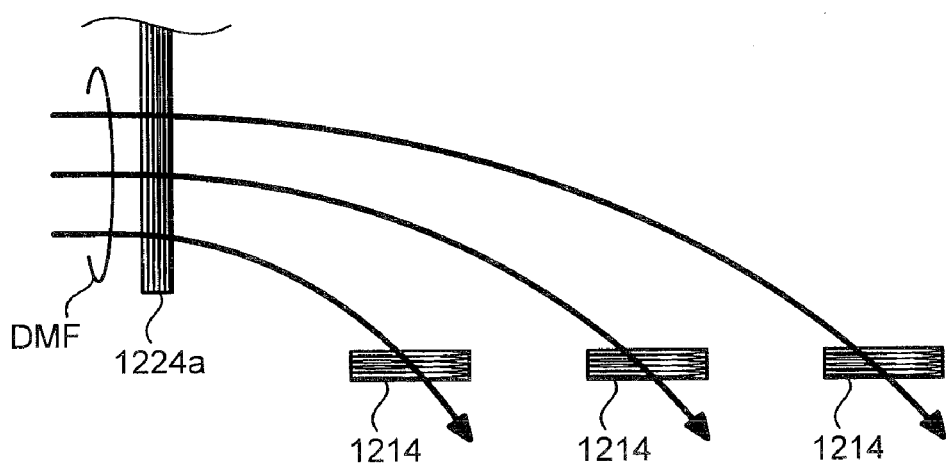
FIGS. 16A and 16B depict a relation between a driving magnetic field generated by a drive coil and a sense coil in the fourth or fifth embodiment of the present invention.
Figure 16B:
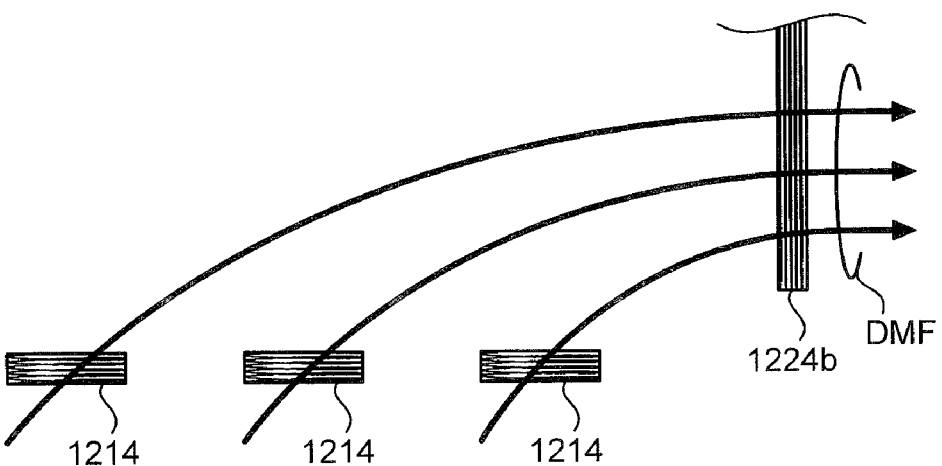

For example, the sense coils 1214 disposed below the detection space K2 of the sense coils 1214 and 1215 are disposed adjacent to the drive coil 1224 as compared with the sense coils 1215 disposed above the detection space K2. As shown in FIG. 16A or 16B, when the sense coils 1214 are disposed adjacent to the drive coil 1224, the driving magnetic field DMF formed by the drive coil 1224 is strongly input to the respective sense coils 1214. FIG. 16A depicts a relation between the driving magnetic field DMF generated by the drive coil 1224a and the sense coil 1214 according to the present embodiment, and FIG. 16B depicts a relation between the driving magnetic field DMF generated by the drive coil 1224b and the sense coil 1214 according to the present embodiment.

In the present embodiment, auxiliary coils 1244a and 1244b that output the auxiliary magnetic field SMF for negating the driving magnetic field DMF to be input to the respective sense coils 1214 are provided. At the time of reading a signal from any one of the sense coils 1214 (hereinafter, "detection signal Sdet"), the auxiliary coils 1244a and 1244b emit the auxiliary magnetic field SMF for negating the driving magnetic field DMF to be input to the corresponding sense coil 1214, thereby decreasing the components of the driving magnetic field DMF to be input to the respective sense coils 1214. In the following explanations, 1244 is denoted as the reference numeral of an arbitrary auxiliary drive coil.

Figure 17A:
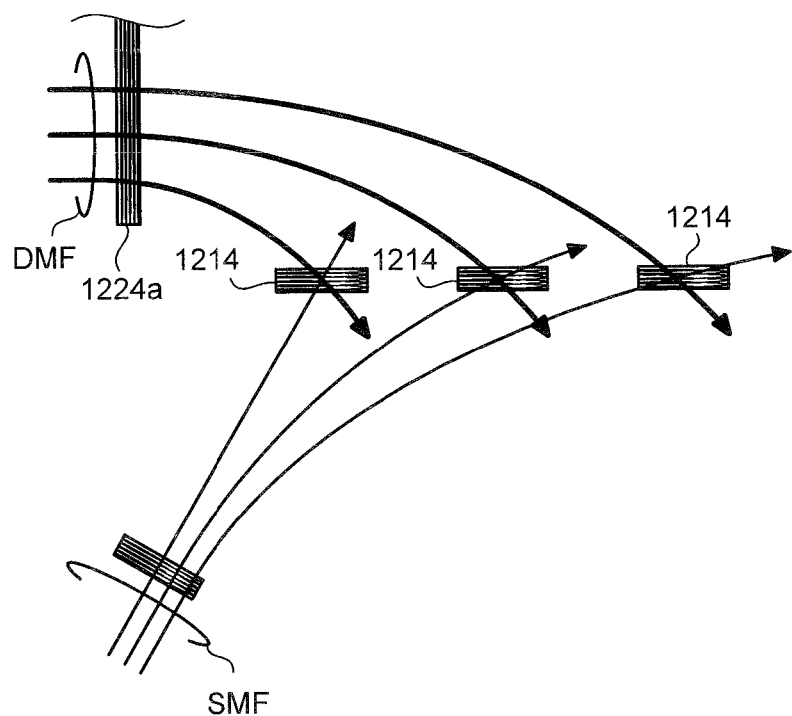
FIGS. 17A and 17B depict a relation among a driving magnetic field generated by a drive coil, a auxiliary magnetic field generated by an auxiliary coil, and a sense coil in the fourth or fifth embodiment of the present invention.
Figure 17B:
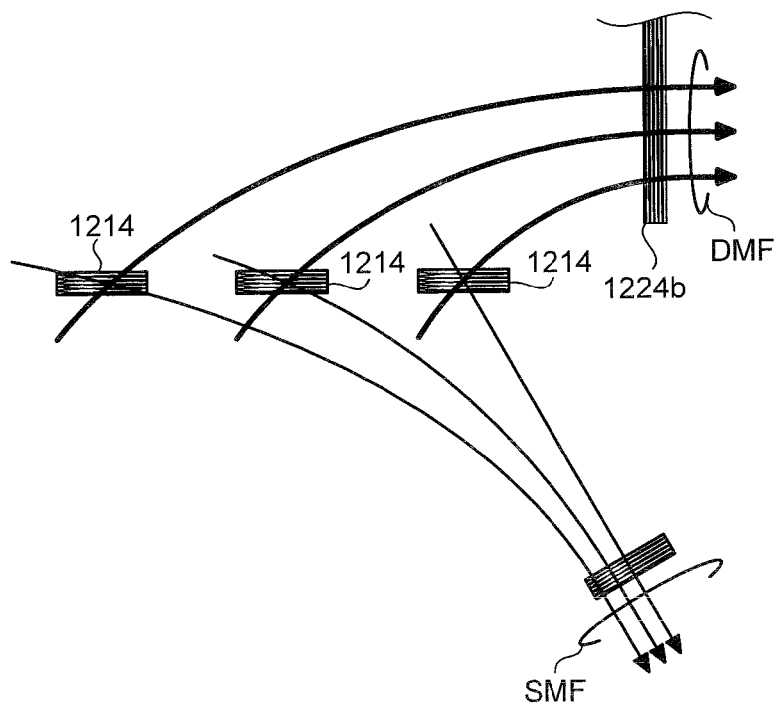

However, an influence of the driving magnetic field DMF on the respective sense coils 1214 changes according to the positional relation between the drive coil 1224 and the sense coil 1214. The influence generally becomes stronger in the sense coil 1214 adjacent to the drive coil 1224. Therefore, in the present embodiment, as shown in FIGS. 15, and 17A or 17B, the auxiliary coil 1244 is disposed so that the auxiliary magnetic field SMF is input most strongly to the sense coil 1214 disposed closest to the drive coil 1224 of the sense coils 1214. At this time, it is desired that the direction of the magnetic field lines to be output from the respective auxiliary coils 1244 is directed to the sense coil 1214 closest to the drive coil 1224. Accordingly, the field intensity of the auxiliary magnetic field SMF generated for negating the driving magnetic field DMF can be suppressed. FIG. 17A depicts a relation among the driving magnetic field DMF generated by the drive coil 1224a, the auxiliary magnetic field SMF generated by the auxiliary coil 1244a, and the sense coil 1214; and FIG. 17B depicts a relation among the driving magnetic field DMF generated by the drive coil 1224b, the auxiliary magnetic field SMF generated by the auxiliary coil 1244b, and the sense coil 1214 in the present embodiment.

A case that the auxiliary coil 1244 is disposed on the sense coil 1214 side is exemplified. However, the present invention is not limited thereto, and the auxiliary coil 1244 can be provided also on the sense coil 1215 side to decrease the driving magnetic field DMF to be input to the respective sense coils 1215.

External Device

The external device 400 includes a driving-magnetic-field generating unit 1220 that outputs a signal used for driving the drive coils 1224 (hereinafter "drive signal"), an auxiliary-magnetic-field generating unit 1240 that outputs the auxiliary magnetic field SMF used for driving the auxiliary coils 1244 (hereinafter "auxiliary signal"), a position deriving unit 1210 that derives the position and direction of the LC marker 10 from a voltage change (the detection signal Sdet) acquired by the sense coils 1214, a control unit 1201 that controls respective units in the external device 400, a memory unit 1202 that stores various programs to be executed at the time of controlling the respective units by the control unit 1201, parameters and the like, an operation input unit 1203 for an operator to input various operation instructions to the LC marker 10, a display unit 1204 that displays information of the position and orientation of the LC marker 10 (hereinafter, simply "position information and the like") and in-vivo information acquired from the LC marker 10 by images (including video pictures) and sounds, a wireless receiving unit 1205 that receives the in-vivo information and the like transmitted from the LC marker 10 as a wireless signal, and a wireless transmitting unit 1206 that transmits various operation instructions such as an imaging instruction to the LC marker 10 as a wireless signal.

The control unit 1201 is constituted by, for example, a CPU or an MPU, and controls the respective units in the external device 400 according to the program and parameter read from the memory unit 1202. Specifically, for example, the control unit 1201 causes a signal processor 1211 to derive magnetic field information based on the detection signal read from the sense coils 1214 in a state with a drive signal being input to the drive coils 1224 by the driving-magnetic-field generating unit 1220 and an auxiliary signal being input to the auxiliary coils 1244 by the auxiliary-magnetic-field generating unit 1240. Accordingly, the control unit 1201 causes the position deriving unit 1210 to derive the position of the LC marker 10 by using the acquired magnetic field information, the phase stored in the memory unit 1202 or the like, and information of a combined magnetic field stored in the memory unit 1202 or the like. The memory unit 202 is constituted by, for example, a RAM (Random Access Memory) or a ROM (Read Only Memory), and holds the programs to be executed at the time of controlling the respective units by the control unit 201 and parameters. The in-vivo image received from the LC marker 10 and position information such as the position and orientation of the LC marker 10 derived by the position deriving unit 1210 are appropriately stored in the memory unit 1202.

The operation input unit 1203 includes, for example, a keyboard, a mouse, a numerical keypad, and a joystick, so that an operator inputs various operation instructions with respect to the LC marker 10 such as an imaging instruction (including an in-vivo information acquiring instruction or the like), and various operation instructions with respect to the external device 400 such as a shift instruction at the time of guiding the LC marker 10, a screen switching instruction for switching a screen for display on the display unit 1204. When the LC marker 10 includes a plurality of the imaging units 142 and images acquired by the LC marker 10 are displayed on the display unit 1204 on a real-time basis, a screen switching function for display on the display unit 1204 can be provided.

The display unit 1204 is a display device such as a liquid crystal display, a plasma display, or LED array, and displays position information of the LC marker 10 and in-vivo information such as in-vivo images transmitted from the LC marker 10. The display unit 1204 can have a sound reproduction function using a speaker or the like. The display unit 1204 notifies the operator by sounds of various pieces of operation guidance and information such as a remaining amount of battery of the LC marker 10 (including an alarm or the like) by using the sound reproduction function.

The wireless receiving unit 1205 is connected to a receiving antenna (not shown) such as a dipole antenna disposed adjacent to the detection space K2. For example, the receiving antenna is disposed near the detection space K2. The wireless receiving unit 1205 receives the in-vivo image and the like transmitted from the LC marker 10 as a wireless signal via the receiving antenna, performs various types of processing such as filtering, down-conversion, demodulation, and decoding with respect to the received signal, and then outputs the signal to the control unit 1201. That is, the wireless receiving unit 1205 also functions as an in-vivo-image information receiving unit (for example, an image receiving unit) that receives the in-vivo information (for example, in-vivo images) transmitted from the LC marker 10.

The wireless transmitting unit 1206 is connected to a transmitting antenna (not shown) such as a dipole antenna disposed adjacent to the detection space K2. For example, the transmitting antenna is disposed near the detection space K2. The wireless transmitting unit 1206 performs various types of processing such as superposition on the reference frequency signal for transmission, modulation, and up-conversion with respect to signals such as various operation instructions to the LC marker 10 input from the control unit 1201, and transmits signals from a transmitting antenna 15a to the LC marker 10 as radio signals.

The driving-magnetic-field generating unit 1220 includes a signal generating unit 1221 and a drive-coil driving unit 1222. The signal generating unit 1221 calculates a signal waveform having a frequency substantially equal to the resonant frequency F0 of the LC resonant circuit 111 in the LC marker 10 according to the control signal input from the control unit 1201, and generates a drive signal having the signal waveform to output the drive signal to the drive-coil driving unit 1222.

The drive-coil driving unit 1222 amplifies the current of the drive signal input from the signal generating unit 1221, and inputs the amplified drive signal to the drive coil 1224. The drive coil 1224, to which the amplified drive signal has been input, emits a magnetic field of the frequency substantially equal to the resonant frequency F0 held by the LC resonant circuit 111 in the LC marker 10, thereby forming the driving magnetic field DMF that excites the LC resonant circuit 111 in the detection space K2. A current amplification factor by the drive-coil driving unit 1222 is set, taking into consideration processing capacity (for example, a dynamic range) of the sense coil 1214 and the signal processor 1211 and an S/N ratio of the detection signal Sdet acquired by the sense coil 1214.

The auxiliary-magnetic-field generating unit 1240 includes a signal generating unit 1241 and an auxiliary-coil driving unit 1242. The signal generating unit 1241 calculates a signal waveform having a frequency substantially equal to the resonant frequency F0 of the LC resonant circuit 111 in the LC marker 10 and having a phase shifted approximately by 180 degrees from the drive signal, according to the control signal input from the control unit 1201, and generates an auxiliary signal having the signal waveform to output the auxiliary signal to the auxiliary-coil driving unit 1242.

The auxiliary-coil driving unit 1242 amplifies the current of the auxiliary signal input from the signal generating unit 1241, and inputs the amplified auxiliary signal to the auxiliary coil 1244. The auxiliary coil 1244, to which the amplified auxiliary signal has been input, emits a magnetic field of the frequency substantially equal to the resonant frequency F0 held by the LC resonant circuit 111 in the LC marker 10, thereby emitting the auxiliary magnetic field SMF for negating the driving magnetic field DMF input to the sense coil 1214 to be driven.

The position deriving unit 1210 performs predetermined processing with respect to the information of the magnetic field included in the detection signal Sdet read from the sense coil 1214 (hereinafter, "magnetic field information") to derive the position and orientation of the LC marker 10 (position information and the like) substantially on a real-time basis.

The position deriving unit 1210 includes, for example, the signal processor 1211 and a position calculator 1212. The signal processor 1211 reads the detection signal Sdet respectively from the sense coils 1214. The signal processor 1211 appropriately performs amplification, band limiting, A/D conversion, and FFT with respect to the read detection signal Sdet to output the processed detection signal Sdet (FFT data) to the position calculator 1212. The signal processor 1211 reads the detection signal Sdet (FFT data) from the sense coil 1214 regularly, performs the signal processing, and outputs the processed detection signal to the position calculator 1212. The detection signals Sdet output from the respective sense coils 1214 are signals expressing the magnetic field information such as an intensity and a phase of the magnetic field at positions where the respective sense coils 1214 are disposed by a voltage.

The position calculator 1212 performs predetermined arithmetic processing with respect to the detection signal Sdet input from the signal processor 1211 to derive the current position information and the like of the LC marker 10 from the magnetic field information included in the detection signal Sdet. The position calculator 1212 outputs the derived position information and the like to the control unit 1201.

Figure 18:
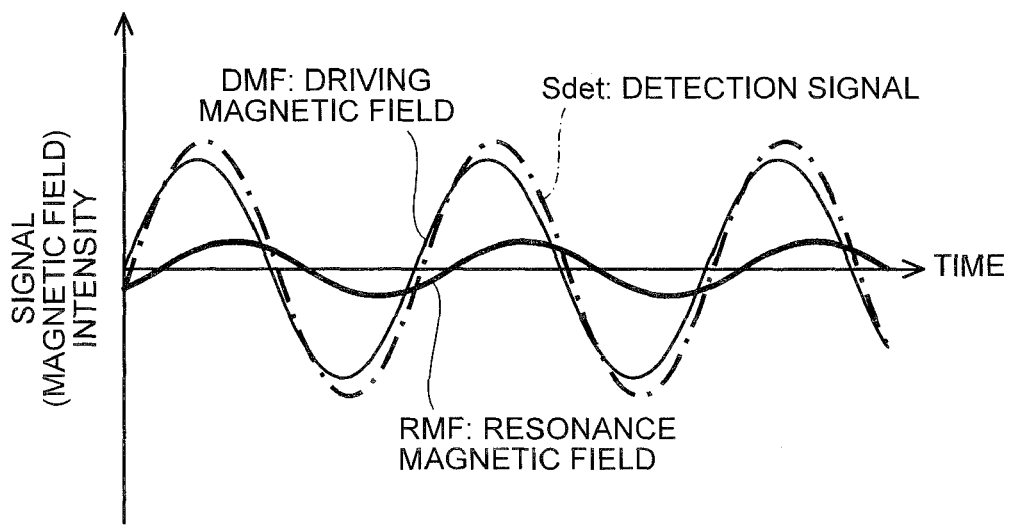
FIG. 18 depicts a relation among a driving magnetic field, a detection signal, and a resonant magnetic field in the fourth or fifth embodiment of the present invention when the driving magnetic field is generated.

For example, as shown in FIG. 18, when the auxiliary coil 1244 is not provided, the detection signals Sdet read from the respective sense coils 1214 include the component of the driving magnetic field DMF of a frequency substantially equal to the resonant frequency F0, other than the component of the resonant magnetic field RMF (resonant magnetic field component) emitted from the LC resonant circuit 111. The component of the driving magnetic field DMF is an unnecessary magnetic field component at the time of deriving the position information and the like. Therefore, the position calculator 1212 cannot derive the accurate position information and the like of the LC marker 10 (particularly, the LC resonant circuit 111) directly from the detection signal Sdet read from the respective sense coils 1214. FIG. 18 depicts a relation among the driving magnetic field DMF, the detection signal Sdet, and the resonant magnetic field RMF when the driving magnetic field DMF is generated in the present embodiment.

Figure 19:
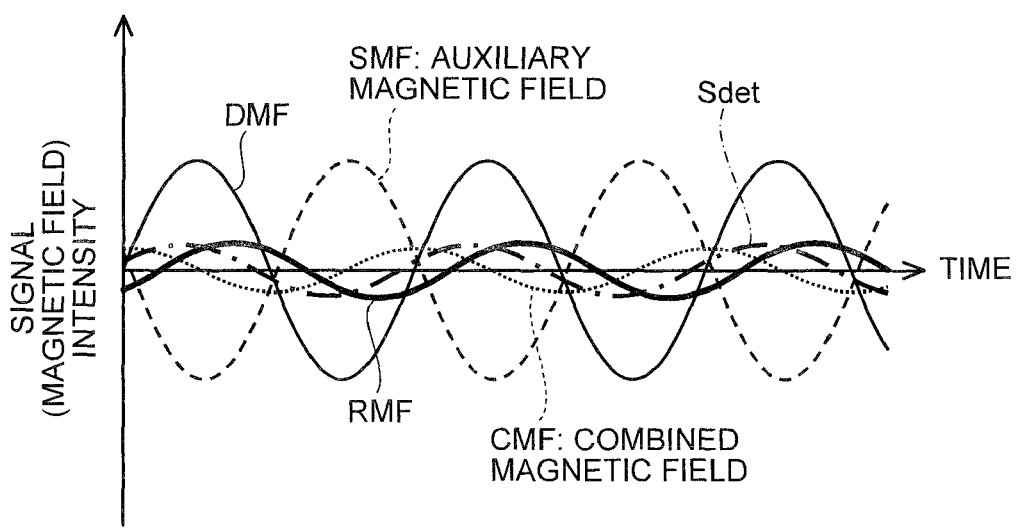
FIG. 19 depicts a relation among a driving magnetic field, a auxiliary magnetic field, a combined magnetic field, a detection signal, and a resonant magnetic field in the fourth or fifth embodiment of the present invention when the driving magnetic field and the auxiliary magnetic field are generated.

For example, as shown in FIG. 19, even if the auxiliary coil 1244 is used, unless the driving magnetic field DMF to be input to the sense coil 1214 is completely negated by the auxiliary magnetic field SMF, the detection signal Sdet to be input to the position calculator 1212 includes the component of a combined magnetic field CMF in which the driving magnetic field DMF and the auxiliary magnetic field SMF are combined as an unnecessary magnetic field component, other than the resonant magnetic field RMF. Therefore, the accurate position information and the like of the LC marker 10 (particularly, the LC resonant circuit 111) cannot be derived unless the component of the combined magnetic field CMD is removed from the detection signal Sdet as described above. FIG. 19 depicts a relation among the driving magnetic field DMF, the auxiliary magnetic field SMF, the combined magnetic field CMF, the detection signal Sdet, and the resonant magnetic field RMF when the driving magnetic field DMF and the auxiliary magnetic field SMF are generated in the present embodiment.

In addition, generally, because there are impedance, parasitic capacity and the like in an electrical path and the like between the drive-coil driving unit 1222 and the drive coil 1224, the phase of the driving magnetic field DMF generated by the drive coil 1224 is delayed from the phase of the drive signal output from the drive-coil driving unit 1222. That is, a phase difference is generated between the drive signal and the driving magnetic field. Because such a phase difference causes an error in a position detection result, it is desired to eliminate such a phase difference.

Therefore, in the present embodiment, a process of removing the component of the combined magnetic field CMF is performed with respect to the detection signal Sdet output from the signal processor 1211 and a process of removing a phase difference between the driving magnetic field DMF and the drive signal and is performed. A process including these processes is referred to as "two-stage calibration process". Accordingly, the resonant magnetic field information can be extracted from the detection signal Sdet according to an actually formed magnetic field, thereby enabling to perform position detection with higher accuracy.

At the time of performing the two-stage calibration process, in the present embodiment, for example, as a pre-calibration process, the driving magnetic field DMF is formed in the detection space K2 by driving the drive coils 1224 in a state with the LC marker 10 (that is, the LC resonant circuit 111) not being inserted into the detection space K2, the driving magnetic field DMF actually formed in the detection space K2 is detected in this state, and a phase (for example, a phase based on the drive signal: corresponding to first calibration information described later) is acquired from the acquired information of the driving magnetic field DMF. At the time of acquiring the first calibration information, because only the driving magnetic field DMF is generated, the phase of the magnetic field at the positions of the respective sense coils 1214 and the phase of the magnetic field in the detection space K2 become the same. As the pre-calibration process, further, the drive coils 1224 and the auxiliary coils 1224 are driven to form the driving magnetic field DMF and the auxiliary magnetic field SMF in the detection space K2 in the state with the LC marker 10 (that is, the LC resonant circuit 111) not being inserted into the detection space K2, and the magnetic field actually formed in the detection space K2 (the combined magnetic field CMF) is detected in this state, to derive the magnetic field information not including the component of the resonant magnetic field RMF (information of the combined magnetic field CMF: corresponding to second calibration information described later). In the two-stage calibration process, the first and second pieces of calibration information held, for example, in the memory unit 1202 or the like are read to perform a process of removing the first and second pieces of calibration information from the magnetic field information included in the detection signal Sdet. Accordingly, the component of the resonant magnetic field RMF can be extracted from the detection signal Sdet.

The phase of the magnetic field (the combined magnetic field CMF) not including the component of the resonant magnetic field RMF (first calibration information) can be derived, for example, from the detection signal Sdet read from the sense coils 1214 or from the detection signal read from a magnetic field sensor (not shown) disposed separately in the detection space K2. However, for example, the position deriving unit 1210 can be used for processing with respect to the detection signal read from the magnetic field sensor. The magnetic field information not including the component of the resonant magnetic field RMF (second calibration information) can be derived from the detection signal Sdet read from, for example, the sense coils 1214.

At the time of acquiring the second calibration information and at the time of performing the position detection, the phase of the magnetic field changes at the positions of the sense coils 1214 due to the auxiliary magnetic field SMF generated from the auxiliary coil 1244. However, because the auxiliary coil 1244 is small, the magnetic field does not reach the detection space K2 from the auxiliary coil 1244, and the phase of the magnetic field becomes substantially the same as that of the driving magnetic field DMF. Therefore, the phase of the magnetic field generated in the detection space K2 can be detected by the first calibration, and the phase of the combined magnetic field CMF at the positions of the sense coils 1214 can be detected by the second calibration.

The position information and the like derived by the position calculator 1212 by using the resonant magnetic field information extracted from the detection signal Sdet according to the processes described above is input to the control unit 1201. The control unit 1201 displays information of the current position and orientation of the LC marker 10 by using the input position information and the like. Accordingly, an operator can confirm the current position and orientation of the LC marker 10 based on the information displayed on the display unit 1204.

Further, the operator can input an operation instruction for operating the position and orientation of the LC marker 10 by using the operation input unit 1203. The operator can also input an acquisition instruction of the in-vivo information to the LC marker 10 by using the operation input unit 1203.

Position Deriving Procedure

Figure 20:
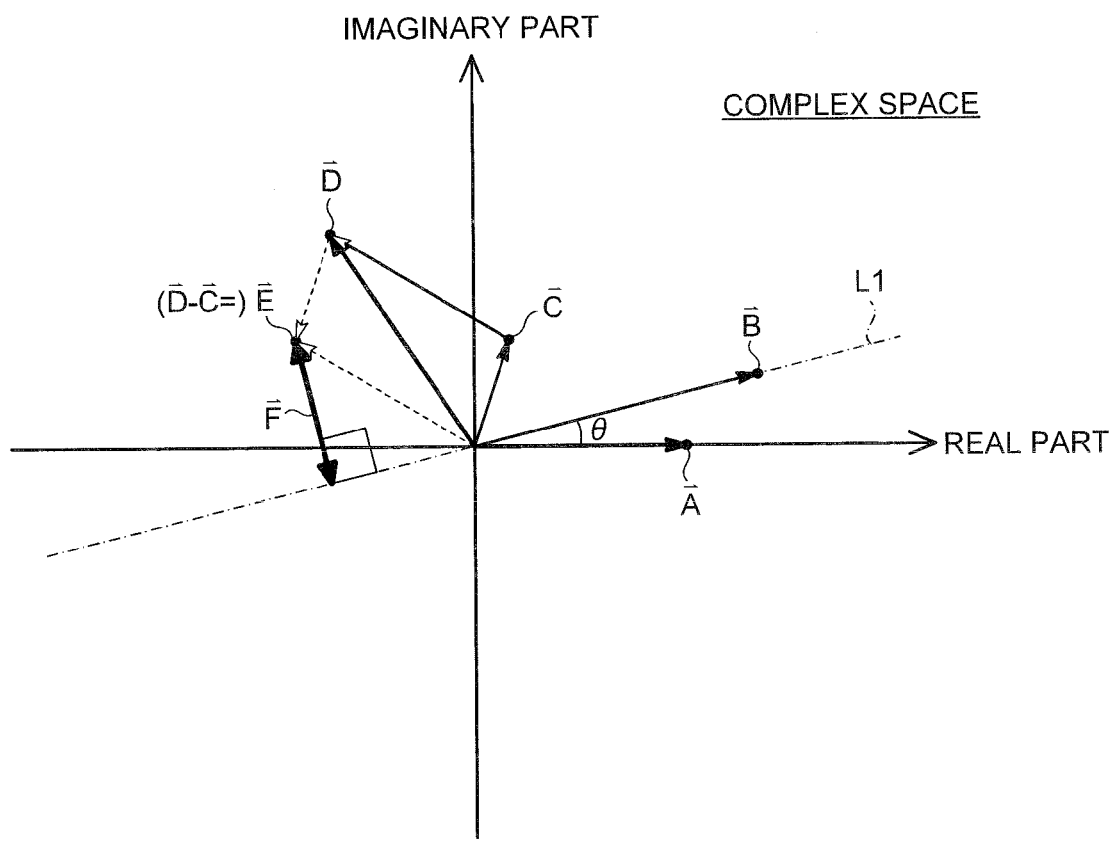
FIG. 20 is an explanatory diagram of contents of procedures for deriving a position in the fourth embodiment of the present invention.

A position deriving procedure of the present embodiment is explained in detail with reference to the drawings. FIG. 20 is an explanatory diagram of contents of procedures for deriving the position in the present embodiment.

In the present embodiment, as shown in FIG. 20, the phase of the driving magnetic field DMF formed at the positions of the respective sense coils 1214 is actually measured when the driving magnetic field DMF is generated in the state with the LC marker 10 (particularly, the LC resonant circuit 111) not being inserted, according to the pre-calibration process, which is stored in the memory unit 1202 or the like (phase storage unit), for example, as the first calibration information. The intensity and phase of the drive signal to be input to the drive coils 1224 from the driving-magnetic-field generating unit 1220 are indicated by, for example, a complex vector 'A' shown in FIG. 20, whereas the intensity and phase of the driving magnetic field DMF included in the detection signal Sdet read from the signal processor 1211 are indicated by, for example, a complex vector 'B' shown in FIG. 20. In FIG. 20, a driving-magnetic-field component line L1 indicating an inclination θ of the complex vector 'B' with respect to the complex vector 'A' indicates a phase difference of the driving magnetic field DMF with respect to the drive signal, that is, the phase of the driving magnetic field DMF based on the phase of the drive signal.

Further, in the present embodiment, the intensity and phase of the combined magnetic field CMF formed at the positions of the respective sense coils 1214 are acquired when the driving magnetic field DMF and the auxiliary magnetic field are generated in the state with the LC marker 10 (particularly, the LC resonant circuit 111) not being inserted, according to the pre-calibration process, which is stored in the memory unit 1202 or the like (combined-magnetic-field information storage unit), for example, as the second calibration information. The intensity and phase of the combined magnetic field CMF are indicated by, for example, a complex vector 'C' shown in FIG. 20.

In the two-stage calibration process in the actual position deriving process, if it is assumed that the magnetic field information included in the detection signal Sdet read from a certain sense coil 1214 is a complex vector 'D' in FIG. 20, the second calibration information (the complex vector 'C') is subtracted from the complex vector 'D' according to vector operation. Accordingly, the component of the combined magnetic field CMF (the complex vector 'C') is removed from the magnetic field information included in the detection signal Sdet (complex vector 'E'=complex vector 'D'−complex vector 'C'). Subsequently, the complex vector 'E' acquired by the vector operation is projected to the driving-magnetic-field component line L1 indicating the phase of the driving magnetic field DMF, thereby deriving a cosine component of the complex vector 'E' with respect to the driving-magnetic-field component line L1. Accordingly, components of the resonant magnetic field RMF (a complex vector 'F') can be extracted from the detection signal Sdet.

By performing the process descried above, components of the resonant magnetic field RMF (the complex vector 'F') can be extracted more accurately, and as a result, more accurate information such as the position and orientation of the LC marker 10 can be derived.

Position Detection Operation

Figure 21:
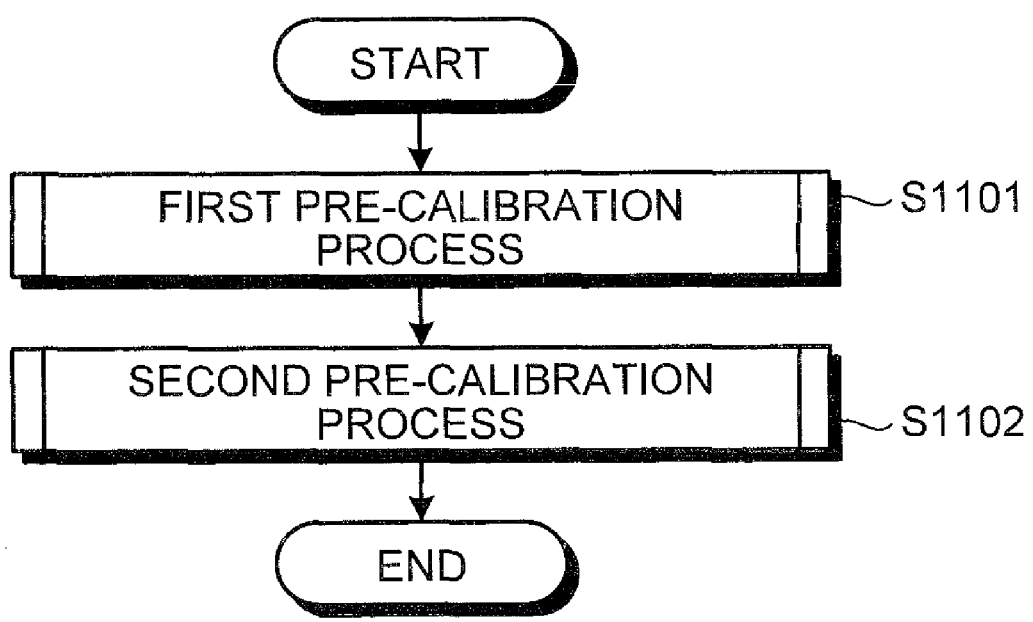
FIG. 21 is an explanatory diagram of a concept of a position detection operation according to the fourth embodiment of the present invention.
Figure 22:
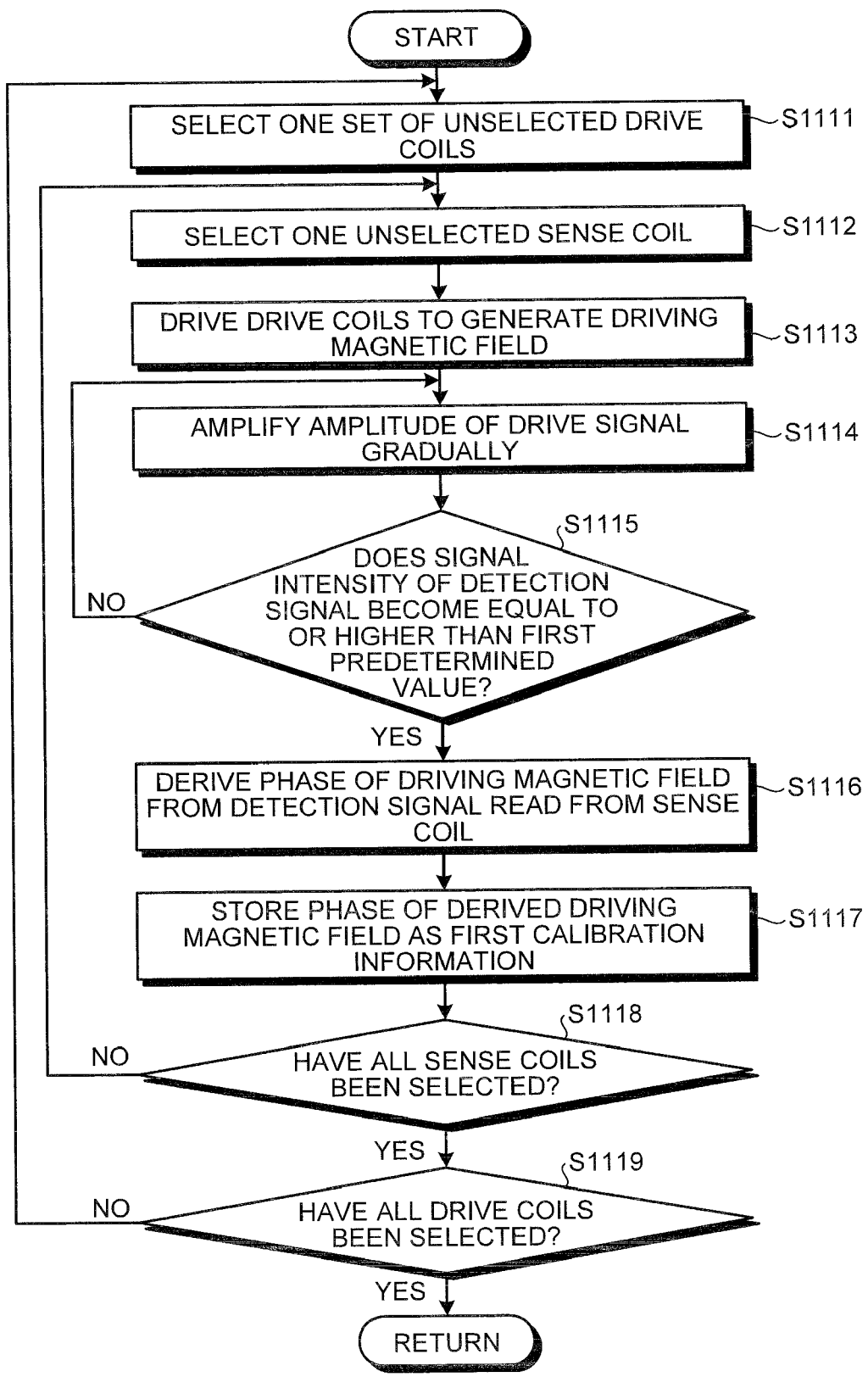
FIG. 22 is a flowchart of a schematic flow of a first pre-calibration process according to the fourth embodiment of the present invention.
Figure 23:
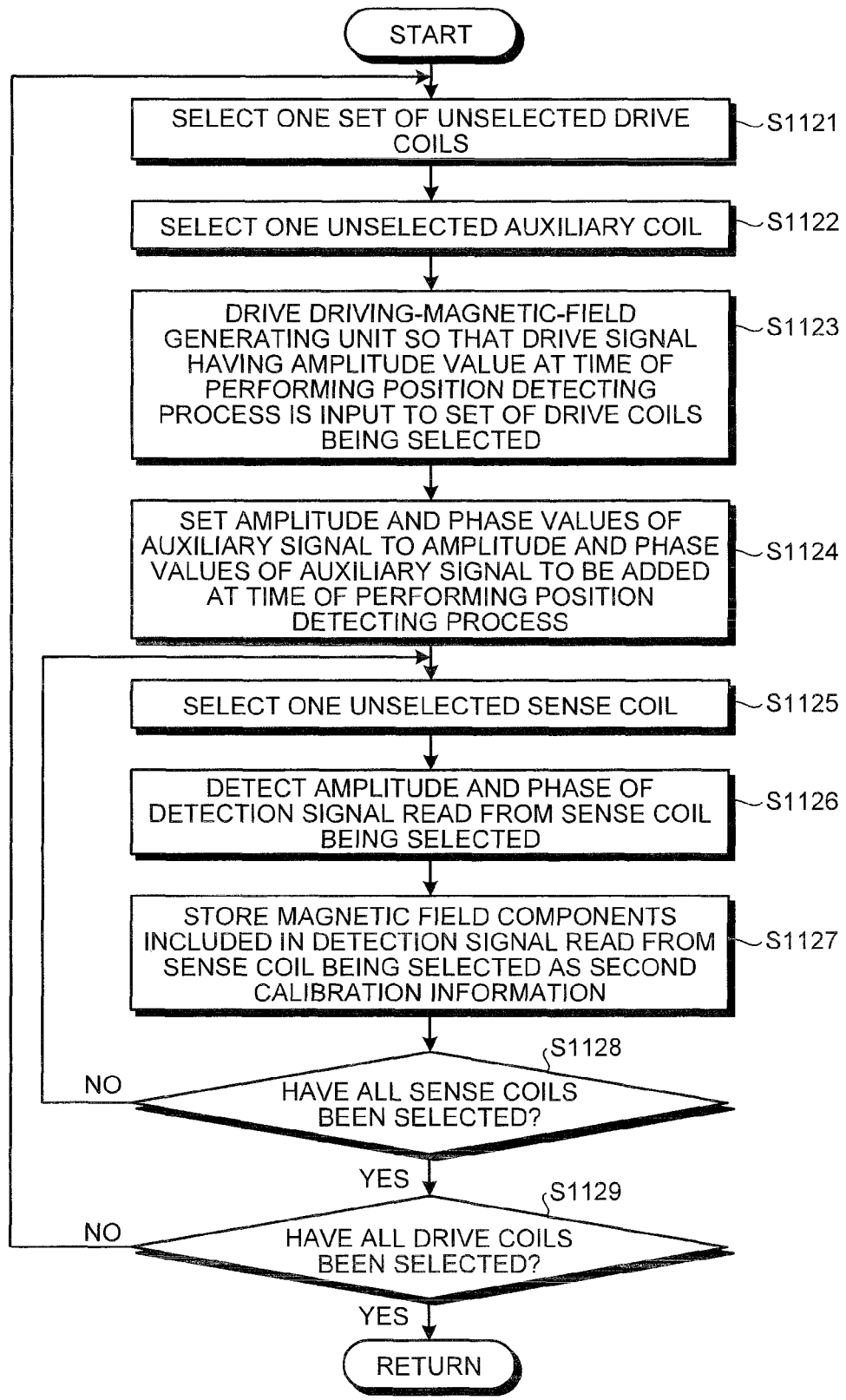
FIG. 23 is a flowchart of a schematic flow of a second pre-calibration process according to the fourth embodiment of the present invention.

A position detection operation according to the present embodiment is explained in detail with reference to the drawings. FIG. 21 is an explanatory diagram of a concept of the position detection operation according to the present embodiment. FIG. 22 is a flowchart of a schematic flow of the first pre-calibration process according to the present embodiment, and FIG. 23 is a flowchart of a schematic flow of the second pre-calibration process according to the present embodiment. In the following explanations, attention is paid to the operation of the control unit 201 that controls the respective units of the external device 400.

Pre-Calibration Process

In the present embodiment, before performing the actual position detecting process of the LC marker 10, as shown in FIG. 21, the first pre-calibration process (Step S1101) and the second pre-calibration process (Step S1102) are performed. The pre-calibration process is performed in the state with the LC marker 10 not being inserted into the detection space K2.

First Pre-Calibration Process

In the first pre-calibration process shown at Step S101 in FIG. 21, as shown in FIG. 22, the control unit 1201 selects one set of unselected drive coils 1224 (Step S1111), and then selects one unselected sense coil 1214 (Step S1112). One set of drives coils 1224*a* and 1224*b* is shown in FIG. 15; however, in the following explanations, it is assumed that a plurality of drive coils (not shown) are disposed near the detection space K2, and these are appropriately driven by using the driving-magnetic-field generating unit 1220.

The control unit 1201 drives the driving-magnetic-field generating unit 1220 to generate a drive signal for generating the driving magnetic field DMF and inputs the drive signal to the drive coils selected at Step S1111 (Step S1113). The control unit 1201 then determines whether the signal intensity (amplitude) of the detection signal Sdet read from the sense coil 1214 being selected by the signal processor 1211 in the position deriving unit 1210 becomes equal to or higher than a first predetermined value, while gradually amplifying the amplitude of the drive signal generated by the signal generating unit 1221 in the driving-magnetic-field generating unit 1220 (Step S1115). The first predetermined value is set according to a dynamic range of the signal processor 1211 that reads the detection signal Sdet, and for example, is a value of 90% of the dynamic range. However, the first predetermined value is not limited to the above value, and the signal intensity of the detection signal Sdet needs only to have the intensity sufficient to derive the phase.

As a result of determination at Step S1115, when the signal intensity of the detection signal Sdet becomes equal to or higher than the first predetermined value (YES at Step S1115), the control unit 1201 derives the phase of the driving magnetic field DMF (see the driving-magnetic-field component line L1 in FIG. 20) from the detection signal Sdet read from the sense coil 1214 being selected (Step S1116), which is stored in, for example, the memory unit 1202 as the first calibration information (Step S1117). Amplification of the amplitude of the drive signal (Step S1114) is continued until the signal intensity of the detection signal Sdet becomes equal to or higher than the first predetermined value (NO at Step S1115). The first calibration information can be information derived by the position calculator 1212 in the position deriving unit 1210 and input to the control unit 1201. Further, association with respective coils means that association is performed by using identification information added to the respective coils and managed in advance.

Thereafter, the control unit 1201 determines whether all the sense coils 1214 have been selected, that is, whether the first calibration information has been stored at Step S1117 for all the sense coils 1214 (Step S1118). When all the sense coils 1214 have not been selected (NO at Step S1118), the control unit 1201 returns to Step S1112 to select an unselected sense coil 1214, and performs the same process thereafter. When all the sense coils 1214 have been selected (YES at Step S1118), the control unit 1201 determines whether all the drive coils 1224 forming a pair have been selected (Step S1119). When all the drive coils 1224 have not been selected (NO at Step S1119), the control unit 1201 returns to Step S1111 to perform the same process thereafter. When all the drive coils 1224 have been selected (YES at Step S1119), the control unit 1201 returns to the first pre-calibration process in FIG. 21.

Second Pre-Calibration Process

In the second pre-calibration process shown at Step S1102 in FIG. 21, as shown in FIG. 23, the control unit 1201 selects one set of unselected drive coils 1224 (Step S1121), and then selects one auxiliary coil 1244 corresponding to the selected set of drive coils 1224 (Step S1122), to drive the driving-magnetic-field generating unit 1220 so that a drive signal having an amplitude value to be added at the time of performing a position detecting process is input to the set of the drive coils 1224 being selected (Step S1123). The control unit 1201 then sets amplitude and phase values of the auxiliary signal generated by the signal generating unit 1241 in the auxiliary-magnetic-field generating unit 1240 to the amplitude and phase values of the auxiliary signal to be added at the time of performing the position detecting process (Step S1124). The control unit 1201 also selects one unselected sense coil 1214 (Step S1125). In FIG. 15, two auxiliary coils 1244*a* and 1244*b* are shown; however, the present invention is not limited thereto, and the auxiliary coil can be appropriately added and disposed according to the arrangement of the drive coils 1224.

The control unit 1201 detects the signal intensity (amplitude) and phase of the detection signal Sdet read from the sense coil 1214 being selected by the signal processor 1211 in the position deriving unit 1210 (Step S1126).

The control unit 1201 then stores the magnetic field components included in the detection signal Sdet (components of the combined magnetic field CMF) read from the sense coil 1214 being selected, for example, in the memory unit 1202 as the second calibration information (Step S1127).

Thereafter, the control unit 1201 determines whether all the sense coils have been selected, that is, whether the amplitude of the auxiliary signal at Step S1127 and the magnetic field components at Step S1127 (the second calibration information) have been stored for all the sense coils 1214 (Step S1128). When all the sense coils have not been selected (NO at Step S1128), the control unit 1201 returns to Step S1125 to perform the same process thereafter. When all the sense coils have been selected (YES at Step S1128), the control unit 1201 determines whether all sets of drive coils 1224 have been selected (Step S1129). When all sets of drive coils 1224 have not been selected (NO at Step S1129), the control unit 1201 returns to Step S1121 to perform the same process thereafter. When all sets of drive coils 1224 have been selected (YES at Step S1129), the control unit 1201 returns to the second calibration process in FIG. 21.

By performing the operation described above, in the present embodiment, the amplitude at the time of driving the respective drive coils 1224 and auxiliary coils 1244 and the first and second pieces of calibration information used for the two-stage calibration process at the time of position detection can be acquired. In the present embodiment, the sense coils 1214 are selected and determined sequentially; however, the present invention is not limited thereto, and for example, all the sense coils 1214 can be selected and determined simultaneously.

Position Detecting Process

Figure 24:
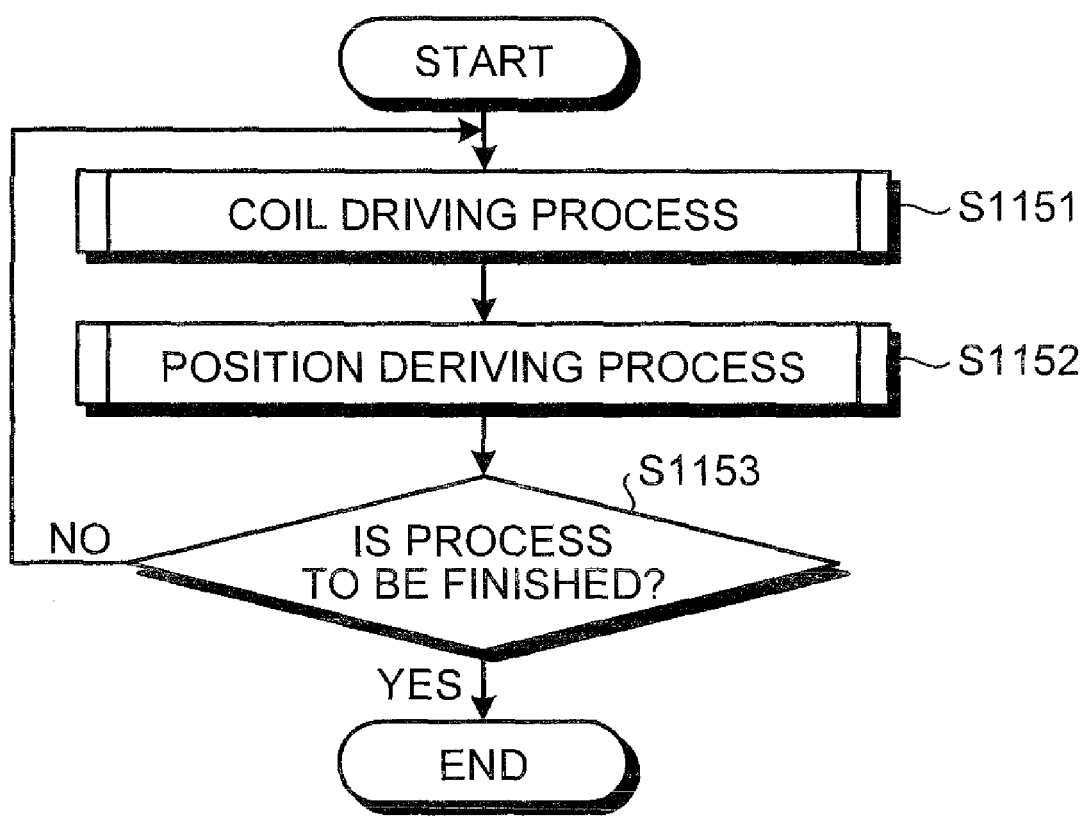
FIG. 24 is a flowchart of an overall schematic flow of a position detecting process according to the fourth or fifth embodiment of the present invention.
Figure 25:
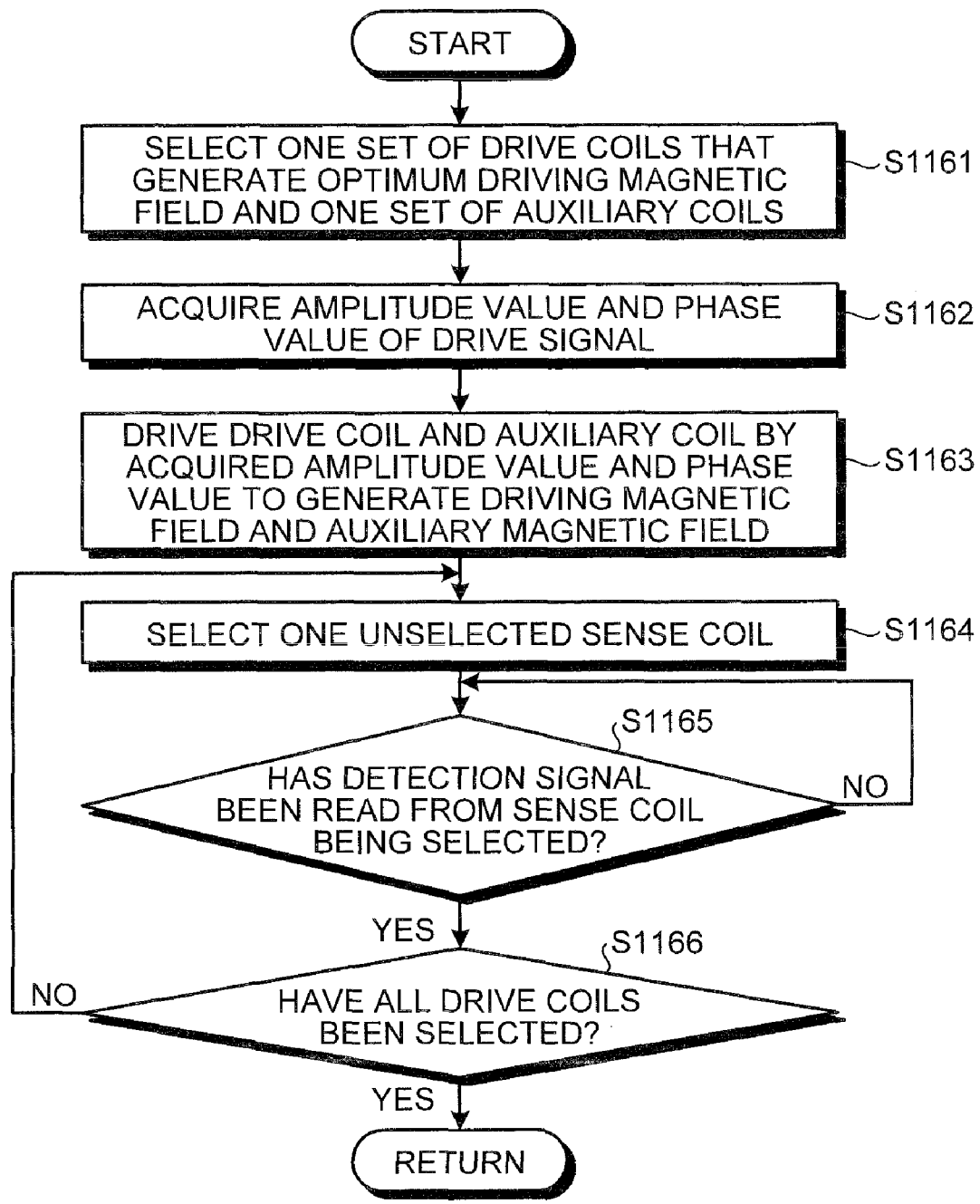
FIG. 25 is a flowchart of a schematic flow of a coil driving process according to the fourth or fifth embodiment of the present invention.
Figure 26:
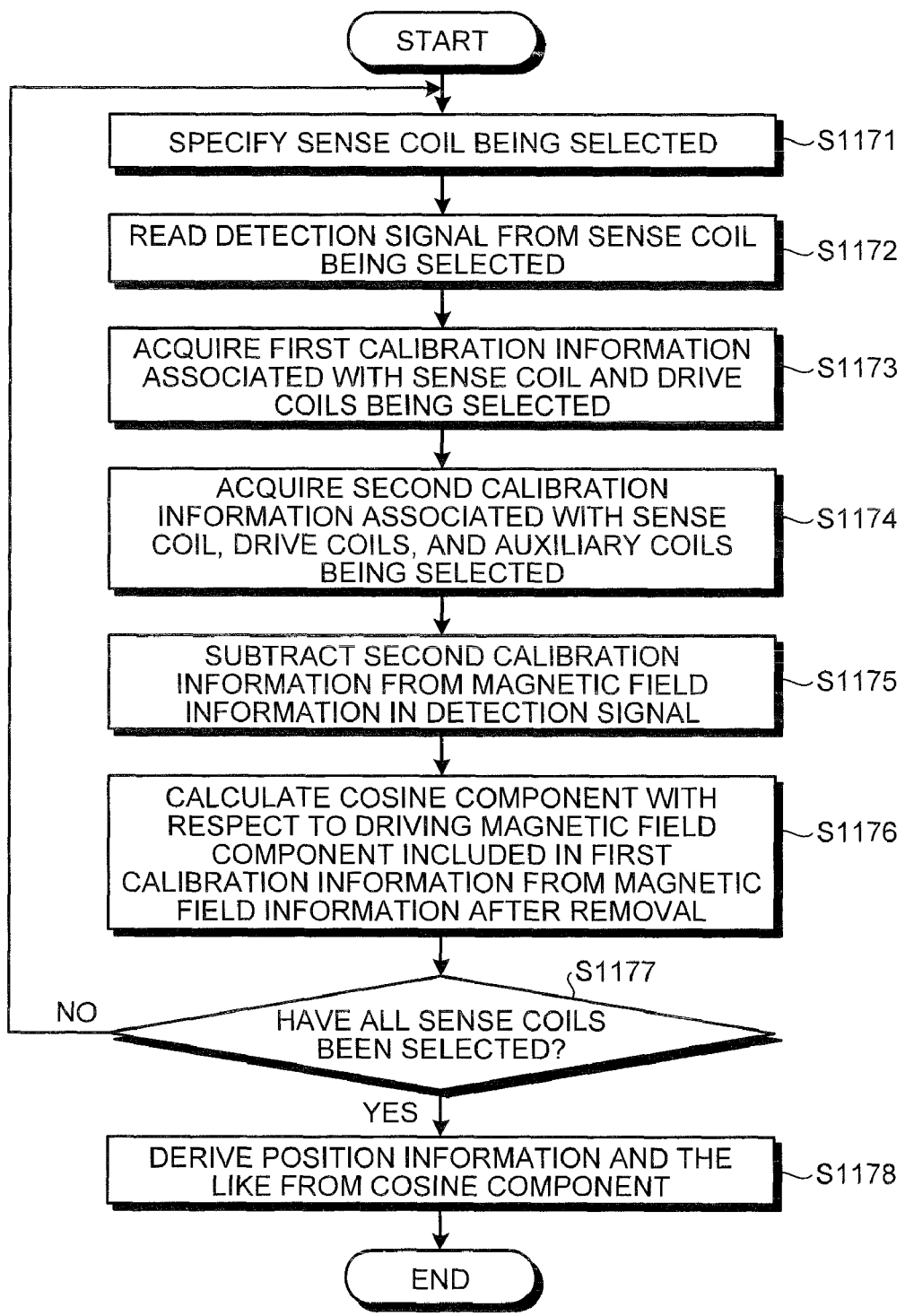
FIG. 26 is a flowchart of a schematic flow of a position deriving process according to the fourth or fifth embodiment of the present invention.

Subsequently, the position detecting process according to the present embodiment is explained in detail with reference to the drawings. FIG. 24 is a flowchart of an overall schematic flow of a position detecting process according to the present embodiment. FIG. 25 is a flowchart of a schematic flow of a coil driving process according to the present embodiment, and FIG. 26 is a flowchart of a schematic flow of the position deriving process according to the present embodiment. Because the operation is performed at the time of actual position detection of the LC marker 10, the LC marker 10 inserted into the subject 900 is disposed together with the subject 900 in the detection space K2.

As shown in FIG. 24, in the position detecting process, the control unit 1201 drives the driving-magnetic-field generating unit 1220 and the auxiliary-magnetic-field generating unit 1240 to perform the coil driving process for forming the driving magnetic field DMF and the auxiliary magnetic field SMF in the detection space K2 (Step S1151), and in this state, performs the position deriving process for deriving the position and the like of the LC marker 10 based on the detection signal Sdet read from the respective sense coils 1214 by the signal processor 1211 (Step S1152). The control unit 1201 then determines whether a termination instruction has been input, for example, from the operation input unit 1203 (see FIG. 15) (Step S1153). When the termination instruction has not been input (NO at Step S1153), the control unit 1201 returns to Step S1151 to repeat the operation thereafter. When the termination instruction has been input (YES at Step S1153), the control unit 1201 finishes the process. The position deriving process can be performed by the position calculator 1212. That is, in the present embodiment, at least one of the control unit 1201 and the position calculator 1212 functions as a position detector that derives the position information and the like of the LC marker 10, by using the magnetic field information derived by the signal processor 1211, the phase of the driving magnetic field DMF stored in the memory unit 1202 or the like (phase storage unit), and the information of the combined magnetic field CMF stored in the memory unit 1202 or the like (combined-magnetic-field information storage unit).

Coil Driving Process

In the coil driving process (Step S1151) in FIG. 24, as shown in FIG. 25, the control unit 1201 selects one set of drive coils 1224 that generate an optimum driving magnetic field DMF and one set of auxiliary coils 1244 associated in advance with the respective sets of drive coils 1224 for generating an optimum auxiliary magnetic field, based on the current position and orientation of the LC marker 10 (Step S1161).

The control unit 1201 then acquires an amplitude value and a phase value of the drive signal to be input to the drive coils 1224, and an amplitude value and a phase value of the drive coil 1224 to be input to the auxiliary coils 1244 (Step S1162), and drives the driving-magnetic-field generating unit 1220 and the auxiliary-magnetic-field generating unit 1240 so that the signal generating units 1221 and 1241 generate the drive signal and the auxiliary signal having the amplitude value and phase value, respectively, thereby forming the driving magnetic field DMF and the auxiliary magnetic field SMF in the detection space K2 (Step S1163). It is assumed that the amplitude values and phase values of the drive signal and auxiliary signal are set in advance.

The control unit 1201 then selects one unselected sense coil 1214 (Step S1164), monitors whether the detection signal Sdet has been read from the sense coil 1214 being selected (Step S1165), and waits until readout is complete (NO at Step S1165). This operation can be realized by a configuration in which, for example, the signal processor 1211 or the position calculator 1212 in the position deriving unit 1210 inputs a signal informing completion of readout of the detection signal Sdet to the control unit 1201, or determination based on an input of the position information or the like from the position deriving unit 1210.

As a result of determination at Step S1165, when readout of the detection signal Sdet is complete (YES at Step S1165), the control unit 1201 determines whether all the sense coils 1214 have been selected, that is, whether the detection signal Sdet has been read from all the sense coils 1214 (Step S1166). When the detection signal Sdet has not been read from all the sense coils 1214 (NO at Step S1166), the control unit 1201 returns to Step S1164, to perform the same process thereafter. When the detection signal Sdet has been read from all the sense coils 1214 (YES at Step S1166), the control unit 1201 returns to the position detecting process shown in FIG. 24.

Position Deriving Process

In the position deriving process (Step S1152) in FIG. 24, as shown in FIG. 26, the control unit 1201 specifies the sense coil 1214 selected at Step S1162 in FIG. 25 (Step S1171), so that the signal processor 1211 in the position deriving unit 1210 performs readout of the detection signal Sdet from the sense coil 1214 (Step S1172).

The control unit 1201 then acquires the first calibration information associated with the sense coil 1214 and drive coils 1224 being selected, and the second calibration information associated with the sense coil 1214, drive coils 1224, and auxiliary coils 1244 being selected from the memory unit 1202 or the like (Steps S1173 and S1174). The first calibration information is, for example, the one stored at Step S1117 in FIG. 22, and the second calibration information is, for example, the one stored at Step S1127 in FIG. 23.

Subsequently, the control unit 1201 removes the second calibration information, that is, the components of the combined magnetic field CMF by subtracting the components from the magnetic field information included in the detection signal Sdet by vector operation according to the position deriving procedure explained with reference to FIG. 20 (Step S1175), and calculates the cosine component of the complex vector component of the resonant magnetic field RMF acquired thereby with respect to the driving-magnetic-field component line L1 (the phase of the driving magnetic field DMF) (Step S1176). The calculated cosine component is stored in, for example, the memory unit 1202 or the like in association with the sense coil 1214 being selected.

The control unit 1201 determines whether all the sense coils 1214 have been selected, that is, whether the cosine component of the resonant magnetic field RMF has been calculated by using the detection signal Sdet read from all the sense coils 1214 (Step S1177). When all the sense coils 1214 have been selected (YES at Step S1177), position information and the like such as the current position and orientation of the LC marker 10 are calculated by using the cosine component of the resonant magnetic field RMF calculated for each detection signal Sdet from the sense coil 1214 (Step S1178). When all the sense coils 1214 have not been selected (NO at Step S1177), the control unit 1201 returns to Step S1171 to perform the same process thereafter. The derived position information and the like are stored, for example, in the memory unit 1202 or the like.

With the above operations, in the present embodiment, the phase of the driving magnetic field DMF formed in the detection space K2 in the state with the LC resonant circuit 111 not being inserted, and the information of the combined magnetic field CMF formed in the detection space K2 at the time of generating the driving magnetic field DMF and the auxiliary magnetic field SMF in the state with the LC resonant circuit 111 not being inserted are stored in the memory unit 1202 or the like in advance. Information of the resonant magnetic field RMF (cosine component) is extracted from the magnetic field information acquired by the signal processor 1211 at the time of position detection, by using the phase of the driving magnetic field DMF and the information of the combined magnetic field CMF stored in the memory unit 1202 or the like, and the position information and the like of the LC marker 10 is derived by using the extracted information of the resonant magnetic field RMF (cosine component). Therefore, the information of the resonant magnetic field RMF can be accurately extracted at the time of position detection, thereby enabling to realize the position detecting system 4 and the position detecting method using the auxiliary coil capable of stably deriving an accurate position.

Fifth Embodiment

Configurations and operations of a position detecting system 5 according to a fifth embodiment of the present invention are explained in detail with reference to the drawings. The position detecting system 5 according to the present embodiment further includes a configuration in which the position detecting system 4 according to the fourth embodiment described above derives the position and orientation of the LC marker 20 by using an external magnetic field (hereinafter, "guidance magnetic field"). In the following explanations, constituent elements identical to those of the fourth embodiment of the present invention are denoted by like reference characters and explanations thereof will be omitted.

Configuration of Position Detection Magnetic Guidance

Figure 27:
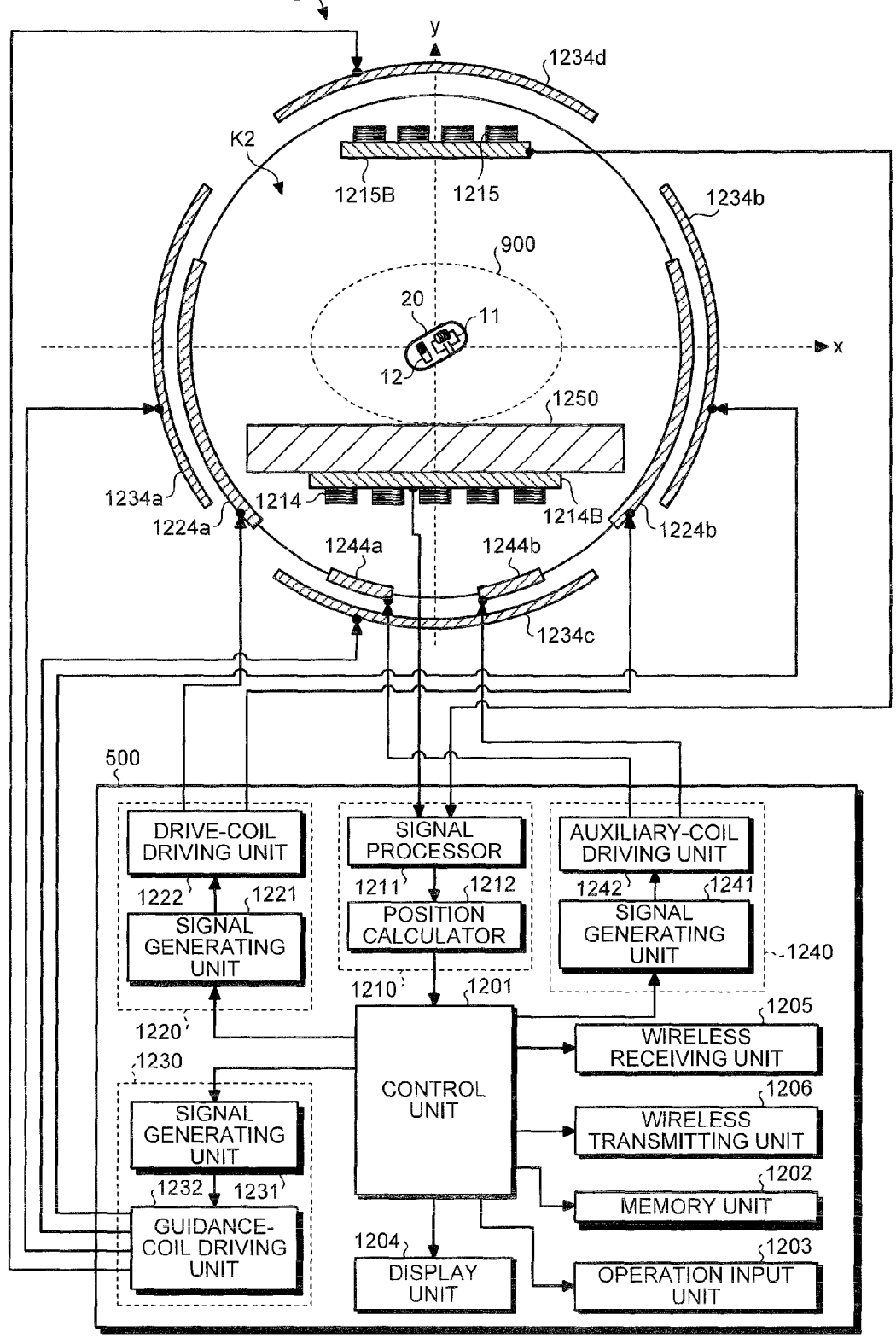
FIG. 27 is a schematic diagram of a schematic configuration of a position detecting system according to the fifth embodiment of the present invention.

FIG. 27 is a schematic diagram of a schematic configuration of the position detecting system 5 according to the present embodiment. As shown in FIG. 27, the position detecting system 5 includes the detection space K2 and an external device 500 that detects the position and orientation (posture) of the LC marker 20 in the detection space K2 and generates the guidance magnetic field to guide the position and orientation of the LC marker 20.

LC Marker

As shown in FIG. 14, the LC marker 20 according to the present embodiment further includes the permanent magnet M12 in the configuration same as that of the LC marker 10 (see FIG. 2) in the first, second, and fourth embodiments described above. The permanent magnet M12 is fixed to the casing 18 of the LC marker 20, and generates a propulsive force and a rotative force in the LC marker 20 for changing the position and orientation of the LC marker 20 due to an action of the guidance magnetic field described later. In the present invention, the one that generates the propulsive force and rotative force is not limited to the permanent magnet M12, and it can be changed variously so long as it can generate a magnetic field in which the guidance magnetic field GMF described later operates. Other configurations of the LC marker 20 are identical to those of the LC marker 10 according to the first, third, and fourth embodiments described above.

Detection Space

Guidance coils 1234*a* to 1234*d* (hereinafter, 1234 is denoted as the reference numeral of an arbitrary guidance coil) are disposed to surround the detection space K2, other than the drive coils 1224 and the auxiliary coils 1244.

Two guidance coils 1234*a* and 1234*b* opposite to each other putting the detection space K2 therebetween in the x-axis direction form a pair, and for example, generates a substantially uniform guidance magnetic field GMFx including magnetic field lines extending in the x-axis direction in the detection space K2. Two guidance coils 1234*c* and 1234*d* opposite to each other putting the detection space K2 therebetween in the y-axis direction form a pair, and for example, generates a substantially uniform guidance magnetic field GMFy including magnetic field lines extending in the y-axis direction in the detection space K2. Drive coils that generate a substantially uniform guidance magnetic field including magnetic field lines extending in a direction different from the x-axis and y-axis can be provided separately in the detection space K2. The guidance coil 1234 can be constituted so that a gradient magnetic field is generated in the detection space K2. In the following explanations, GMF is denoted as the reference character of the guidance magnetic field in an arbitrary direction. Other configurations are identical to those of the coil configuration disposed in the detection space K2 in the fourth embodiment described above.

External Device

An external device 500 according to the present embodiment further includes a guidance-magnetic-field generating unit 1230 that drives the guidance coil 1234 in the same configuration of the external device 400 according to the fourth embodiment described above.

The control unit 1201 displays information such as the current position and orientation of the LC marker 20 by using the position information and the like input from the position calculator 1212. An operator can input an operation instruction for operating the position and orientation of the LC marker 20 by using the operation input unit 1203, while confirming the current position and orientation of the LC marker 20 based on the information displayed on the display unit 1204. Further, the operator can also input an acquisition instruction of the in-vivo information to the LC marker 20 by using the operation input unit 1203.

The control unit 1201 calculates information including the guidance magnetic field (hereinafter, "guidance information") to be applied to the permanent magnet M12 mounted on the LC marker 20 based on the current position and orientation of the LC marker 20 and the target position and orientation input from the operation input unit 1203 and inputs the information to the guidance-magnetic-field generating unit 1230.

The guidance-magnetic-field generating unit 1230 includes a signal generating unit 1231 and a guidance-coil driving unit 1232. The guidance information calculated by the control unit 1201 is input to the signal generating unit 1231 in the guidance-magnetic-field generating unit 1230. The signal generating unit 1231 calculates a signal waveform having a frequency different from the resonant frequency F0 according to the guidance information input from the control unit 1201, and generates a signal having the signal waveform (hereinafter, "guidance signal") to output the signal to the guidance-coil driving unit 1232.

The guidance signal output from the signal generating unit 1231 is input to the guidance-coil driving unit 1232. The guidance-coil driving unit 1232 amplifies the current of the input guidance signal, and appropriately input the amplified guidance signal to the guidance coil 1234. The guidance coil 1234, to which the amplified guidance signal has been input, emits a magnetic field of the frequency different from the resonant frequency F0 held by the LC resonant circuit 111 in the LC marker 20, thereby forming the guidance magnetic field GMF in the detection space K2, which acts on the permanent magnet M12 in the LC marker 20.

Position Deriving Procedure

Figure 28:
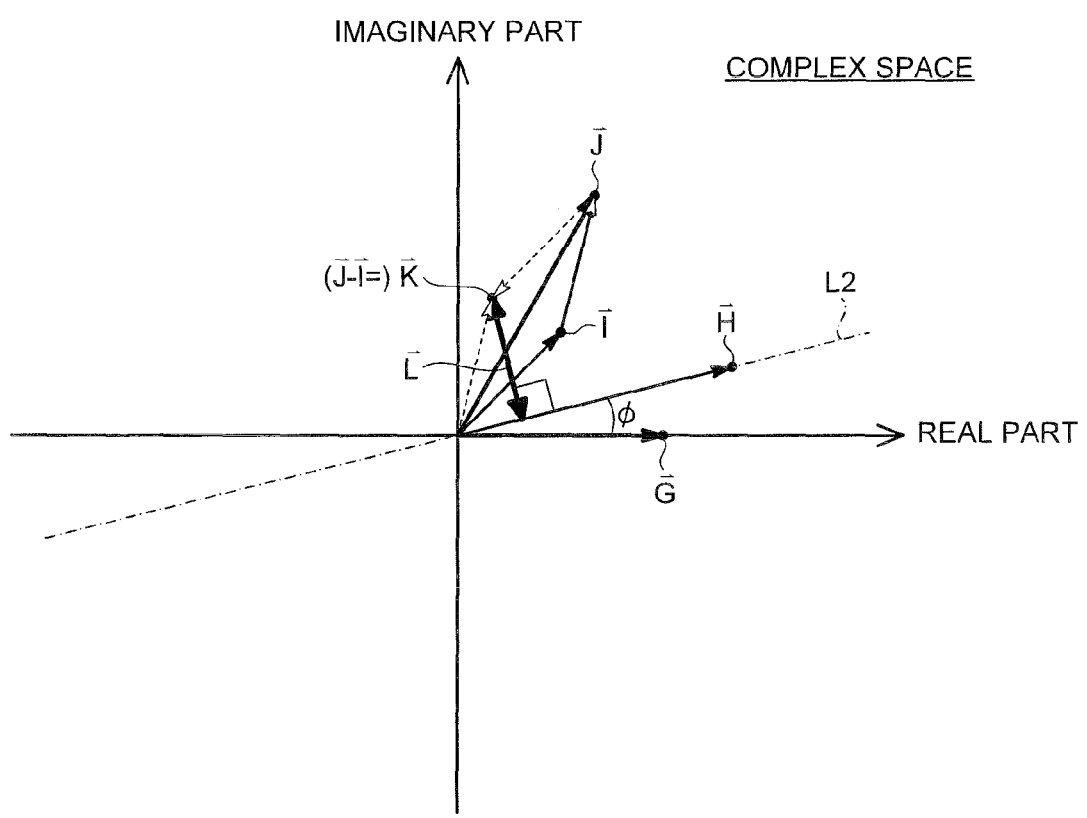
FIG. 28 is an explanatory diagram of contents of a position deriving procedure according to the fifth embodiment of the present invention.

A position deriving procedure according to the present embodiment is explained in detail with reference to the drawings. FIG. 28 is an explanatory diagram of contents of the position deriving procedure according to the present embodiment.

In the present embodiment, the guidance coils 1234 are disposed near the detection space K2 in addition to the drive coils 1224 and the auxiliary coils 1244. Therefore, the guidance coils 1234 are mutually induced by the driving magnetic field DMF emitted from the drive coils 1224 and the auxiliary magnetic field SMF emitted from the auxiliary coils 1244, thereby forming an unnecessary magnetic field (hereinafter, "unnecessary magnetic field of the guidance coil") having the resonant frequency F0 emitted from the guidance coil 1234 in the detection space K2.

Therefore, in the present embodiment, as shown in FIG. 28, the intensity and phase of the combined magnetic field CMF formed in the detection space K2 is actually measured when the driving magnetic field DMF and the auxiliary magnetic field SMF are generated in the state with the LC marker 20 (particularly, the LC resonant circuit 111) not being inserted, to cancel an influence of the unnecessary magnetic field including the unnecessary magnetic field of the guidance coil (the driving magnetic field DMF and the auxiliary magnetic field SMF), and these are stored in the memory unit 1202 or the like (phase storage unit), for example, as the third calibration information. The intensity and phase of the drive signal to be input to the drive coils 1224 from the driving-magnetic-field generating unit 1220 are indicated by, for example, a complex vector 'G' shown in FIG. 28, whereas the intensity and phase of the combined magnetic field CMF included in the detection signal Sdet read from the signal processor 1211 are indicated by, for example, a complex vector 'H' shown in FIG. 28. In FIG. 28, a driving-magnetic-field component line L2 indicating an inclination φ of the complex vector 'H' with respect to the complex vector 'G' indicates a phase difference of the combined magnetic field CMF with respect to the drive signal formed in the detection space K2, that is, the phase of the combined magnetic field CMF based on the phase of the drive signal.

In the present embodiment, as in the fourth embodiment described above, the intensity and phase of the combined magnetic field CMF formed at the positions of the respective sense coils 1214 when the driving magnetic field DMF and the auxiliary magnetic field are generated in the state with the LC marker 20 (particularly, the LC resonant circuit 111) not being inserted are acquired, according to the pre-calibration process, which is stored in the memory unit 1202 or the like (combined-magnetic-field information storage unit), for example, as the fourth calibration information. The intensity and phase of the combined magnetic field CMF are indicated by, for example, a complex vector 'I' shown in FIG. 28. However, the unnecessary magnetic field of the guidance coil is included in the combined magnetic field CMF in addition to the driving magnetic field DMF and the auxiliary magnetic field SMF.

In the two-stage calibration process in the actual position deriving process, if the magnetic field information included in the detection signal Sdet read from a certain sense coil 1214 is assumed as a complex vector 'J' in FIG. 28, the fourth calibration information (the complex vector 'I') is subtracted from the complex vector 'J' according to the vector operation. Accordingly, the component of the combined magnetic field CMF (the complex vector 'I') is removed from the magnetic field information included in the detection signal Sdet (complex vector 'K'=complex vector 'J'−complex vector 'I'). Subsequently, the complex vector 'K' acquired by the vector operation is projected to the driving-magnetic-field component line L2 indicating the phase of the driving magnetic field DMF, thereby deriving a cosine component of the complex vector 'K' with respect to the driving-magnetic-field component line L2. Accordingly, components of the resonant magnetic field RMF (a complex vector 'L') can be extracted from the detection signal Sdet.

By performing the process descried above, because the components of the unnecessary magnetic field included in the actually generated magnetic field can be eliminated, the components of the resonant magnetic field RMF (the complex vector 'L') can be extracted more accurately, and as a result, more accurate information such as the position and orientation of the LC marker 20 can be derived.

Figure 29:
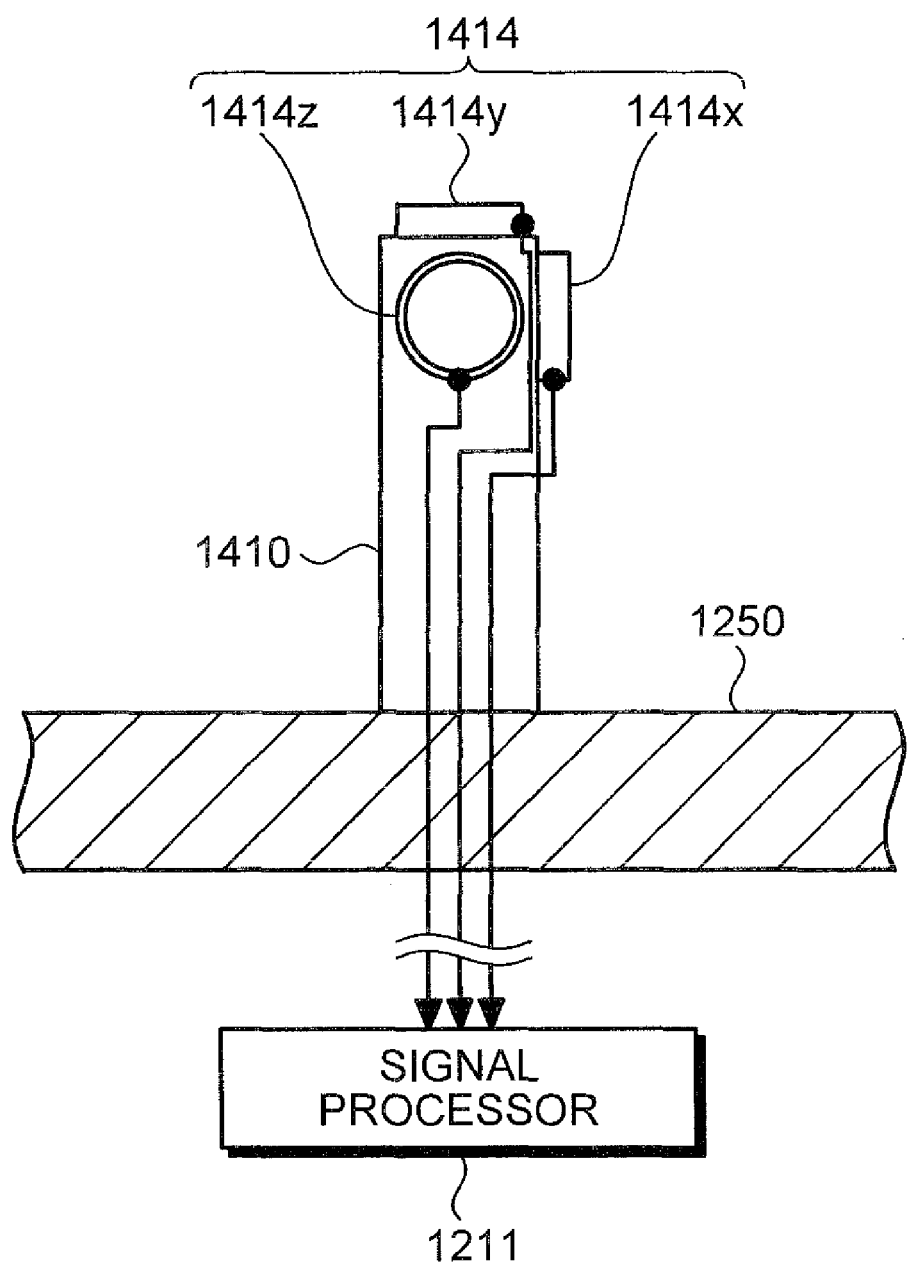
FIG. 29 is an example of a magnetic sensor according to the fifth embodiment of the present invention.

In the present embodiment, a case that a magnetic field sensor 1414 as shown in FIG. 29 is used for detecting the driving magnetic field DMF formed in the detection space K2 is exemplified. As shown in FIG. 29, the magnetic field sensor 1414 is a 3-axis magnetic field sensor including a sense coil 1414x that detects a component of the magnetic field formed in the detection space K2 in the x-axis direction, a sense coil 1414y that detects a component of the same magnetic field in the y-axis direction, and a sense coil 1414z that detects a component of the same magnetic field in a z-axis direction, and is driven synchronously with the drive coils 1224, the auxiliary coils 1244, and the sense coils 1214 to detect the phase of the magnetic field formed in the detection space K2. For example, the detection signals detected by the respective sense coils 1414x, 1414y, and 1414z of the 3-axis magnetic field sensor 1414 can be processed by the same detection circuit as in the signal processor 1211 in the position deriving unit 1210 described above.

For example, the magnetic field sensor 1414 is disposed on an upper end side of a stand 1410 mounted on the table 1250. A positioning marker for the stand 1410 can be provided on an upper surface of the table 1250. Accordingly, such a problem that the third calibration information different for each pre-calibration process is acquired can be avoided.

Further, it is desired that the height of the magnetic field sensor 1414 from the upper surface of the table 1250 due to the stand 1410 is matched substantially with the center of a height range where the LC marker 20 inserted into the subject 900 is present. Accordingly, the information of the driving magnetic field DMF substantially equal to the magnetic field actually applied to the LC resonant circuit 111 in the LC marker 20 can be acquired as the third calibration information.

Further, in the present embodiment, a plurality of the magnetic field sensors 1414 can be disposed on the table 1250, to acquire the third calibration information at the respective positions. Accordingly, the most appropriate third calibration information can be selected according to the position of the LC marker 20 at the time of position detection, and as a result, more accurate information of the position and orientation of the LC marker 20 can be derived.

The reason why the 3-axis magnetic field sensor is used as the magnetic field sensor 1414 in the above explanation is that the present embodiment assumes that the driving magnetic field DMF in the x-axis direction, the driving magnetic field DMF in the y-axis direction, and the driving magnetic field in the z-axis direction are appropriately switched and generated according to the position and orientation of the LC marker 20.

Position Detection Operation

Figure 30:
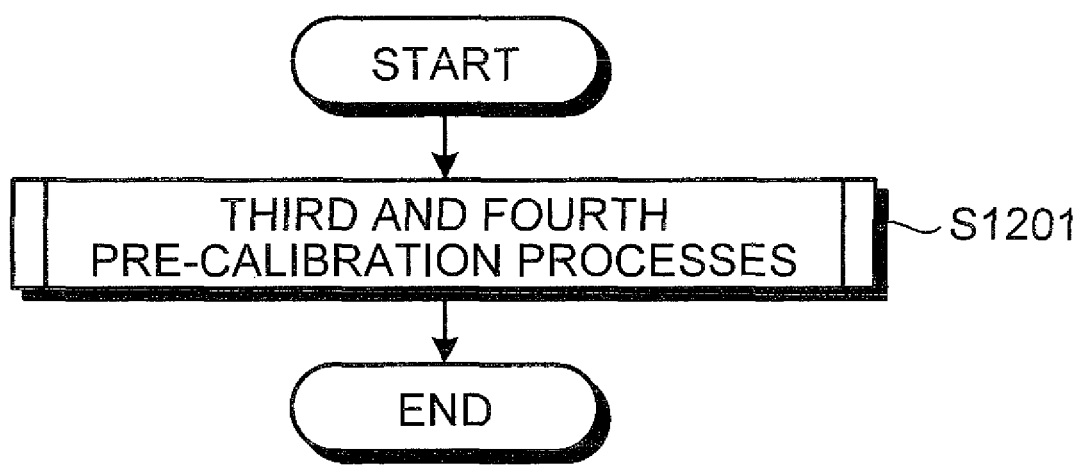
FIG. 30 is an explanatory diagram of a concept of a position detection operation according to the fifth embodiment of the present invention.
Figure 31:
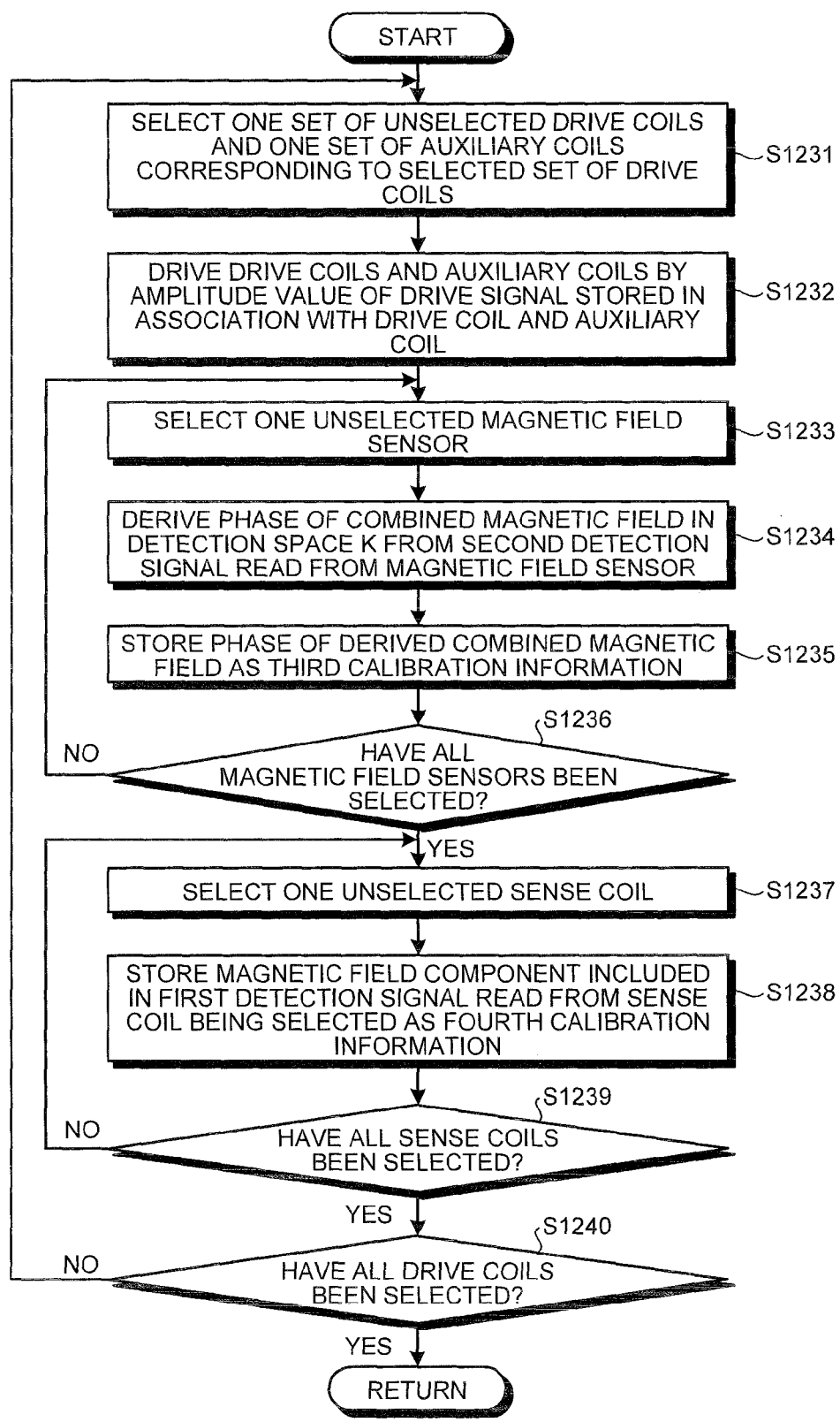
FIG. 31 is a flowchart of a schematic flow of third and fourth pre-calibration processes according to the fifth embodiment of the present invention.

The position detection operation according to the present embodiment is explained in detail with reference to the drawings. FIG. 30 is an explanatory diagram of a concept of the position detection operation according to the present embodiment. FIG. 31 is a flowchart of a schematic flow of third and fourth pre-calibration processes according to the present embodiment. In the following explanations, attention is paid to the operation of the control unit 1201 that controls the respective units of the external device 500.

Pre-Calibration Process

In the present embodiment, before performing the actual position detecting process of the LC marker 20, as shown in FIG. 30, the third and fourth pre-calibration processes described later are performed as the pre-calibration process (Step S1201). The pre-calibration process is performed in the state with the LC marker 20 not being inserted into the detection space K2 in FIG. 27.

Third and Fourth Pre-Calibration Processes

In the third and fourth pre-calibration processes shown at Step S1201 in FIG. 30, as shown in FIG. 31, the control unit 1201 selects one set of unselected drive coils 1224 and auxiliary coils 1244 corresponding to the drive coils 1224 (Step S1231), and reads an amplitude value of the drive signal and the auxiliary signal stored in association with the drive coils 1224 and the auxiliary coils 1244 being selected, for example, from the memory unit 1202 or the like, to drive the driving-magnetic-field generating unit 1220 so that the drive signal and the auxiliary signal having the amplitude value are respectively input to the drive coils 1224 and the auxiliary coils 1244 selected at Step S1231 (Step S1232).

The control unit 1201 then selects one unselected magnetic field sensor 1414 (Step S1233). The third pre-calibration process is performed in a state with a plurality of the magnetic field sensors 1414 being disposed at predetermined positions on the table 1250.

The control unit 1201 reads a detection signal (hereinafter, "second detection signal" for convenience of explanations) from the magnetic field sensor 1414 being selected by using the signal processor 1211, to derive the phase of the combined magnetic field CMF (see driving-magnetic-field component line L2 in FIG. 28) included in the second detection signal (Step S1234), and stores the phase, for example, in the memory unit 1202 or the like as the third calibration information (Step S1235). The third calibration information can be information derived by the position calculator 1212 in the position deriving unit 1210 and input to the control unit 1201.

Thereafter, the control unit 1201 determines whether all the magnetic field sensors 1414 have been selected, that is, whether the third calibration information at Step S1235 has been stored for all the magnetic field sensors 1414 (Step S1236). When all the magnetic field sensors 1414 have not been selected (NO at Step S1236), the control unit 1201 returns to Step S1233 to select an unselected magnetic field sensor 1414 and performs the same process thereafter. When all the magnetic field sensors 1414 have been selected (YES at Step S1236), the control unit 1201 selects one of the unselected sense coils 1214 (Step S1237). The fourth pre-calibration process is performed in a state with the magnetic field sensors 1414 disposed on the table 1250 being removed in the third pre-calibration process.

The control unit 1201 reads the first detection signal Sdet from the sense coil 1214 being selected by using the signal processor 1211, and stores the magnetic field component (component of the combined magnetic field CMF) included in the first detection signal Sdet, for example, in the memory unit 1202 or the like as the fourth calibration information (Step S1238).

The control unit 1201 then determines whether all the sense coils 1214 have been selected (Step S1239). When all the sense coils 1214 have not been selected (NO at Step S1239), the control unit 1201 returns to Step S1237 to select an unselected sense coil 1214 and performs the same process thereafter. When all the sense coils 1214 have been selected (YES at Step S1239), the control unit 1201 determines whether all the drive coils 1224 forming a pair have been selected (Step S1240). When all the drive coils 1224 have not been selected (NO at Step S1240), the control unit 1201 returns to Step S1231, to perform the same process thereafter. When all the drive coils 1224 have been selected (YES at Step S1240), the control unit 1201 returns to the third and fourth pre-calibration processes in FIG. 30.

By performing the operation described above, in the present embodiment, the amplitude at the time of driving the respective drive coils 1224 and auxiliary coils 1244 and the third and fourth pieces of calibration information used for the two-stage calibration process at the time of position detection can be acquired.

Position Detecting Process

In the position detecting process according to the present embodiment, an overall schematic flow of the position detecting process and a schematic flow of the coil driving process for forming the driving magnetic field DMF and the auxiliary magnetic field SMF in the detection space K2 by driving the driving-magnetic-field generating unit 1220 and the auxiliary-magnetic-field generating unit 1240 are identical to the flow in the fourth embodiment explained with reference to FIGS. 24 and 25. The position deriving process (corresponding to Step S1152 in FIG. 24) is the same as the flow explained with reference to FIG. 26 except that the first calibration information and the second calibration information are respectively replaced by the third calibration information and the fourth calibration information, and the cosine component of the resonant magnetic field RMF is calculated by using the principle shown in FIG. 28.

By performing the operation described above, in the present embodiment, the phase of the driving magnetic field DMF formed in the detection space K2 in the state with the LC resonant circuit 111 not being inserted, and the information of the combined magnetic field CMF formed in the detection space K2 at the time of generating the driving magnetic field DMF and the auxiliary magnetic field SMF in the state with the LC resonant circuit 111 not being inserted are stored in the memory unit 1202 or the like in advance. The information of the resonant magnetic field RMF (cosine component) is extracted from the information of the magnetic field acquired by the signal processor 1211 at the time of position detection by using the phase of the driving magnetic field DMF and the information of the combined magnetic field CMF stored in the memory unit 1202 or the like, to derive the position information and the like of the LC marker 20 by using the extracted information (cosine component) of the resonant magnetic field RMF. Therefore, the information of the resonant magnetic field RMF can be derived accurately at the time of position detection, thereby enabling to realize the position detecting system 5 and the position detection method using the auxiliary coil 1244 capable of stably deriving an accurate position.

The above embodiments are only examples for carrying out the present invention. The present invention is not limited to these embodiments and various changes according to specifications or the like are within the scope of the invention.

In addition, it is obvious from the above description that various other embodiments can be made within the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting system comprising:
a detected object disposed in a detection space; and
an external device disposed outside the detection space, wherein
the detected object includes a resonant circuit that generates a resonant magnetic field according to a driving magnetic field formed in the detection space, and
the external device includes
at least two drive coils that form the driving magnetic field in the detection space;
at least two drive-signal input units that input a drive signal for forming the driving magnetic field to the drive coils, respectively;
at least one sense coil that detects a magnetic field formed in the detection space;
a signal adjustment unit that adjusts a phase or an amplitude of the drive signal input to each of the drive coils by the drive-signal input units, by using an evaluation function for evaluating the phase or the amplitude of the drive signal, based on an intensity of the magnetic field detected by the sense coil; and
a position deriving unit that derives a position of the detected object based on a magnetic field detected by the sense coil, wherein
the evaluation function derives a solution by adding or multiplying a weight set according to a positional relation between each drive coil and each sense coil to or by an intensity of a magnetic field detected by the sense coils.

2. The position detecting system according to claim 1, wherein the signal adjustment unit changes the weight based on at least one of an amplitude or a phase of the drive signal and an intensity of a magnetic field detected by the sense coils.

3. The position detecting system according to claim 1, wherein
the external device includes
an auxiliary coil that generates an auxiliary magnetic field that negates a driving magnetic field input to at least one of the sense coils; and
an auxiliary-signal input unit that inputs an auxiliary signal for causing the auxiliary coil to generate the auxiliary magnetic field, and
the signal adjustment unit adjusts at least one of a phase or an amplitude of the drive signal input to at least one of the drive coils by the drive-signal input unit and a phase and an amplitude of the auxiliary signal input to the auxiliary coil by the auxiliary-signal input unit, based on a magnetic field detected by the sense coil.

4. The position detecting system according to claim 3, wherein
the signal adjustment unit adjusts at least one of a phase and an amplitude of at least one of the drive signal and the auxiliary signal, by using an evaluation function for evaluating the at least one of the phase and the amplitude of the at least one of the drive signal and the auxiliary signal based on an intensity of a magnetic field detected by the sense coils, and
the evaluation function derives a solution by adding or multiplying a weight set according to a positional relation between the respective drive coils and the auxiliary coil, and each sense coil to or by an intensity of a magnetic field detected by the sense coil.

5. The position detecting system according to claim 3, wherein
the signal adjustment unit adjusts the at least one of the phase and the amplitude of the at least one of the drive signal and the auxiliary signal, by using an evaluation function for evaluating the at least one of the phase and the amplitude of the at least one of the drive signal and the auxiliary signal based on an intensity of a magnetic field detected by the sense coil, and
the evaluation function derives a solution by adding or multiplying a weight set according to at least one of a positional relation between the respective drive coils and the auxiliary coil, and each sense coil, and a shape of each drive coil.

6. The position detecting system according to claim 4, wherein the signal adjustment unit changes the weight based on at least one of an amplitude or a phase of the drive signal and an intensity of a magnetic field detected by the sense coils.

7. A position detecting method for detecting a position of a detected object that is inserted into a detection space where at least two drive coils that form a driving magnetic field are disposed to generate a resonant magnetic field for detecting a position of the detected object according to the driving magnetic field, the position detecting method comprising:
detecting a magnetic field formed in the detection space by at least one sense coil provided outside the detected object, by inputting a drive signal to the drive coils in a state with the detected object not being inserted into the detection space;
adjusting a phase or an amplitude of the drive signal by using an evaluation function for evaluating the phase or the amplitude of the drive signal based on an intensity of the detected magnetic field;
forming a driving magnetic field in the detection space by inputting the drive signal, with a phase or an amplitude thereof being adjusted, to the drive coils in a state with the detected object being inserted into the detection space;
detecting a magnetic field in the detection space at a time of forming the driving magnetic field in the detection space by the at least one sense coil; and
deriving a position of the detected object based on the magnetic field detected at a time of forming the driving magnetic field in the detection space, wherein
the evaluation function derives a solution by adding or multiplying a weight set according to a positional relation between each drive coil and each sense coil to or by an intensity of a magnetic field detected by the sense coil.

8. The position detecting method according to claim 7, wherein the adjusting includes fixing a phase or an amplitude of at least one drive signal of the drive signals input to each of the at least two drive coils, and adjusting at least one of a phase and an amplitude of the other drive signal with respect to a drive signal with the phase or the amplitude being fixed.

9. A position detecting system comprising:
a body-insertable apparatus disposed in a detection space in a state of being inserted into a subject; and an external device disposed outside the detection space, wherein the body-insertable apparatus includes a resonant circuit that generates a resonant magnetic field according to a driving magnetic field formed in the detection space, and the external device includes a sense coil that generates a detection signal according to a magnetic field formed in the detection space;

a drive coil that generates the driving magnetic field;

a driving-magnetic-field generating unit that inputs a drive signal for generating the driving magnetic field to the drive coil;

an auxiliary coil that generates a auxiliary magnetic field for reducing the driving magnetic field input to the sense coil;

an auxiliary-magnetic-field generating unit that inputs an auxiliary signal for generating the auxiliary magnetic field to the auxiliary coil;

a phase storage unit that stores a phase of the driving magnetic field formed in the detection space in a state with the body-insertable apparatus not being inserted into the detection space;

a combined-magnetic-field information storage unit that stores information of a combined magnetic field formed in the detection space, at a time of generating the driving magnetic field and the auxiliary magnetic field in a state with the body-insertable apparatus not being inserted into the detection space;

a signal processor that derives information of the magnetic field from the detection signal;

a position deriving unit that derives a position of the body-insertable apparatus by using information of the magnetic field derived by the signal processor, the phase stored in the phase storage unit, and information of the combined magnetic field stored in the combined-magnetic-field information storage unit; and a control unit that causes the signal processor to derive information of the magnetic field based on the detection signal read from the sense coil, in a state that the auxiliary-magnetic-field generating unit inputs the auxiliary signal to the auxiliary coil, while the driving-magnetic-field generating unit inputs the drive signal to the drive coil, and causes the position deriving unit to derive a position of the body-insertable apparatus by using the acquired information of the magnetic field, the phase stored in the phase storage unit, and information of the combined magnetic field stored in the combined-magnetic-field information storage unit.

10. The position detecting system according to claim 9, wherein information of the combined magnetic field is a complex vector including an intensity and a phase of the combined magnetic field, information of the magnetic field is a complex vector including an intensity and a phase of the magnetic field, and the position deriving unit subtracts the information of the combined magnetic field from the information of the magnetic field according to vector operation, to calculate a cosine component of the complex vector calculated by the subtraction with respect to the phase stored in the phase storage unit, and derives a position of the body-insertable apparatus by using the calculated cosine component.

11. The position detecting system according to claim 9, wherein the phase stored in the phase storage unit is a phase of the driving magnetic field detected by the sense coil at a time of generating the driving magnetic field, in a state with the body-insertable apparatus not being inserted into the detection space.

12. The position detecting system according to claim 10, wherein the phase stored in the phase storage unit is a phase of the driving magnetic field detected by a magnetic field sensor disposed in the detection space at a time of generating the driving magnetic field, in a state with the body-insertable apparatus not being inserted into the detection space.

13. A position detecting method for detecting a position of a body-insertable apparatus that is disposed in a detection space where a sense coil that detects a magnetic field, a drive coil that generates a driving magnetic field, and an auxiliary coil that generates a auxiliary magnetic field for reducing the driving magnetic field input to the sense coil are disposed, to generate a resonant magnetic field for detecting a position of the body-insertable apparatus according to the driving magnetic field, the position detecting method comprising:

detecting a phase of the driving magnetic field formed in the detection space in a state with the body-insertable apparatus not being disposed in the detection space;

acquiring information of a combined magnetic field formed in the detection space at a time of generating the driving magnetic field and the auxiliary magnetic field in a state with the body-insertable apparatus not being disposed in the detection space;

acquiring information of a magnetic field detected by the sense coil at a time of generating the driving magnetic field and the auxiliary magnetic field in a state with the body-insertable apparatus being disposed in the detection space; and deriving a position of the body-insertable apparatus by using the acquired information of the magnetic field detected by the sense coil, the phase, and the acquired information of the combined magnetic field.

14. The position detecting method according to claim 13, wherein information of the combined magnetic field is a complex vector including an intensity and a phase of the combined magnetic field, information of the magnetic field is a complex vector including an intensity and a phase of the magnetic field, and the deriving includes subtracting the information of the combined magnetic field from the information of the magnetic field according to vector operation, calculating a cosine component of the complex vector calculated by the subtraction with respect to the phase stored in the phase storage unit, and deriving a position of the body-insertable apparatus by using the calculated cosine component.

15. The position detecting method according to claim 13, wherein the detecting includes detecting a phase of the driving magnetic field detected by the sense coil at a time of generating the driving magnetic field in a state with the body-insertable apparatus not being inserted in the detection space.

16. The position detecting method according to claim 13, wherein the detecting the phase includes detecting a phase of the driving magnetic field detected by a magnetic field sensor disposed in the detection space at a time of generating the driving magnetic field in a state with the body-insertable apparatus not being inserted in the detection space.

17. A position detecting system comprising:
a detected object disposed in a detection space; and
an external device disposed outside the detection space, wherein
the detected object includes a resonant circuit that generates a resonant magnetic field according to a driving magnetic field formed in the detection space, and
the external device includes
- at least two drive coils that form the driving magnetic field in the detection space;
- at least two drive-signal input units that input a drive signal for forming the driving magnetic field to the drive coils, respectively;
- at least one sense coil that detects a magnetic field formed in the detection space;
- a signal adjustment unit that adjusts a phase or an amplitude of the drive signal input to each of the drive coils by the drive-signal input units, by using an evaluation function for evaluating the phase or the amplitude of the drive signal based on an intensity of the magnetic field detected by the sense coil; and
- a position deriving unit that derives a position of the detected object based on a magnetic field detected by the sense coil, wherein the evaluation function derives a solution by adding or multiplying a weight set according to at least one of a positional relation between each drive coil and each sense coil and a shape of each drive coil to or by the amplitude of the drive signal.

18. The position detecting system according to claim 17, wherein
the external device includes
- an auxiliary coil that generates an auxiliary magnetic field that negates a driving magnetic field input to at least one of the sense coils; and
- an auxiliary-signal input that inputs an auxiliary signal for causing the auxiliary coil to generate the auxiliary magnetic field, the signal adjustment unit adjusts at least one of a phase and an amplitude of at least one of the drive signal and the auxiliary signal, by using the evaluation function for evaluating the at least one of the phase and the amplitude of the at least one of the drive signal and the auxiliary signal based on an intensity of a magnetic field detected by the sense coils, and the evaluation function derives a solution by adding or multiplying a weight set according to a positional relation between the respective drive coils and the auxiliary coil, and each sense coil to or by an intensity of a magnetic field detected by the sense coil.

19. The position detecting system according to claim 17, wherein
the external device includes
- an auxiliary coil that generates an auxiliary magnetic field that negates a driving magnetic field input to at least one of the sense coils; and
- an auxiliary-signal input unit that inputs an auxiliary signal for causing the auxiliary coil to generate the auxiliary magnetic field, the signal adjustment unit adjusts the at least one of the phase and the amplitude of the at least one of the drive signal and the auxiliary signal, by using the evaluation function for evaluating the at least one of the phase and the amplitude of the at least one of the drive signal and the auxiliary signal based on an intensity of a magnetic field detected by the sense coil, and the evaluation function derives a solution by adding or multiplying a weight set according to at least one of a positional relation between the respective drive coils and the auxiliary coil, and each sense coil, and a shape of each drive coil.

20. The position detecting system according to claim 18, wherein the signal adjustment unit changes the weight based on at least one of an amplitude or a phase of the drive signal and an intensity of a magnetic field detected by the sense coils.

21. The position detecting system according to claim 19, wherein the signal adjustment unit changes the weight based on at least one of an amplitude or a phase of the drive signal and an intensity of a magnetic field detected by the sense coils.

22. A position detecting method for detecting a position of a detected object that is inserted into a detection space where at least two drive coils that form a driving magnetic field are disposed to generate a resonant magnetic field for detecting a position of the detected object according to the driving magnetic field, the position detecting method comprising:
detecting a magnetic field formed in the detection space by at least one sense coil provided outside the detected object, by inputting a drive signal to the drive coils in a state with the detected object not being inserted into the detection space;
adjusting a phase or an amplitude of the drive signal by using an evaluation function for evaluating the phase or the amplitude of the drive signal based on an intensity of the detected magnetic field;
forming a driving magnetic field in the detection space by inputting the drive signal, with a phase or an amplitude thereof being adjusted, to the drive coils in a state with the detected object being inserted into the detection space;
detecting a magnetic field in the detection space at a time of forming the driving magnetic field in the detection space by the at least one sense coil; and
deriving a position of the detected object based on the magnetic field detected at a time of forming the driving magnetic field in the detection space, wherein
the evaluation function derives a solution by adding or multiplying a weight set according to at least one of a positional relation between each drive coil and each sense coil and a shape of each drive coil to or by the amplitude of the drive signal.

23. The position detecting method according to claim 22, wherein the adjusting includes fixing a phase or an amplitude of at least one drive signal of the drive signals input to each of the at least two drive coils, and adjusting at least one of a phase and an amplitude of the other drive signal with respect to a drive signal with the phase or the amplitude being fixed.

* * * * *